(12) United States Patent
Li et al.

(10) Patent No.: US 11,718,583 B2
(45) Date of Patent: Aug. 8, 2023

(54) NITROGEN-CONTAINING COMPOUND, ELECTRONIC COMPONENT USING SAME AND ELECTRONIC DEVICE

(71) Applicant: Shaanxi Lighte Optoelectronics Material Co., Ltd., Xi'an (CN)

(72) Inventors: Jian Li, Xi'an (CN); Tiantian Ma, Xi'an (CN); Chao Yu, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/789,557

(22) PCT Filed: Apr. 8, 2021

(86) PCT No.: PCT/CN2021/086017
§ 371 (c)(1),
(2) Date: Jun. 28, 2022

(87) PCT Pub. No.: WO2021/218588
PCT Pub. Date: Nov. 4, 2021

(65) Prior Publication Data
US 2023/0139393 A1 May 4, 2023

(30) Foreign Application Priority Data

Apr. 30, 2020 (CN) .......................... 202010367827.1
Aug. 3, 2020 (CN) .......................... 202010768226.1

(51) Int. Cl.
*C07C 211/54* (2006.01)
*H01L 51/00* (2006.01)
(Continued)

(52) U.S. Cl.
CPC .......... *C07D 211/54* (2013.01); *C07C 255/42* (2013.01); *C07D 209/82* (2013.01);
(Continued)

(58) Field of Classification Search
CPC .................................................. C07C 211/54
See application file for complete search history.

(56) References Cited

FOREIGN PATENT DOCUMENTS

CN 109776594 A 5/2019
CN 110128279 A 8/2019
(Continued)

OTHER PUBLICATIONS

Computer-generated English-language translation of KR-20210025761-A.*

(Continued)

*Primary Examiner* — Vu A Nguyen
(74) *Attorney, Agent, or Firm* — Tucker Ellis LLP

(57) ABSTRACT

The present disclosure belongs to the field of organic electroluminescent materials, and specifically relates to a nitrogen-containing compound, an electronic component using the nitrogen-containing compound and an electronic device using the nitrogen-containing compound. The nitrogen-containing compound has a structure as shown in Formula 1. When the nitrogen-containing compound of the present disclosure is used in an organic electroluminescent device, properties of the device can be effectively improved.

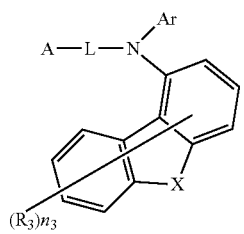

Formula 1

11 Claims, 1 Drawing Sheet

(51) Int. Cl.
   H01L 51/50    (2006.01)
   C07D 209/82   (2006.01)
   C07D 307/91   (2006.01)
   C07D 333/76   (2006.01)
   C07D 211/54   (2006.01)
   C07D 213/74   (2006.01)
   C07C 255/42   (2006.01)
   C07D 215/44   (2006.01)
   C07D 239/42   (2006.01)
   C07D 213/38   (2006.01)
   C07F 7/08     (2006.01)
   C07D 409/12   (2006.01)
   C07D 405/12   (2006.01)
   C07D 471/04   (2006.01)
   C07D 401/12   (2006.01)
   H10K 30/00    (2023.01)
   H10K 50/15    (2023.01)
   H10K 85/40    (2023.01)
   H10K 85/60    (2023.01)

(52) U.S. Cl.
   CPC ......... *C07D 213/38* (2013.01); *C07D 213/74* (2013.01); *C07D 215/44* (2013.01); *C07D 239/42* (2013.01); *C07D 307/91* (2013.01); *C07D 333/76* (2013.01); *C07D 401/12* (2013.01); *C07D 405/12* (2013.01); *C07D 409/12* (2013.01); *C07D 471/04* (2013.01); *C07F 7/0812* (2013.01); *H10K 30/00* (2023.02); *H10K 50/15* (2023.02); *H10K 85/40* (2023.02); *H10K 85/615* (2023.02); *H10K 85/631* (2023.02); *H10K 85/633* (2023.02); *H10K 85/636* (2023.02); *H10K 85/652* (2023.02); *H10K 85/654* (2023.02); *H10K 85/6572* (2023.02); *H10K 85/6576* (2023.02); *C07B 2200/05* (2013.01)

(56) References Cited

FOREIGN PATENT DOCUMENTS

| CN | 111454161 A |   | 7/2020  |           |
|----|-------------|---|---------|-----------|
| CN | 111777517 A |   | 10/2020 |           |
| CN | 112110825 A | * | 12/2020 | C07C 211/61 |
| KR | 20210025761 A | * | 3/2021 | C07C 211/61 |
| WO | 2020080849 A1 |   | 4/2020 |           |

OTHER PUBLICATIONS

Computer-generated English-language translation of CN-112110825-A.*

International Search Report from corresponding International Application No. PCT/CN2021/086017, dated Jun. 28, 2021, 4 pages with translation.

* cited by examiner

NITROGEN-CONTAINING COMPOUND, ELECTRONIC COMPONENT USING SAME AND ELECTRONIC DEVICE

CROSS REFERENCE TO RELATED APPLICATIONS

The present application claims the priority of Chinese Patent Application No. 202010367827.1, filed on Apr. 30, 2020 and the priority of Chinese Patent Application No. 202010768226.1, filed on Aug. 3, 2020, which are incorporated herein by reference in their entirety.

TECHNICAL FIELD

The present disclosure belongs to the technical field of organic light-emitting materials, and specifically provides a nitrogen-containing compound, an electronic component using the nitrogen-containing compound and an electronic device using the nitrogen-containing compound.

BACKGROUND

With the development of electronic technologies and the advancement of material sciences, electronic components for achieving electroluminescence or photoelectric conversion are being used in an increasingly wide range of applications. Such electronic component generally includes a cathode and an anode which is arranged oppositely to the cathode, and a functional layer arranged between the cathode and the anode. The functional layer consists of a plurality of organic or inorganic film layers, and the functional layer generally includes an energy conversion layer, a hole transporting layer located between the energy conversion layer and the anode, and an electron transporting layer located between the energy conversion layer and the cathode.

Taking an organic electroluminescent device as an example, it generally includes an anode, a hole transporting layer, an electroluminescent layer as an energy conversion layer, an electron transporting layer and a cathode that are sequentially stacked. When voltages are applied to the cathode and the anode, respectively, the two electrodes generate an electric field. Under the effect of the electric field, electrons on the cathode side move toward the electroluminescent layer, and holes on the anode side also move toward the electroluminescent layer, and the electrons and the holes are combined in the electroluminescent layer to form excitons. These excitons are in an excited state and release energy outward, so that the electroluminescent layer emits light outward.

At present, organic electroluminescent devices still have problems of poor performance, and in particular, it still has a need to solve the problem on how to further improve the lifetime or efficiency of the devices while ensuring low drive voltage.

SUMMARY

For the above problems of the prior art, the present disclosure aims to provide a nitrogen-containing compound, an electronic component using the nitrogen-containing compound and an electronic device using the nitrogen-containing compound, where the nitrogen-containing compound can be used in an organic electroluminescent device to improve the performance of the device.

In order to achieve the above purpose, a first aspect of the present disclosure provides a nitrogen-containing compound having a structure as represented by Formula 1:

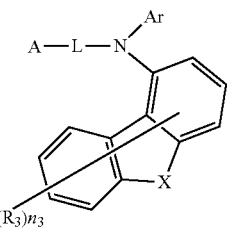

Formula 1 wherein X is selected from O, S, N($R_4$), C($R_5R_6$), Se, or Si($R_7R_8$), $R_4$ to $R_8$ are the same or different, and are each independently selected from an aryl with 6 to 18 carbon atoms, a heteroaryl with 3 to 18 carbon atoms, an alkyl with 1 to 10 carbon atoms, hydrogen, or a cycloalkyl with 3 to 10 carbon atoms;

Ar is selected from a substituted or unsubstituted aryl with 6 to 40 carbon atoms, or a substituted or unsubstituted heteroaryl with 2 to 40 carbon atoms;

L is selected from single bond, a substituted or unsubstituted arylene with 6 to 30 carbon atoms, or a substituted or unsubstituted heteroarylene with 2 to 30 carbon atoms;

A has a structure represented by the following Formula 1-1 or 1-2:

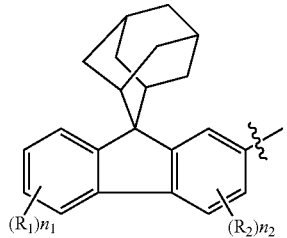

Formula 1-1

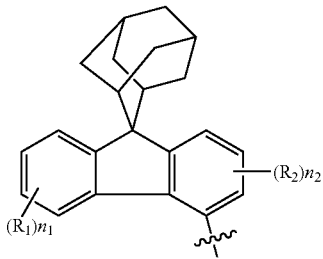

Formula 1-2 the substituents in L and Ar are the same or different, and are each independently selected from deuterium, halogen group, cyano, an alkyl with 1 to 10 carbon atoms, a haloalkyl with 1 to 10 carbon atoms, a cycloalkyl with 3 to 10 carbon atoms, an aryl with 6 to 20 carbon atoms, a heteroaryl with 3 to 18 carbon atoms, a trialkylsilyl with 3 to 18 carbon atoms, a triarylsilyl with 18 to 24 carbon atoms, an alkoxy with 1 to 10 carbon atoms, an alkylthio with 1 to 10 carbon atoms, an aryloxy with 6 to 18 carbon atoms, an arylthio with 6 to 18 carbon atoms, a heterocycloalkyl with 2 to 12 carbon atoms, or an alkenyl with 2 to 10 carbon atoms; optionally, any two adjacent substituents in L and Ar form a ring;

$R_1$ to $R_3$ are the same or different, and are each independently selected from deuterium, tritium, halogen group, cyano, an aryl with 6 to 20 carbon atoms, a heteroaryl with 3 to 15 carbon atoms, a trialkylsilyl with 3 to 18 carbon atoms, a triarylsilyl with 18 to 24 carbon atoms, an alkyl with 1 to 10 carbon atoms, a haloalkyl with 1 to 10 carbon atoms, an alkenyl with 2 to 10 carbon atoms, a cycloalkyl with 3 to 10 carbon atoms, a heterocycloalkyl with 2 to 10 carbon atoms, an alkylthio with 1 to 10 carbon atoms, an alkoxy with 1 to 10 carbon atoms, an aryloxy with 6 to 18 carbon atoms, or an arylthio with 6 to 18 carbon atoms; and $n_1$, $n_2$ and $n_3$ respectively represent the number of $R_1$, $R_2$ and $R_3$; $R_1$ to $R_3$ are represented by $R_j$, and $n_1$ to $n_3$ are represented by $n_j$, wherein j is a variable representing an integer of 1 to 3; when j is 1, $n_j$ is selected from 0, 1, 2, 3, or 4; when j is 2, $n_j$ is selected from 0, 1, 2, or 3; and when j is 3, $n_j$ is 0, 1, 2, 3, 4, 5, 6, or 7; optionally, any two adjacent $R_j$ form a ring.

A second aspect of the present disclosure provides an electronic component including the nitrogen-containing compound of the first aspect of the present disclosure.

A third aspect of the present disclosure provides an electronic device including the electronic component according to the second aspect of the present disclosure.

The structure formed by the combination of triarylamine and adamantane spirofluorene group in the nitrogen-containing compound of the present disclosure has good hole transporting characteristics and allows the molecule to have a relatively high rigidity. On the basis of this structure, the introduction of a specific substituent connected to N through a certain site into the triarylamine further deepens HOMO energy level of the compound. The compound, as a hole transport material, is used in an organic electroluminescent device, thereby further improving lifetime of the device while ensuring a relatively low drive voltage.

DESCRIPTION OF REFERENCE NUMERALS

Figure 1:
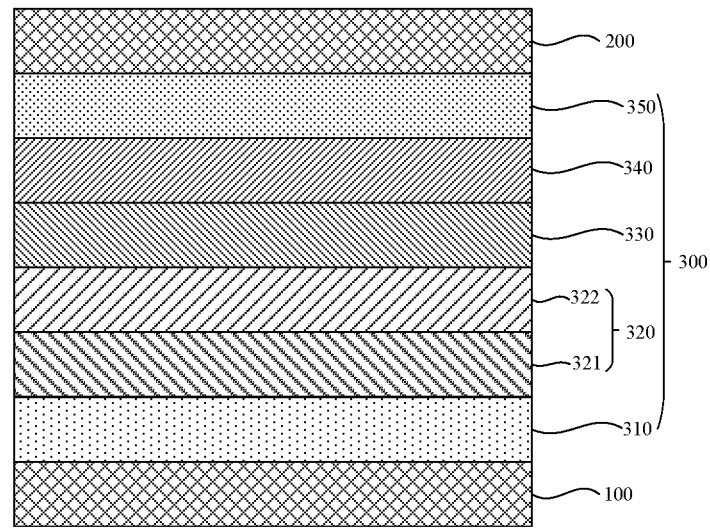
FIG. 1 is a schematic structural view of an organic electroluminescent device according to one embodiment of the present disclosure.

100: anode; 200: cathode; 300: functional layer; 310: hole injection layer; 320: hole transporting layer; 321: first hole transporting layer; 322: second hole transporting layer, 330: organic light-emitting layer; 340: electron transporting layer; 350: electron injection layer; 360: photoelectric conversion layer, 400: first electronic device; 500: second electronic device.

DETAILED DESCRIPTION

Specific embodiments of the present disclosure are described in detail below in conjunction with the accompanying drawings. It should be understood that the specific embodiments described herein are intended to illustrate and explain the disclosure only and are not intended to limit the disclosure.

In a first aspect, the present disclosure provides a nitrogen-containing compound having a structure represented by Formula 1:

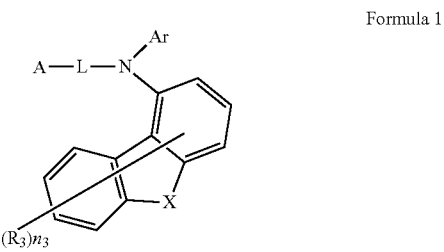

Formula 1 wherein X is selected from O, S, N($R_4$), C($R_5R_6$), Se, or Si($R_7R_8$), $R_4$ to $R_8$ are the same or different, and are each independently selected from an aryl with 6 to 18 carbon atoms, a heteroaryl with 3 to 18 carbon atoms, an alkyl with 1 to 10 carbon atoms, hydrogen, or a cycloalkyl with 3 to 10 carbon atoms;

Ar is selected from a substituted or unsubstituted aryl with 6 to 40 carbon atoms, or a substituted or unsubstituted heteroaryl with 2 to 40 carbon atoms;

L is selected from single bond, a substituted or unsubstituted arylene with 6 to 30 carbon atoms, or a substituted or unsubstituted heteroarylene with 2 to 30 carbon atoms;

A has a structure represented by the following Formula 1-1 or 1-2:

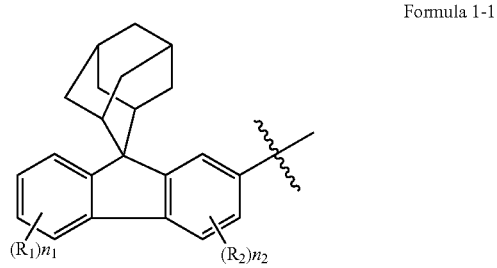

Formula 1-1

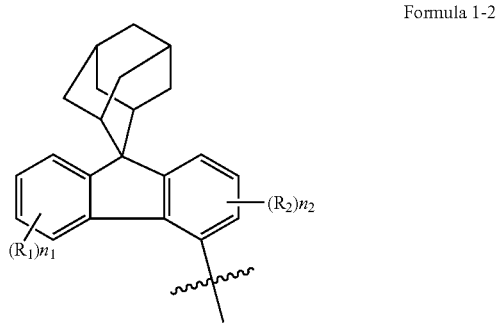

Formula 1-2 the substituents in L and Ar are the same or different, and are each independently selected from deuterium, halogen group, cyano, an alkyl with 1 to 10 carbon atoms, a haloalkyl with 1 to 10 carbon atoms, a cycloalkyl with 3 to 10 carbon atoms, an aryl with 6 to 20 carbon atoms, a heteroaryl with 3 to 18 carbon atoms, a trialkylsilyl with 3 to 18 carbon atoms, a triarylsilyl with 18 to 24 carbon atoms, an alkoxy with 1 to 10 carbon atoms, an alkylthio with 1 to 10 carbon atoms, an aryloxy with 6 to 18 carbon atoms, an arylthio with 6 to 18 carbon atoms, a heterocycloalkyl with 2 to 12 carbon atoms, or an alkenyl with 2 to 10 carbon atoms; optionally, any two adjacent substituents in L and Ar form a ring;

$R_1$ to $R_3$ are the same or different, and are each independently selected from deuterium, tritium, halogen group, cyano, an aryl with 6 to 20 carbon atoms, a heteroaryl with 3 to 15 carbon atoms, a trialkylsilyl with 3 to 18 carbon atoms, a triarylsilyl with 18 to 24 carbon atoms, an alkyl with 1 to 10 carbon atoms, a haloalkyl with 1 to 10 carbon atoms, an alkenyl with 2 to 10 carbon atoms, a cycloalkyl with 3 to 10 carbon atoms, a heterocycloalkyl with 2 to 10 carbon atoms, an alkylthio with 1 to 10 carbon atoms, an alkoxy with 1 to 10 carbon atoms, an aryloxy with 6 to 18 carbon atoms, or an arylthio with 6 to 18 carbon atoms; and $n_1$, $n_2$ and $n_3$ respectively represent the number of $R_1$, $R_2$ and $R_3$; $R_1$ to $R_3$ are represented by $R_j$, and $n_1$ to $n_3$ are represented by $n_j$, wherein j is a variable representing an integer of 1 to 3; when j is 1, $n_j$ is selected from 0, 1, 2, 3, or 4; when j is 2, $n_j$ is selected from 0, 1, 2, or 3; and when j is 3, $n_j$ is 0, 1, 2, 3, 4, 5, 6, or 7; optionally, any two adjacent $R_j$ form a ring.

In the present disclosure, the expressions of "each . . . independently is", " . . . each independently are"and" . . . each independently selected from" may be interchanged. These expressions will be understood in a broad sense, and may mean that, the specific options expressed by the same symbol in different groups do not affect each other, or that the specific options expressed by the same symbol in the same group do not affect each other. For example, Formula Q-1

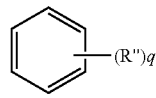

Formula Q-2

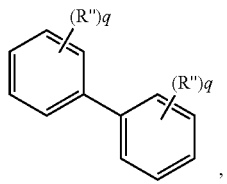

wherein each q is independently 0, 1, 2, or 3, and each R" is independently selected from hydrogen, deuterium, fluorine, or chlorine. This means that, Formula Q-1 represents that there are substituents R" in an amount of q on the benzene ring, each R" may be the same or different, and the options of each R" do not affect each other; Formula Q-2 represents that there are substituents R" in an amount of q on each of benzene rings in the biphenyl, the number q of the substituents R" on the two benzene rings are the same or different, each R" may be the same or different, and the options of each R" do not affect each other.

In the present disclosure, the terms "optional" and "optionally" means that the subsequent event or circumstance described may, but does not have to, occur. The description includes instances where the event or circumstance occurs or does not occur. For example, "optionally, any two adjacent substituents form a ring" means that the two substituents may form a ring but do not have to form a ring, including a situation in which two adjacent substituents form a ring and a situation in which two adjacent substituents do not form a ring.

In the present disclosure, the term "substituted or unsubstituted" means that the functional groups listed after the term may or may not have a substituent (hereinafter the substituents are collectively referred to as Rc for describing easily). For example, "substituted or unsubstituted aryl" refers to an aryl with a substituent Rc or an unsubstituted aryl. The substituent described above, namely Rc, may be, for example, deuterium, tritium, halogen group, cyano, an aryl with 6 to 20 carbon atoms, a heteroaryl with 3 to 18 carbon atoms, a trialkylsilyl with 3 to 18 carbon atoms, a triarylsilyl with 18 to 24 carbon atoms, an alkyl with 1 to 10 carbon atoms, a haloalkyl with 1 to 10 carbon atoms, an alkenyl with 2 to 10 carbon atoms, a cycloalkyl with 3 to 10 carbon atoms, a heterocycloalkyl with 2 to 12 carbon atoms, an alkylthio with 1 to 10 carbon atoms, an alkoxy with 1 to 10 carbon atoms, an aryloxy with 6 to 18 carbon atoms, and an arylthio with 6 to 18 carbon atoms. When the number of substituents is greater than 2, the substituents may be the same or different. In addition, when two substituents Rc are connected to the same atom, the two substituents Rc may be independently present, or be connected to each other to form a ring together with the atom. When two adjacent substituents Rc are present on the functional group, the two adjacent substituents Rc may be present independently, or be fused into a ring together with the functional group to which they are connected.

In the present disclosure, the number of carbon atoms of a substituted or unsubstituted functional group refers to the number of all carbon atoms. For example, if L is a substituted arylene with 12 carbon atoms, the number of all carbon atoms of the arylene and substituents thereon is 12.

In the present disclosure, "aryl" refers to an optional functional group or substituent derived from an aromatic carbocyclic ring. The aryl may be a monocyclic aryl (e.g., phenyl) or a polycyclic aryl. In other words, the aryl may be a monocyclic aryl, a fused cyclic aryl, a group formed by conjugative connection of two or more monocyclic aryls, a group formed by conjugative connection of a monocyclic aryl and a fused cyclic aryl, or a group formed by conjugative connection of two or more fused cyclic aryls. That is, unless otherwise stated, a group formed by conjugative connection of two or more aromatic groups may also be considered as the aryl of the present disclosure. The fused cyclic aryl may include, for example, a fused bicyclic aryl (e.g., naphthyl), a fused tricyclic aryl (e.g., phenanthryl, fluorenyl, anthryl), and the like. The aryl does not contain heteroatoms such as B, N, O, S, P, Se, Si and the like. For example, biphenyl, tribiphenyl and the like are the aryl. Examples of the aryl may include, but are not limited to, phenyl, naphthyl, fluorenyl, anthryl, phenanthryl, biphenyl, terphenyl, quaterphenyl, quinquephenyl, benzo[9,10] phenanthryl, pyrenyl, benzofluoranthenyl, chrysenyl and the like. In the present disclosure, the arylene involved refers to a divalent group formed by loss of one hydrogen atom of the aryl.

In the present disclosure, the substituted aryl may be an aryl in which one or two or more hydrogen atoms are substituted by a group such as deuterium atom, halogen group, —CN, aryl, heteroaryl, trialkylsilyl, alkyl, cycloalkyl, alkoxy, alkylthio and the like. Specific examples of the aryl substituted by heteroaryl include, but are not limited to, a phenyl substituted by dibenzofuryl, a phenyl substituted by dibenzothiophenyl, a phenyl substituted by pyridyl, and the like. It will be understood that the number of carbon atoms of the substituted aryl refers to the total number of carbon atoms of aryl and substituents thereon. For example, a substituted aryl with 18 carbon atoms refers to that the total number of carbon atoms of the aryl and the substituents is 18.

In the present disclosure, "heteroaryl" refers to a monovalent aromatic ring or derivative thereof containing at least one heteroatom in the ring. The heteroatom may be at least one of B, O, N, P, Si, Se and S. The heteroaryl may be a monocyclic heteroaryl or a polycyclic heteroaryl. In other words, the heteroaryl may be a single aromatic ring system; or may be a system formed by a plurality of aromatic ring systems via conjugative connection of carbon-carbon bonds, and any of the aromatic ring systems may be an aromatic monocyclic ring or an aromatic fused ring. By way of example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinoyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silafluorenyl, dibenzofuryl, and N-phenylcarbazolyl, N-pyridylcarbazolyl, N-methylcarbazolyl, or the like, and are not limited thereto. Among them, thienyl, furyl, phenanthrolinyl and the like are heteroaryl having a single aromatic ring system, and N-phenylcarbazolyl, N-pyridylcarbazolyl are heteroaryl having a polycyclic system that is formed by conjugative connection of carbon-carbon bonds. In the present disclosure, the heteroarylene involved refers to a divalent group formed by further loss of one hydrogen atom from the heteroaryl.

In the present disclosure, the substituted heteroaryl may be a heteroaryl in which one or two or more hydrogen atoms are substituted by a group such as deuterium atom, halogen group, —CN, aryl, heteroaryl, trialkylsilyl, alkyl, cycloalkyl, alkoxy, and alkylthio. It will be understood that the number of carbon atoms of the substituted heteroaryl refers to the total number of carbon atoms of the heteroaryl and the substituents in it.

In the present disclosure, in expression of "any two adjacent $R_j$ form a ring", the "any two adjacent $R_j$" means that two $R_j$ are located on a same atom, or two adjacent atoms have one $R_j$ respectively. When two $R_j$ are located on the same atom, the two $R_j$ may form a saturated or unsaturated ring together with the atom to which they are jointly connected. When two adjacent atoms respectively have one $R_j$, the two $R_j$ may be fused into a ring. Similarly, any two adjacent substituents forming a ring have the same explanation, which will not be repeated in the present disclosure.

In the present disclosure, a nonlocalized linkage bond refers to a single bond

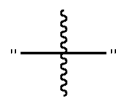

extending from a ring system, and the single bond

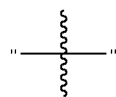

indicates that one end of the bond can be connected to any position in the ring system through which the bond intersects, and the other end is connected to the rest of a compound molecule.

For example, as shown in the following Formula (f), the naphthyl represented by the Formula (f) is connected to other positions of a molecule by two nonlocalized linkage bonds intersecting the bicyclic ring, with the meaning of including any possible connection manner as shown in the Formula (f-1) to (f-10).

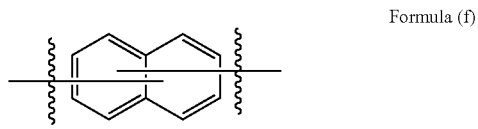

Formula (f)

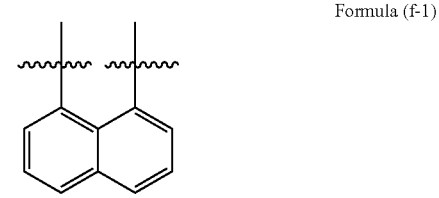

Formula (f-1)

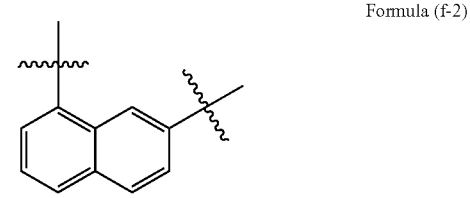

Formula (f-2)

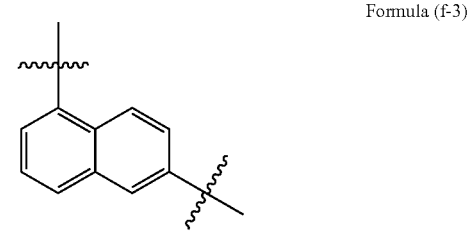

Formula (f-3)

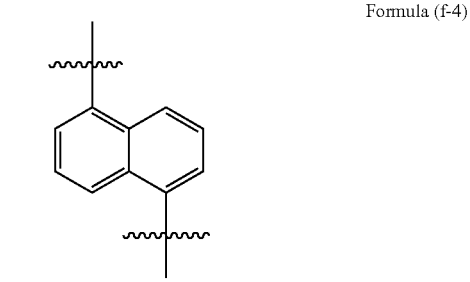

Formula (f-4)

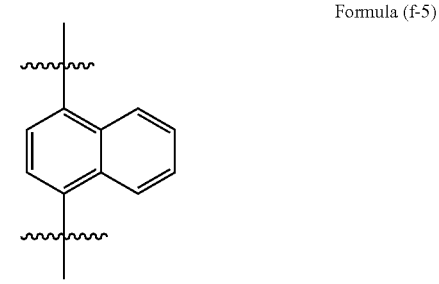

Formula (f-5)

Formula (f-6)

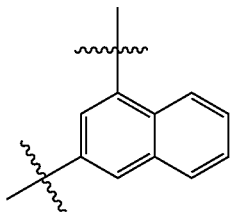

Formula (f-7)

Formula (f-8)

Formula (f-9)

Formula (f-10)

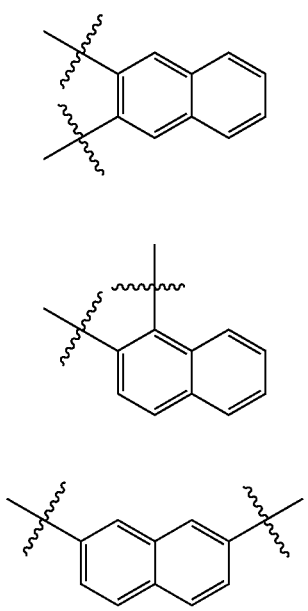

For another example, as shown in the following formula (X'), the phenanthryl represented by the formula (X') is connected to other positions of a molecule by a nonlocalized linkage bond extending from the center of a benzene ring on one side, with the meaning of including any possible connection manner as shown in the formula (X'-1) to (X'-4).

(X')

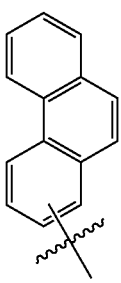

(X'-1)

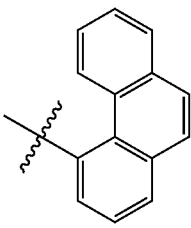

(X'-2)

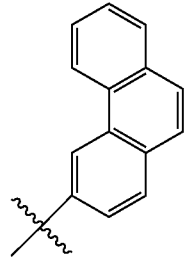

(X'-3)

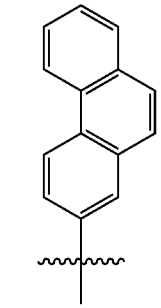

(X'-4)

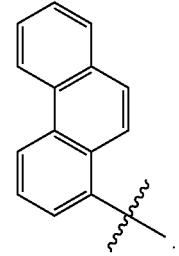

A nonlocalized substituent in the present disclosure refers to a substituent connected by a single bond extending from the center of a ring system, and indicates that the substituent may be connected to any possible position in the ring system. For example, as shown in the following Formula (Y), the substituent R' represented by the Formula (Y) is connected to a quinoline ring by a nonlocalized linkage bond, with the meaning of including any possible connection manner as shown in the Formula (Y-1) to (Y-7).

Formula (Y)

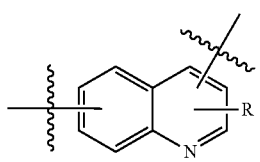

-continued

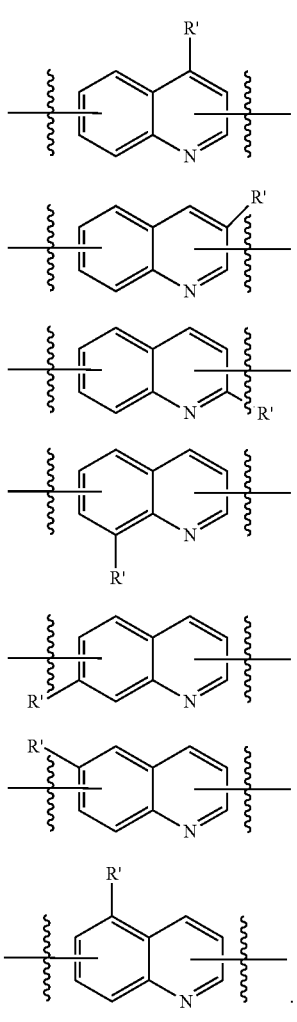

Formula (Y-1)

Formula (Y-2)

Formula (Y-3)

Formula (Y-4)

Formula (Y-5)

Formula (Y-6)

Formula (Y-7)

In the present disclosure, the alkyl with 1 to 10 carbon atoms may include a linear alkyl with 1 to 10 carbon atoms and a branched alkyl with 3 to 10 carbon atoms, and the number of carbon atoms may be, for example, 1, 2, 3, 4, 5, 6, 7, 8, 9, or 10. Specific examples of alkyl with 1 to 10 carbon atoms include, but are not limited to, methyl, ethyl, n-propyl, isopropyl, n-butyl, isobutyl, tert-butyl, n-pentyl, iso-pentyl, neopentyl, cyclopentyl, n-hexyl, heptyl, n-octyl, 2-ethylhexyl, nonyl, decyl, 3,7-dimethyloctyl and the like.

In the present disclosure, the halogen group may include fluorine, iodine, bromine, chlorine and the like.

In the present disclosure, the aryl with 6 to 20 carbon atoms has, for example, 6 (phenyl), 10 (naphthyl), 12, 14, 15 (dimethylfluorenyl), or 16 carbon atoms and so on. The heteroaryl with 3 to 18 carbon atoms has, for example, 5, 8, 12, 15, or 18 carbon atoms and so on.

In the present disclosure, specific examples of the trialkylsilyl with 3 to 18 carbon atoms include, but are not limited to, trimethylsilyl, ethyldimethylsilyl, triethylsilyl and the like.

In the present disclosure, specific examples of the cycloalkyl with 3 to 10 carbon atoms include, but are not limited to, cyclopentyl, cyclohexyl, adamantyl and the like.

Alternatively, $R_4$ is selected from an aryl with 6 to 12 carbon atoms, or a heteroaryl with 3 to 12 carbon atoms.

Alternatively, $R_5$ to Ra are the same or different, and are each independently selected from an alkyl with 1 to 4 carbon atoms, or an aryl with 6 to 12 carbon atoms.

In some embodiments, the nitrogen-containing compound is selected from the group consisting of structures represented by Formula A to F:

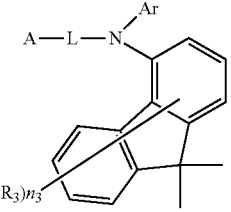

Formula A

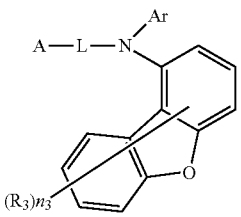

Formula B

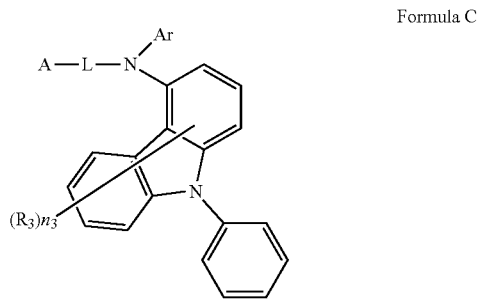

Formula C

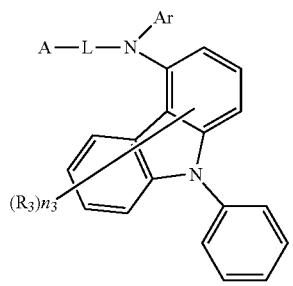

Formula D

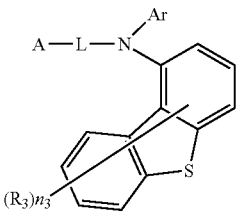

Formula E

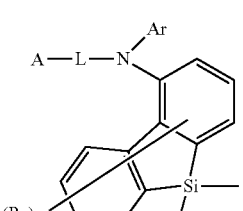

Formula F

Alternatively, $R_1$ to $R_3$ are the same or different, and are each independently selected from deuterium, fluorine, cyano, an alkyl with 1 to 4 carbon atoms, a fluoroalkyl with 1 to 4 carbon atoms, a cycloalkyl with 5 to 10 carbon atoms, a trialkylsilyl with 3 to 7 carbon atoms, an aryl with 6 to 12 carbon atoms, triphenylsilyl, an alkoxy with 1 to 4 carbon atoms, or an alkylthio with 1 to 4 carbon atoms.

According to one exemplary embodiment, $R_1$ and $R_2$ are the same or different, and are each independently selected from deuterium, fluorine, cyano, methyl, ethyl, n-propyl, isopropyl, tert-butyl, methoxy, trifluoromethyl, cyclopentyl, cyclohexyl, trimethylsilyl, phenyl, or naphthyl.

According to one exemplary embodiment, $R_3$ is selected from deuterium, fluorine, cyano, methyl, tert-butyl, trifluoromethyl, cyclopentyl, cyclohexyl, trimethylsilyl, or phenyl.

Alternatively, $n_1$ and $n_2$ are each independently selected from 0, 1, 2 or 3.

Alternatively, $n_3$ is selected from 0, 1, 2 or 3.

Alternatively, the substituents in L and Ar are the same or different, and are each independently selected from deuterium, fluorine, cyano, an alkylthio with 1 to 4 carbon atoms, an alkyl with 1 to 4 carbon atoms, a haloalkyl with 1 to 4 carbon atoms, a cycloalkyl with 5 to 10 carbon atoms, an aryl with 6 to 15 carbon atoms, a heteroaryl with 5 to 12 carbon atoms, a trialkylsilyl with 3 to 7 carbon atoms, triphenylsilyl, or an alkoxy with 1 to 4 carbon atoms.

Alternatively, Ar is selected from a substituted or unsubstituted aryl with 6 to 26 carbon atoms, or a substituted or unsubstituted heteroaryl with 3 to 24 carbon atoms.

According to one embodiment, Ar may be selected from the groups represented by formula i-1 to i-15:

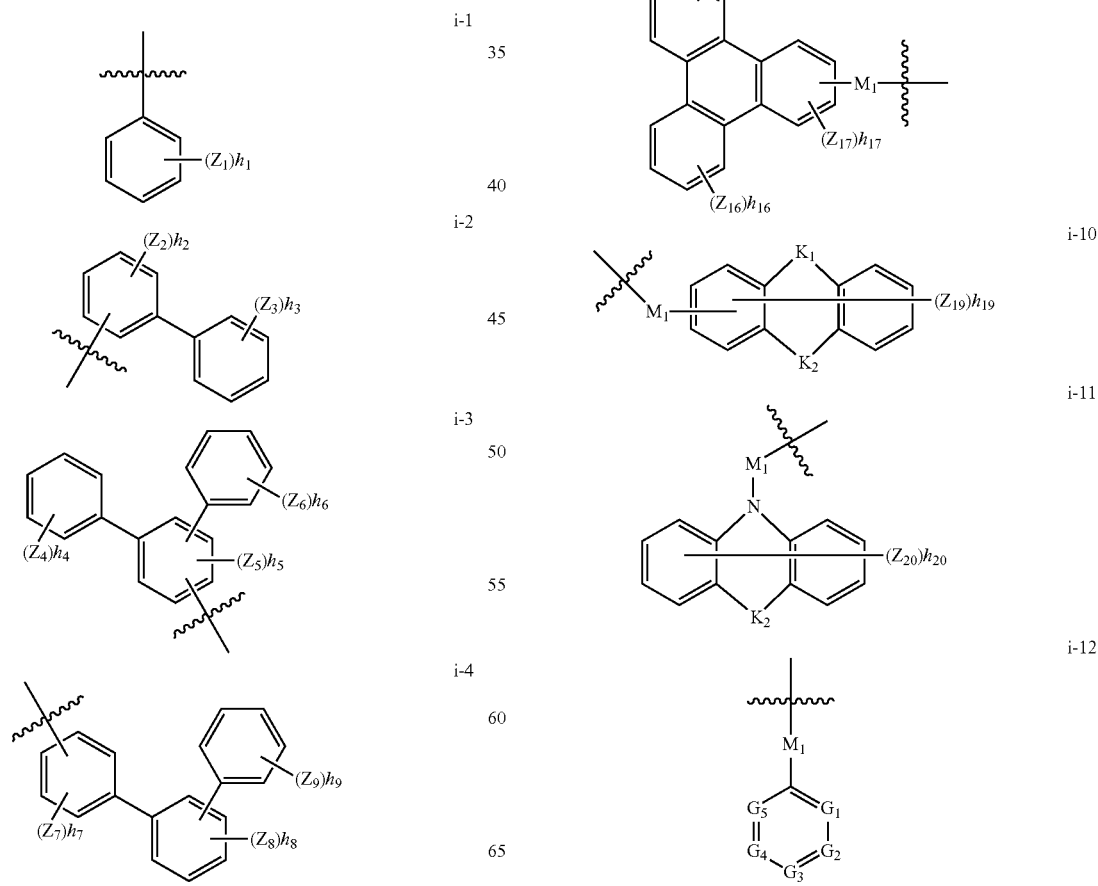

-continued

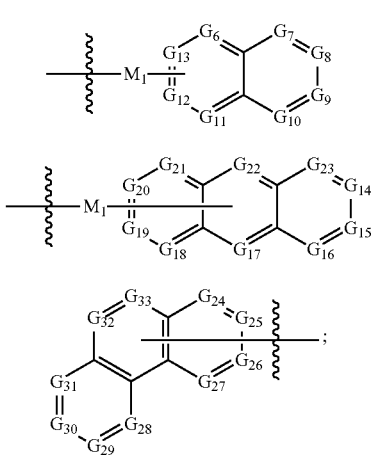

wherein

represents a chemical bond, and $M_1$ is selected from single bond or

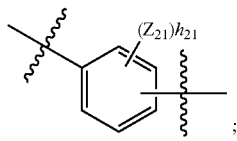

$G_1$ to $G_5$ are each independently selected from N or $C(F_1)$, and at least one of $G_1$ to $G_5$ is selected from N; when two or more of $G_1$ to $G_5$ are selected from $C(F_1)$, any two $F_1$ are the same or different;

$G_6$ to $G_{13}$ are each independently selected from N or $C(F_2)$, and at least one of $G_6$ to $G_{13}$ is selected from N; when two or more of $G_6$ to $G_{13}$ are selected from $C(F_2)$, any two $F_2$ are the same or different;

$G_{14}$ to $G_{23}$ are each independently selected from N or $C(F_3)$, and at least one of $G_{14}$ to $G_{23}$ is selected from N; when two or more of $G_{14}$ to $G_{23}$ are selected from $C(F_3)$, any two $F_3$ are the same or different;

$G_{24}$ to $G_{33}$ are each independently selected from N or $C(F_4)$, and at least one of $G_{24}$ to $G_{33}$ is selected from N; when two or more of $G_{24}$ to $G_{33}$ are selected from $C(F_4)$, any two $F_4$ are the same or different;

$Z_1$ is selected from hydrogen, deuterium, fluorine, chlorine, bromine, cyano, a trialkylsilyl with 3 to 12 carbon atoms, an alkyl with 1 to 10 carbon atoms, a haloalkyl with 1 to 10 carbon atoms, a cycloalkyl with 3 to 10 carbon atoms, an alkoxy with 1 to 10 carbon atoms, an alkylthio with 1 to 10 carbon atoms, or a triarylsilyl with 18 to 24 carbon atoms;

$Z_2$ to $Z_9$ and $Z_{21}$ are each independently selected from hydrogen, deuterium, fluorine, chlorine, bromine, cyano, a trialkylsilyl with 3 to 12 carbon atoms, an alkyl with 1 to 10 carbon atoms, a haloalkyl with 1 to 10 carbon atoms, a cycloalkyl with 3 to 10 carbon atoms, an alkoxy with 1 to 10 carbon atoms, an alkylthio with 1 to 10 carbon atoms, a heteroaryl with 3 to 18 carbon atoms, or a triarylsilyl with 18 to 24 carbon atoms;

$Z_{10}$ to $Z_{20}$ and $F_1$ to $F_4$ are each independently selected from hydrogen, deuterium, fluorine, chlorine, bromine, cyano, a trialkylsilyl with 3 to 12 carbon atoms, an alkyl with 1 to 10 carbon atoms, a haloalkyl with 1 to 10 carbon atoms, a cycloalkyl with 3 to 10 carbon atoms, an alkoxy with 1 to 10 carbon atoms, an alkylthio with 1 to 10 carbon atoms, an aryl with 6 to 18 carbon atoms, a heteroaryl with 3 to 18 carbon atoms, or a triarylsilyl with 18 to 24 carbon atoms;

$h_1$ to $h_{21}$ are represented by $h_k$, and $Z_1$ to $Z_{21}$ are represented by $Z_k$, wherein k is a variable representing any integer of 1 to 21, and $h_k$ represents the number of substituents $H_k$. When k is selected from 5 or 17, $h_k$ is selected from 1, 2, or 3; when k is selected from 2, 7, 8, 12, 15, 16, 18, or 21, $h_k$ is selected from 1, 2, 3, or 4; when k is selected from 1, 3, 4, 6, 9, or 14, $h_k$ is selected from 1, 2, 3, 4, or 5; when k is 13, $h_k$ is selected from 1, 2, 3, 4, 5 or 6; when k is selected from 10 or 19, $h_k$ is selected from 1, 2, 3, 4, 5, 6, or 7; when k is 20, $h_k$ is selected from 1, 2, 3, 4, 5, 6, 7, or 8; when k is 11, $h_k$ is selected from 1, 2, 3, 4, 5, 6, 7, 8, or 9; and when $h_k$ is greater than 1, any two $Z_k$ are the same or different; optionally, any two adjacent $Z_k$ form a ring;

$K_1$ is selected from O, S, $N(Z_{22})$, $C(Z_{23}Z_{24})$, or $Si(Z_{23}Z_{24})$; wherein $Z_{22}$, $Z_{23}$, and $Z_{24}$ are each independently selected from hydrogen, an aryl with 6 to 18 carbon atoms, a heteroaryl with 3 to 18 carbon atoms, an alkyl with 1 to 10 carbon atoms, or a cycloalkyl with 3 to 10 carbon atoms, or $Z_{23}$ and $Z_{24}$ are connected to each other to form a saturated or unsaturated ring having 5 to 15 carbon atoms together with the atom to which they are jointly connected;

$K_2$ is selected from single bond, O, S, $N(Z_{25})$, $C(Z_{26}Z_{27})$, or $Si(Z_{26}Z_{27})$; wherein $Z_{25}$, $Z_{26}$, and $Z_{27}$ are each independently selected from hydrogen, an aryl with 6 to 18 carbon atoms, a heteroaryl with 3 to 18 carbon atoms, an alkyl with 1 to 10 carbon atoms, or a cycloalkyl with 3 to 10 carbon atoms, or $Z_{26}$ and $Z_{27}$ are connected to each other to form a saturated or unsaturated ring having 5 to 15 carbon atoms together with the atom to which they are jointly connected.

In formula i-13 to i-15, $F_2$ to $F_4$ may be represented by $F_i$, wherein i is a variable representing 2, 3 or 4. For example, $F_i$ refers to $F_2$ when i is 2. It will be understood that, $F_i$ in the $C(F_i)$ is not present when a nonlocalized linkage bond is connected to $C(F_i)$. For example, in formula i-13, when

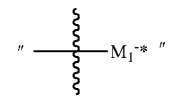

is connected to $G_{12}$, $G_{12}$ can only represent C atom. That is, a specific structure of formula i-13 is shown as

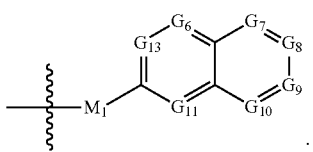

In the present disclosure, two groups in a group of $Z_{23}$ and $Z_{24}$ or two groups in a group of $Z_{26}$ and $Z_{27}$ may be connected to each other to form a saturated or unsaturated ring, for example, may form a saturated or unsaturated 3- to 13-membered ring. For example, in formula i-10, when both of $K_2$ and $M_1$ are single bond, $Z_{19}$ is hydrogen, and $K_1$ is $C(Z_{23}Z_{24})$, $Z_{23}$ and $Z_{24}$ are connected to each other to form 5-membered ring together with the atom to which they are jointly connected, the formula i-10 is

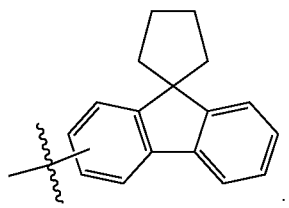

Likewise, formula i-10 may also represent

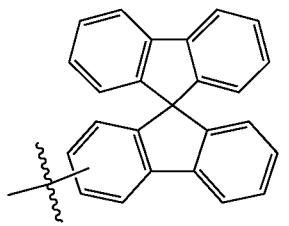

, in which $H_{23}$ and $H_{24}$ are connected to each other to form a partially unsaturated 13-membered ring together with the atom to which they are jointly connected.

Alternatively, Ar is a substituted or unsubstituted group $V_1$, wherein the unsubstituted group $V_1$ is selected from the following groups:

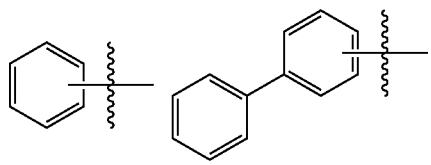

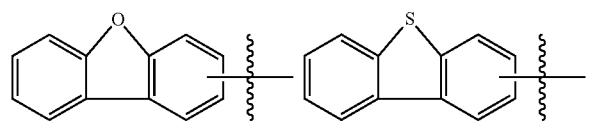

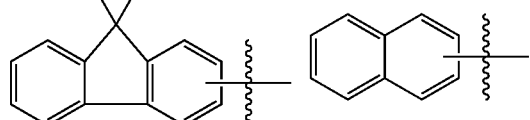

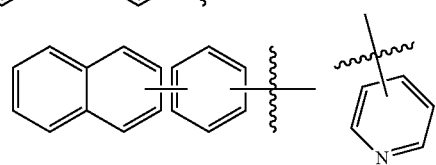

-continued

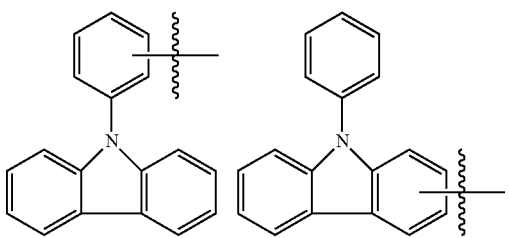

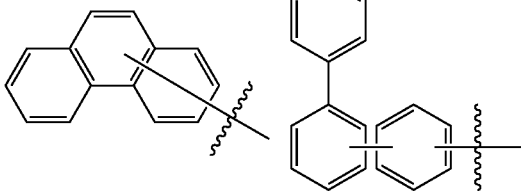

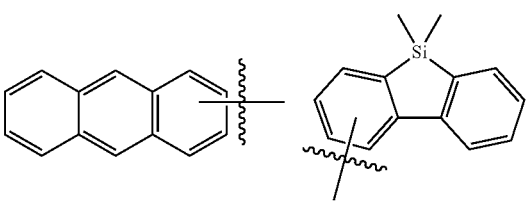

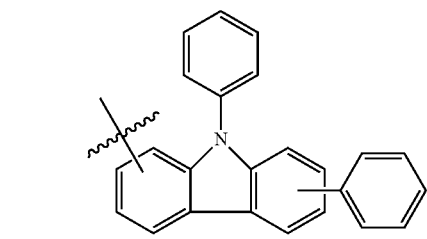

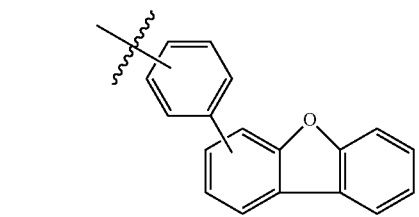

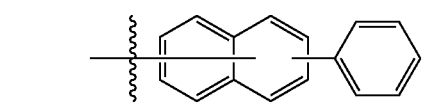

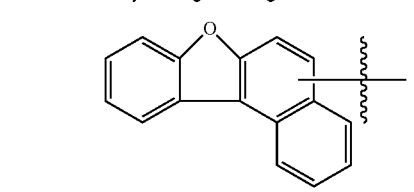

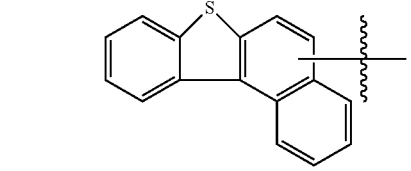

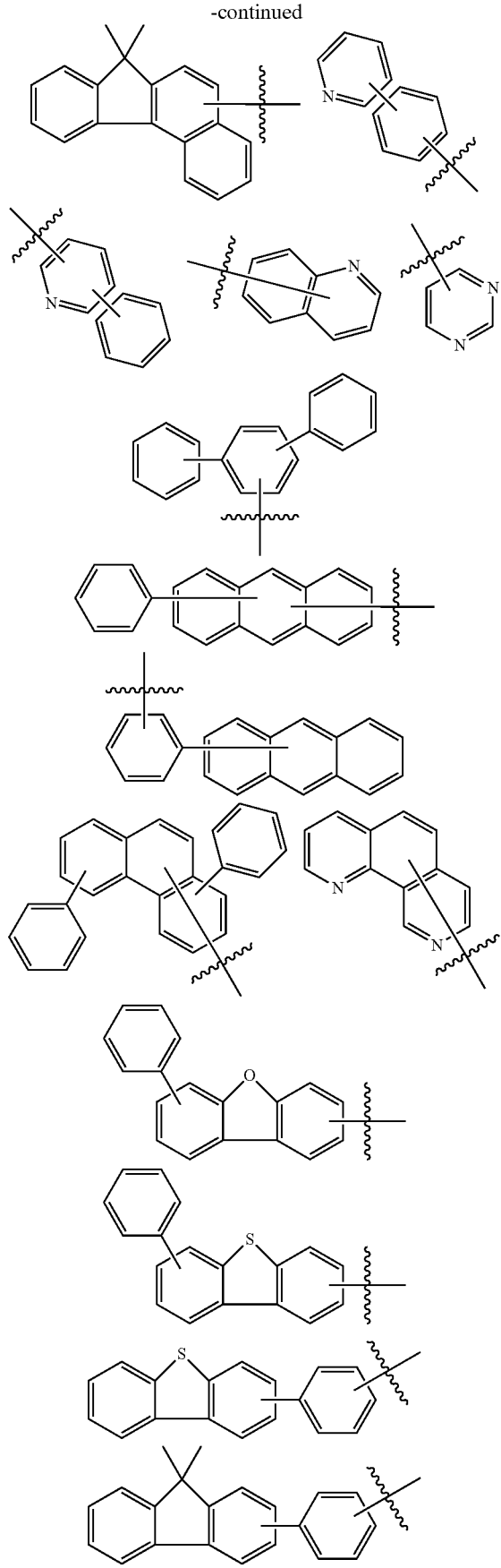

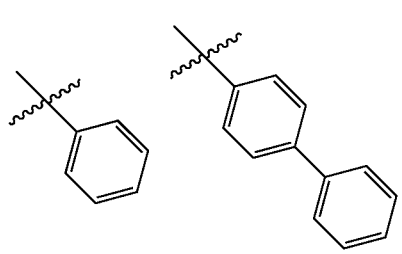

the substituted group $V_1$ has one or two or more substituents, the substituents in the substituted group $V_1$ are each independently selected from deuterium, fluorine, cyano, an alkyl with 1 to 4 carbon atoms, a fluoroalkyl with 1 to 4 carbon atoms, a cycloalkyl with 5 to 10 carbon atoms, a trialkylsilyl with 3 to 7 carbon atoms, pyridyl, an alkoxy with 1 to 4 carbon atoms, or an alkylthio with 1 to 4 carbon atoms. If the number of substituents in the substituted group $V_1$ is greater than 1, each substituent may be the same or different.

Further alternatively, Ar is selected from the following groups:

-continued
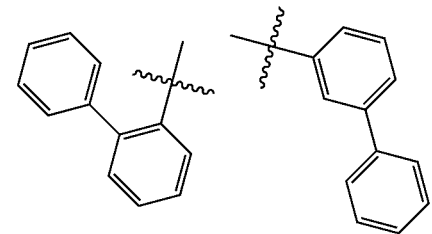
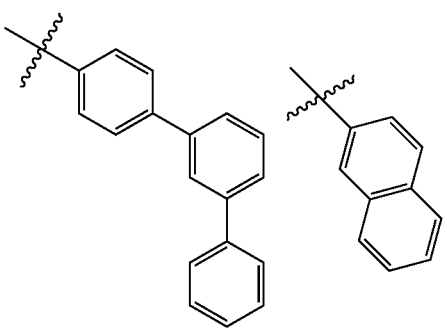
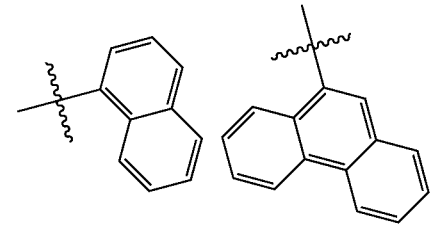
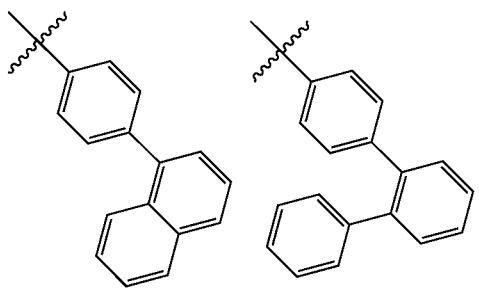
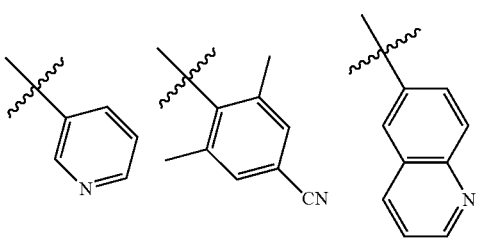
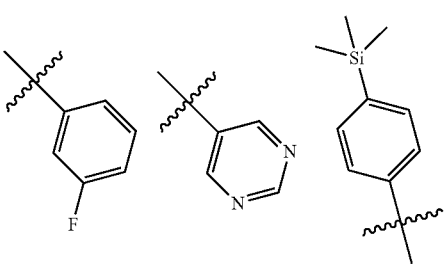
-continued
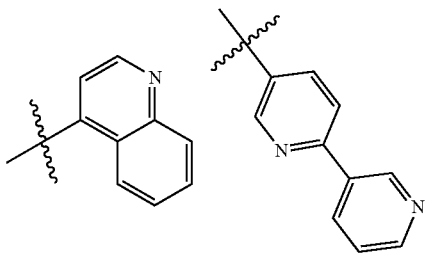
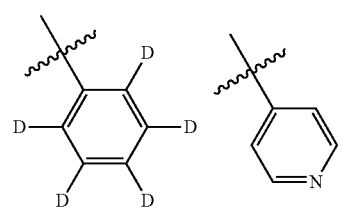
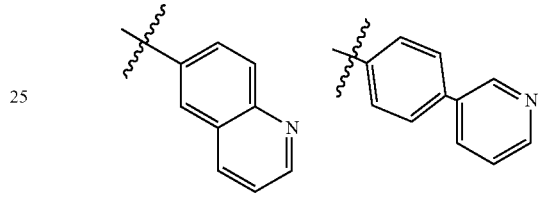
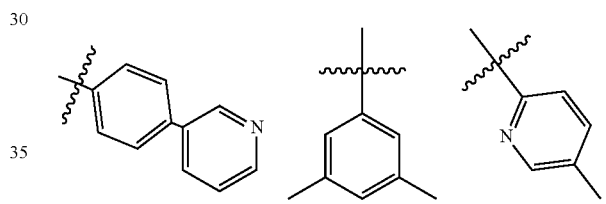
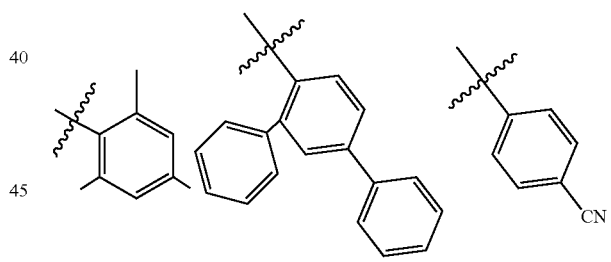
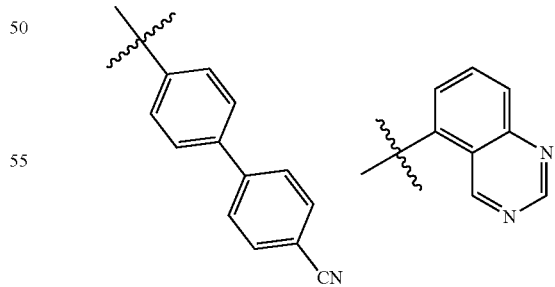
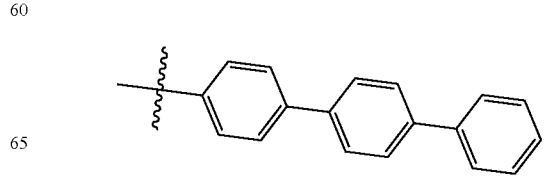

-continued
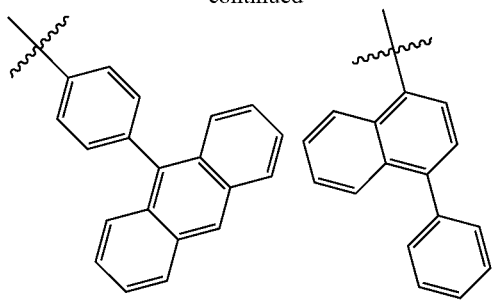
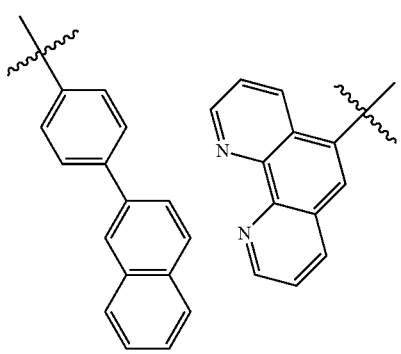
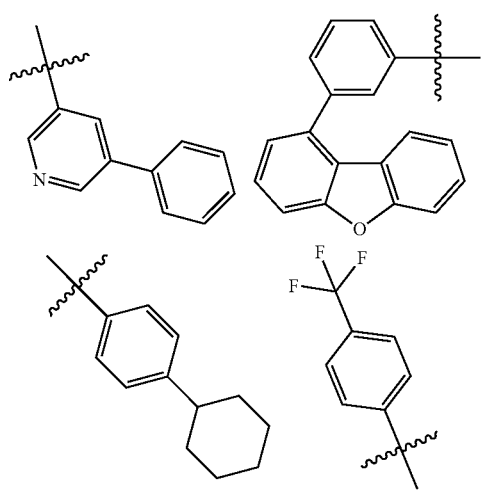
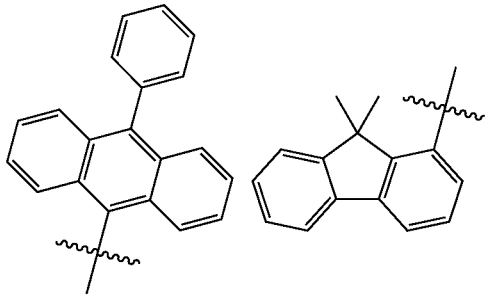
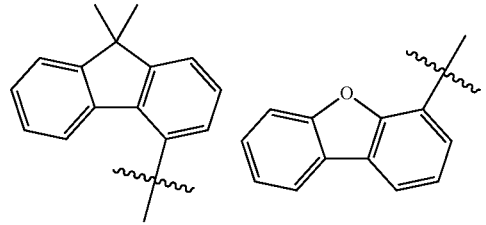
-continued
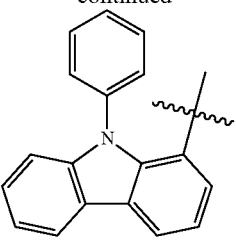
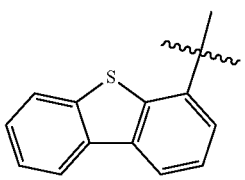
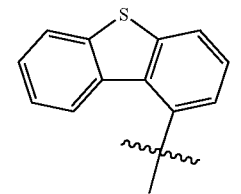
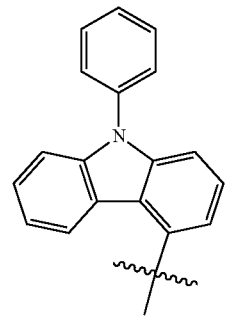
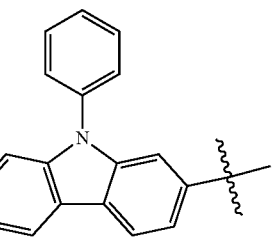
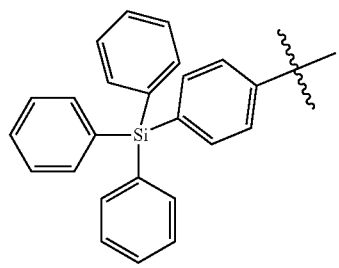

-continued

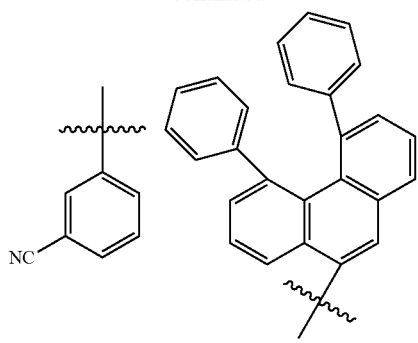

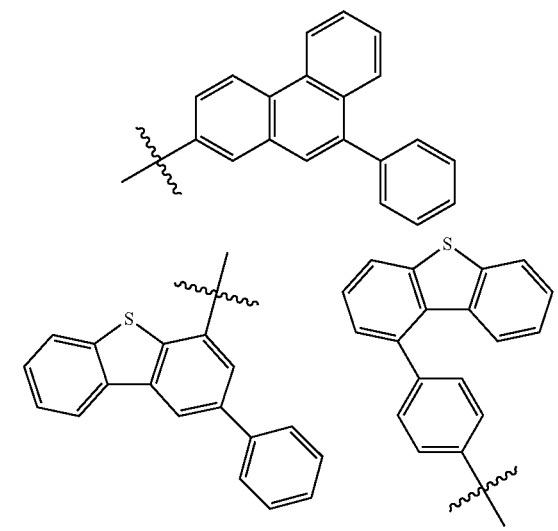

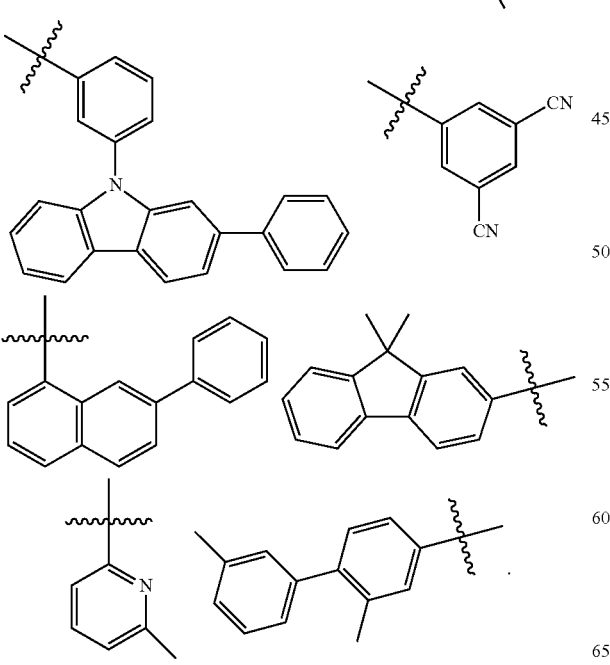

According to one preferred embodiment, in

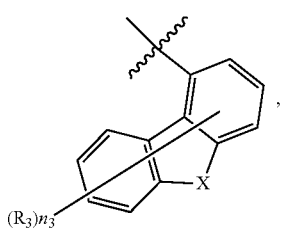

X is selected from O, S, N(Ph), or $C(CH_3)_2$, and $n_3$ is selected from 0 or 1; $R_3$ is selected from methyl, tert-butyl, fluorine, —CN, or trimethylsilyl; Ar is selected from dibenzofuryl, dibenzothiophenyl, 9,9-dimethylfluorenyl, or N-phenylcarbazolyl. In this case, the nitrogen-containing compound, as a hole transporting layer material, further improves the performance of OLED devices.

Alternatively,

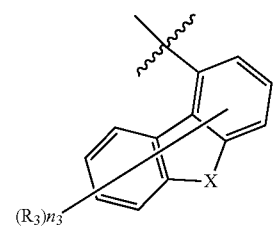

is selected from

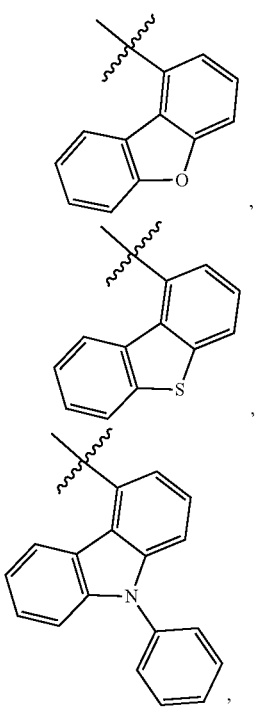

, or

-continued

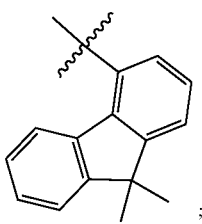

;

Ar is selected from

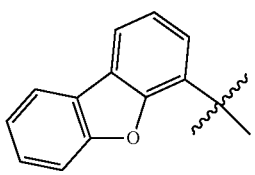

,

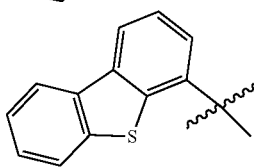

,

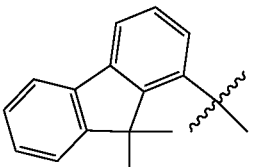

,

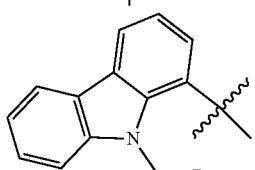

,

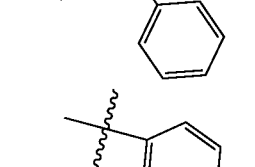

,

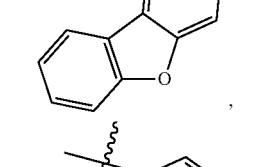

,

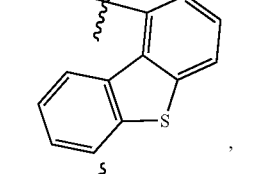

, or

-continued

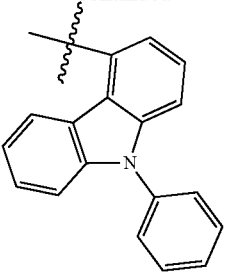

.

Alternatively, L is selected from single bond, a substituted or unsubstituted arylene with 6 to 20 carbon atoms, or a substituted or unsubstituted heteroarylene with 5 to 25 carbon atoms.

According to one embodiment, L is selected from single bond, or a substituted or unsubstituted group $V_2$, wherein the unsubstituted group $V_2$ is selected from the following groups:

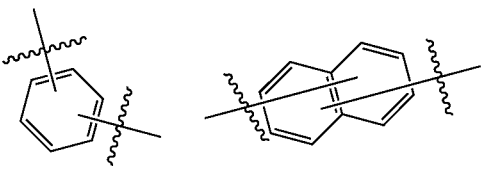

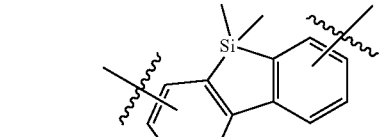

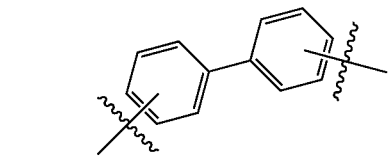

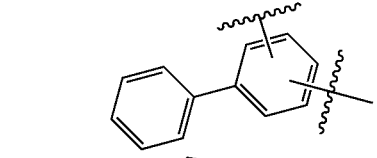

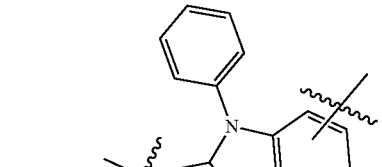

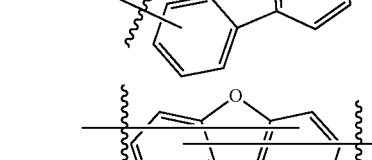

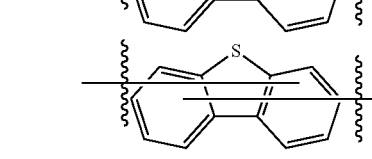

-continued

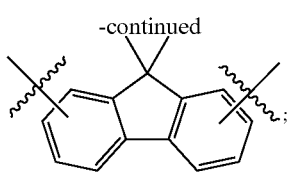

the substituted group $V_2$ has one or two or more substituents, and the substituents in the substituted group $V_2$ are independently selected from deuterium, fluorine, cyano, an alkyl with 1 to 4 carbon atoms, a fluoroalkyl with 1 to 4 carbon atoms, a cycloalkyl with 5 to 10 carbon atoms, a trialkylsilyl with 3 to 7 carbon atoms, an aryl with 6 to 12 carbon atoms, triphenylsilyl, an alkoxy with 1 to 4 carbon atoms, or an alkylthio with 1 to 4 carbon atoms. If the number of substituents in the substituted groups $V_2$ is greater than 1, each substituent may be the same or different.

According to one more specific embodiment, L is selected from single bond, or the following groups:

-continued

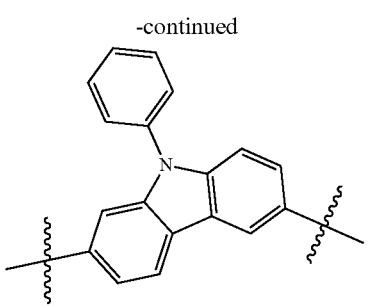

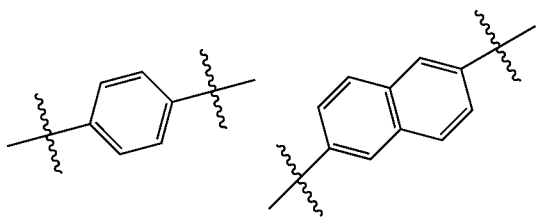

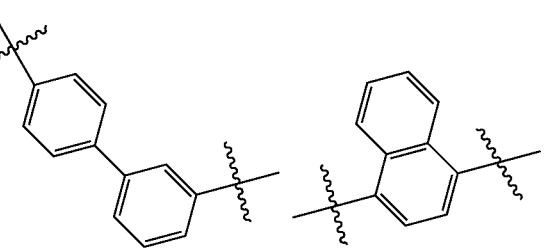

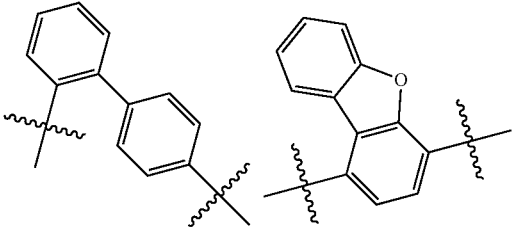

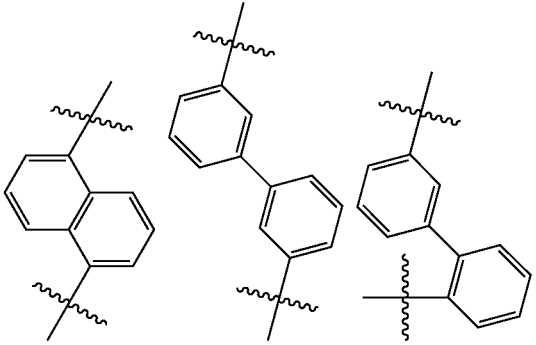

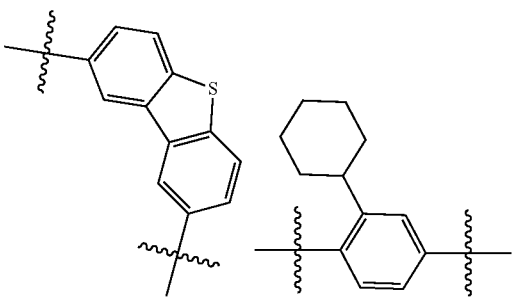

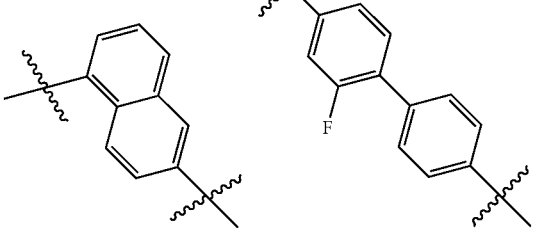

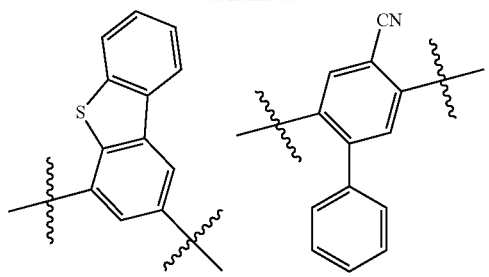
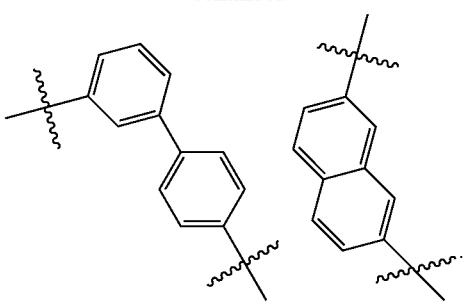
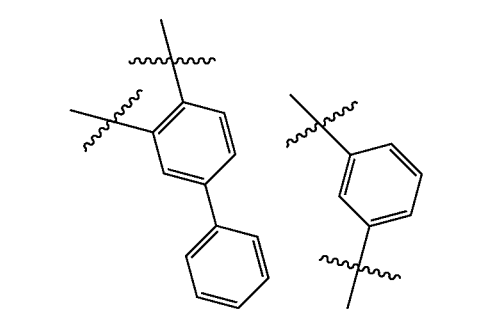
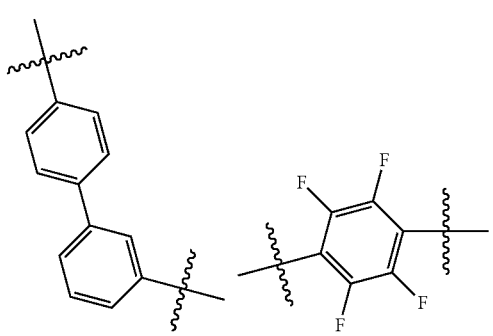
Alternatively, in formula 1,
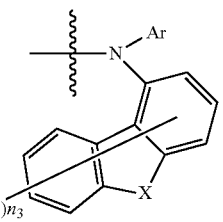
is selected from the following structures:
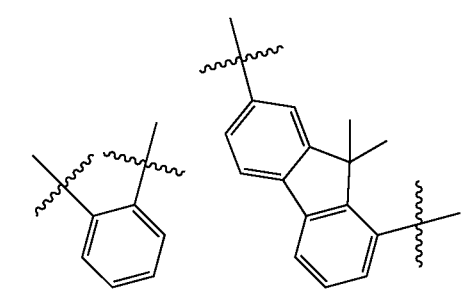
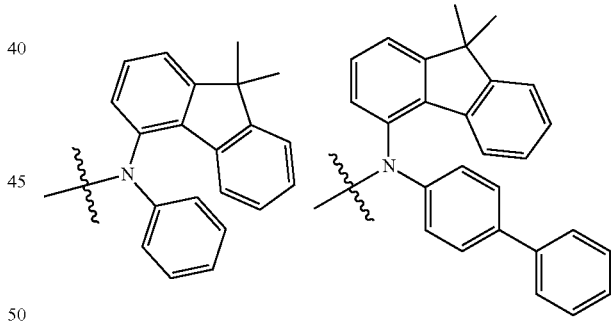
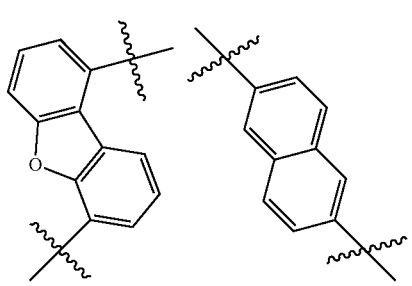
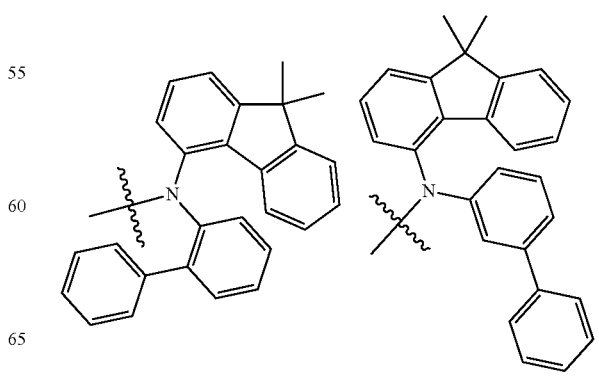

-continued

-continued
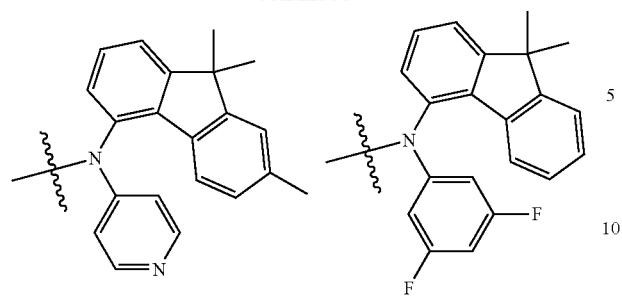
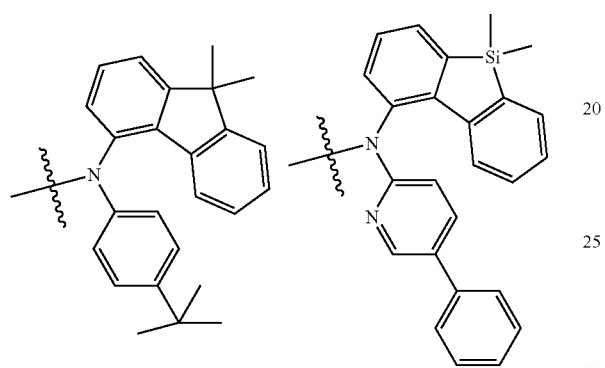
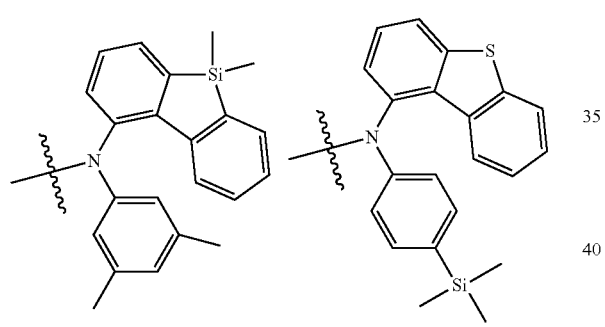
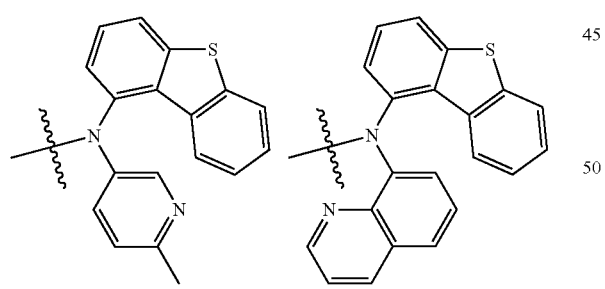
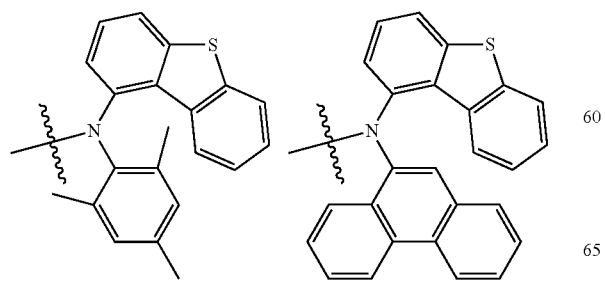
-continued
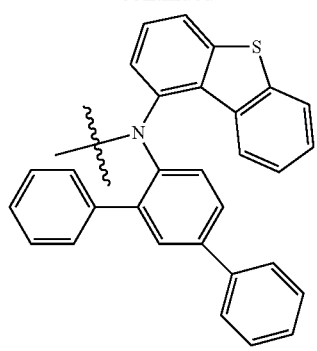
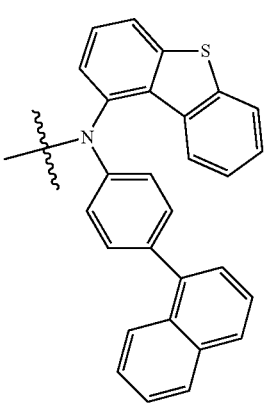
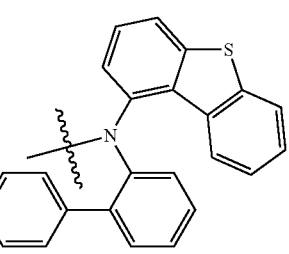
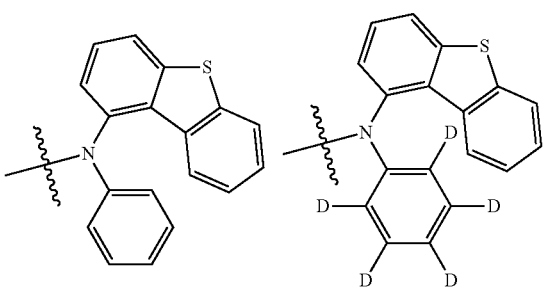
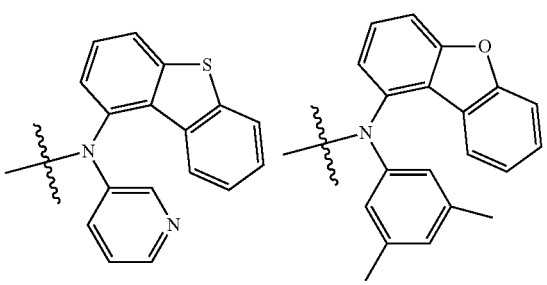

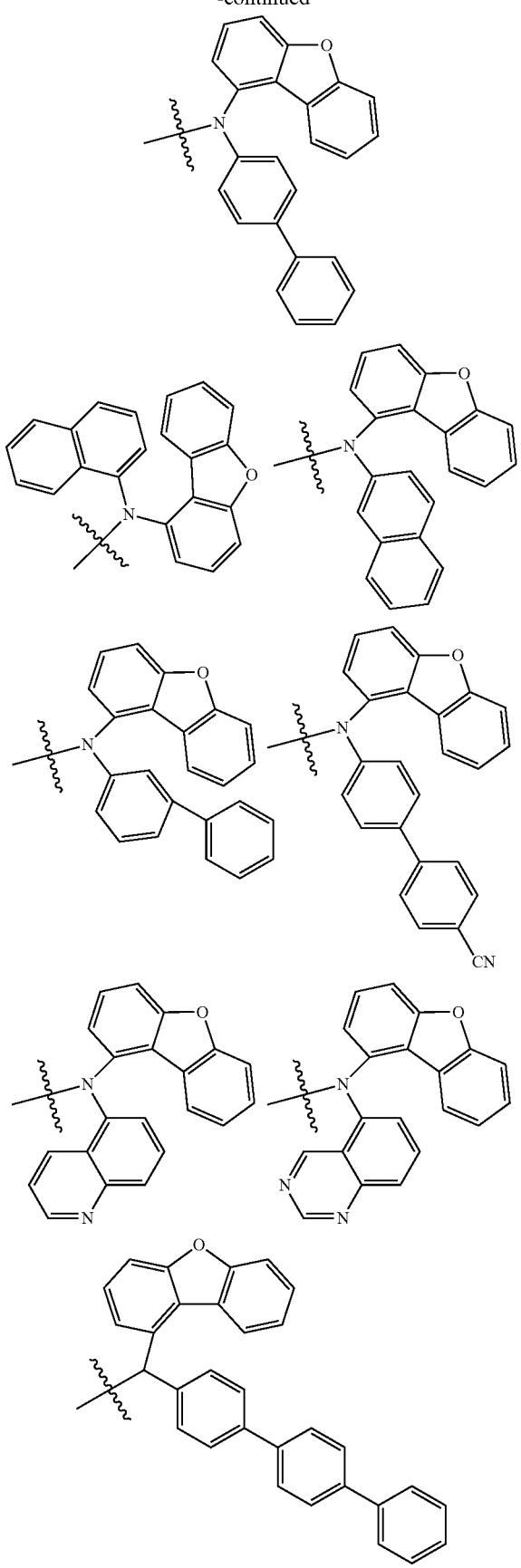
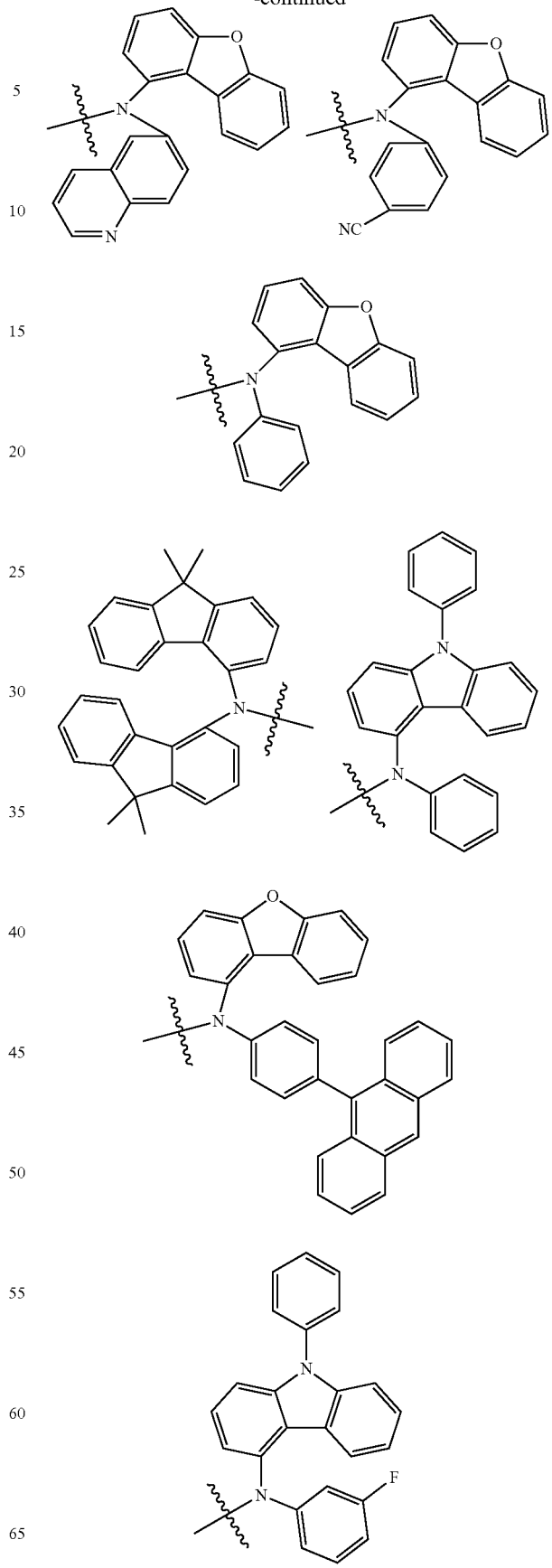

-continued
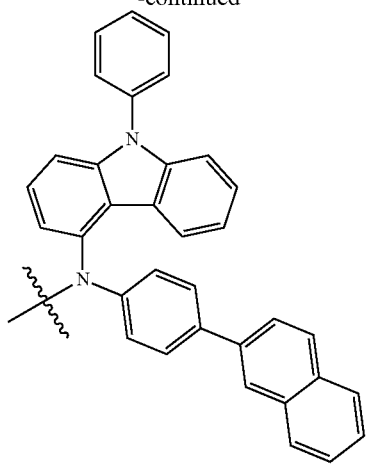
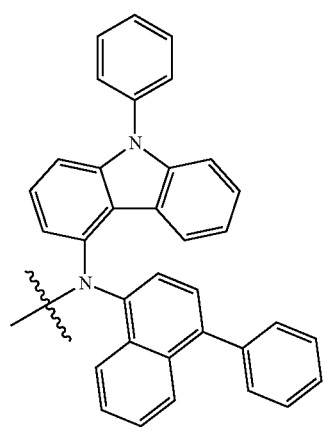
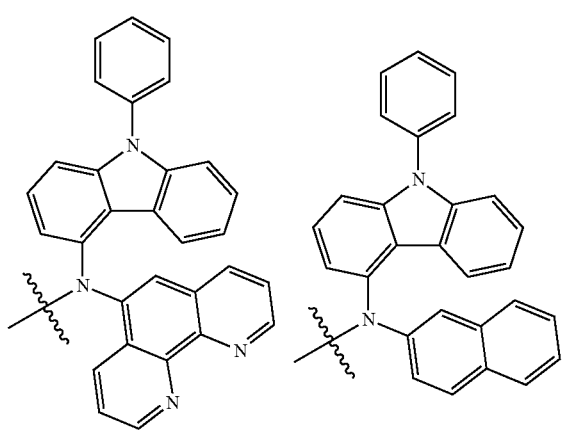
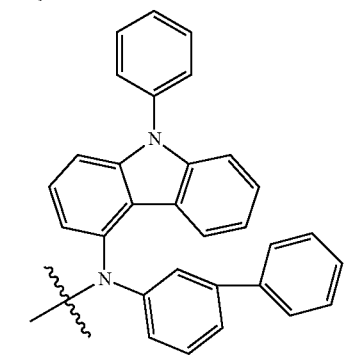
-continued
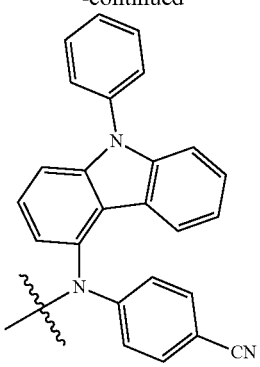
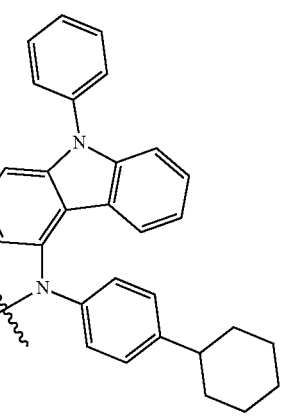
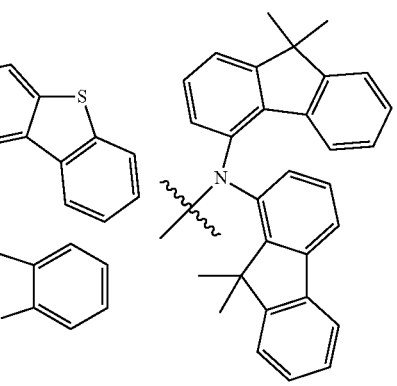
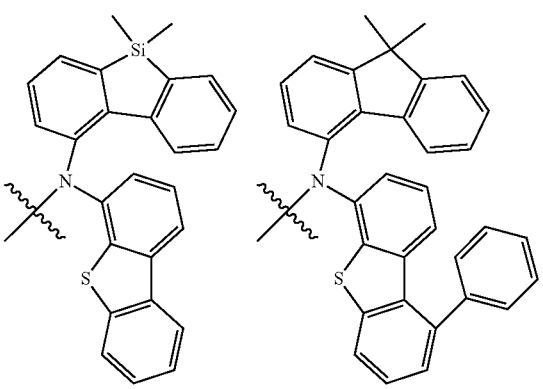

-continued
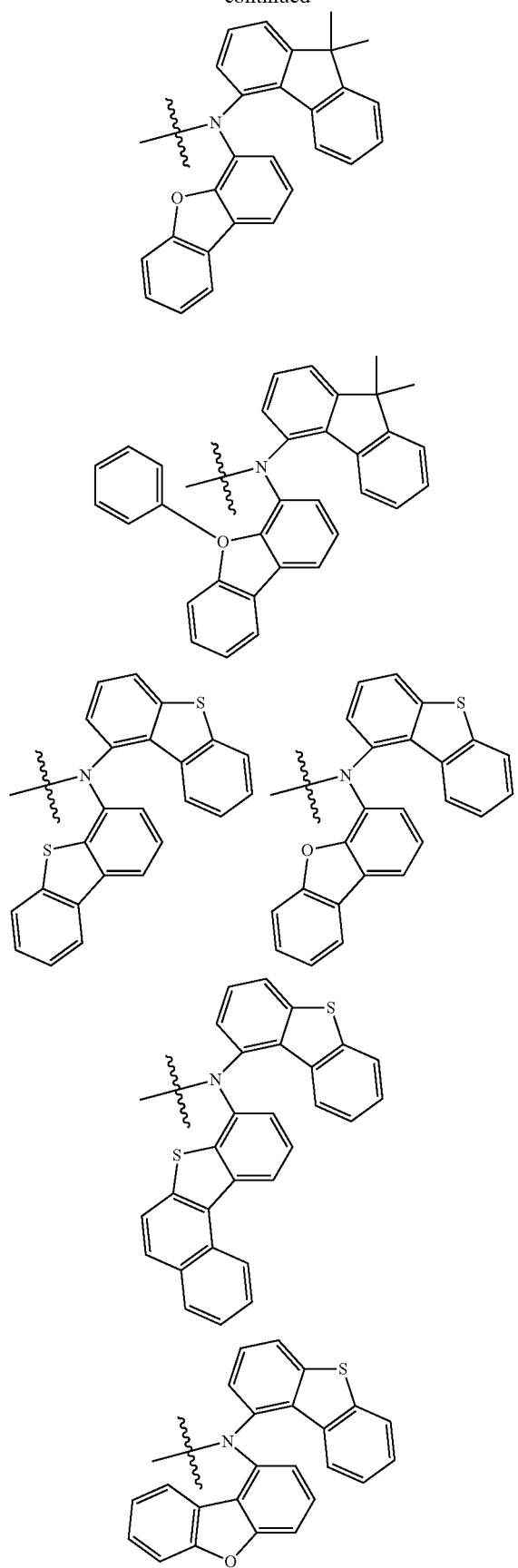
-continued
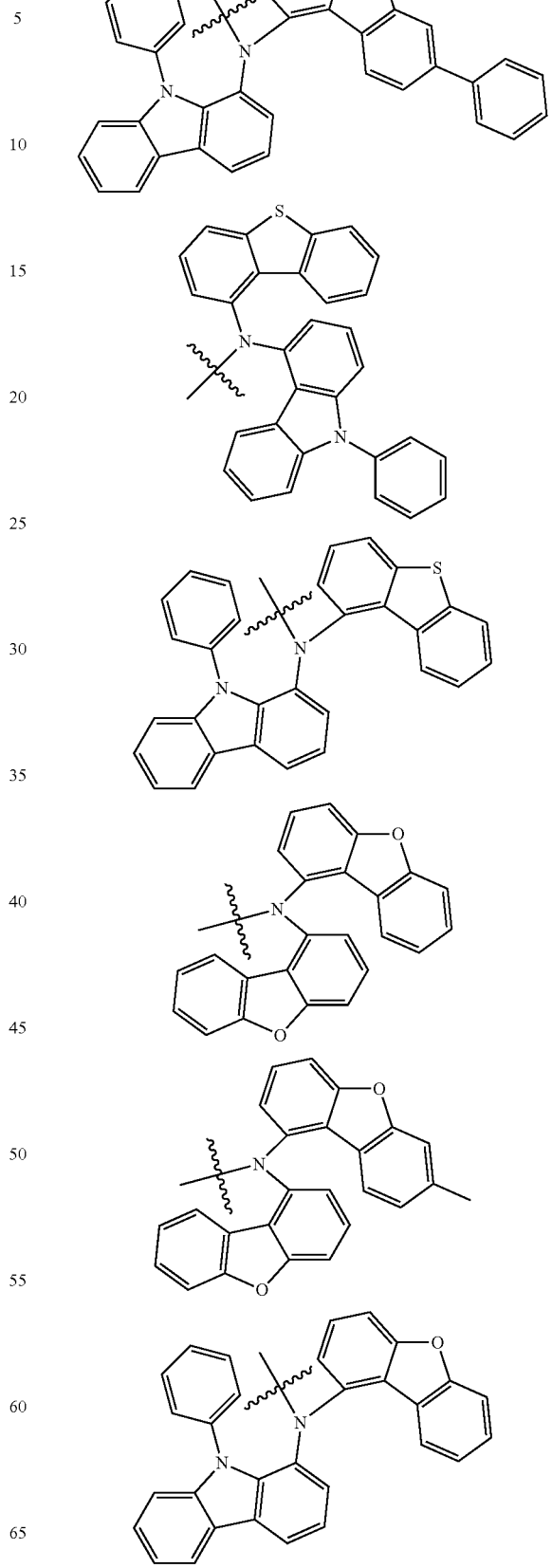

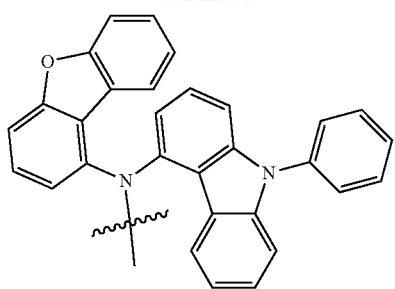
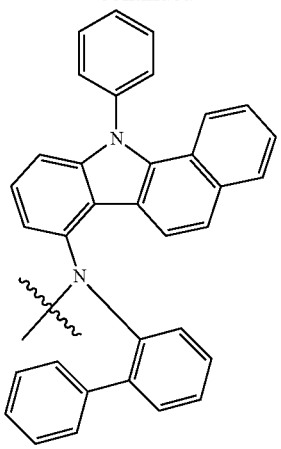
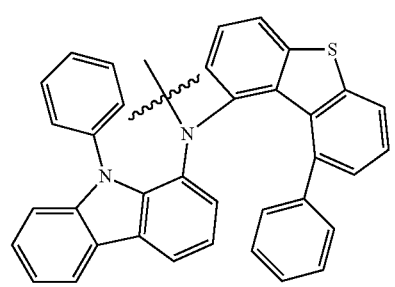
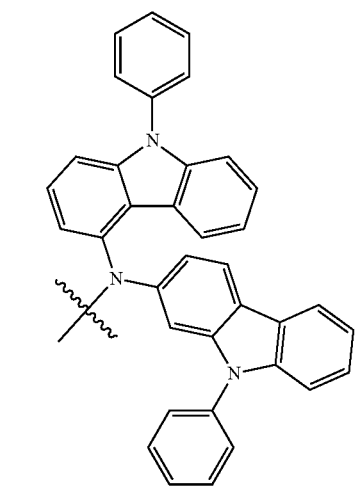
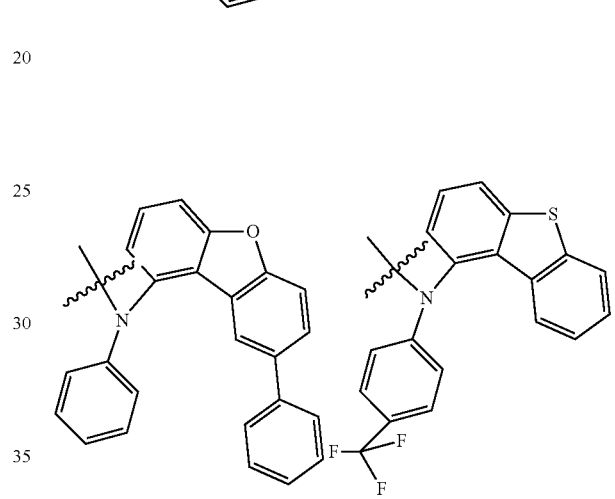
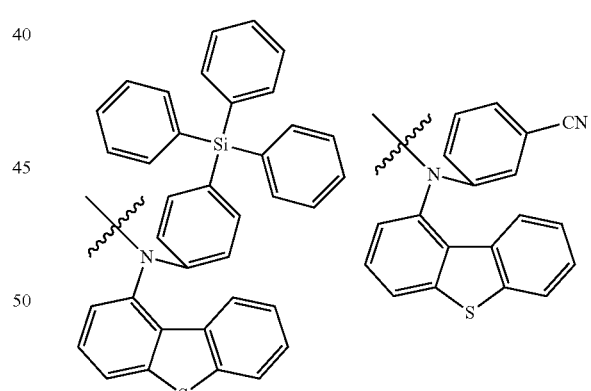
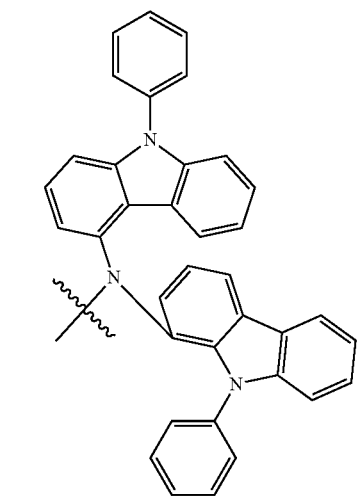
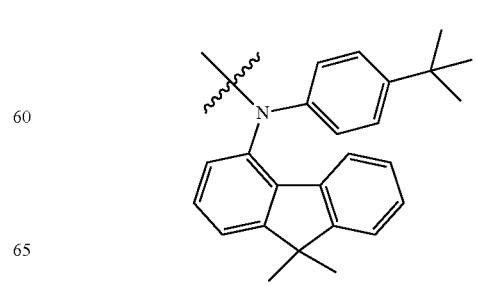

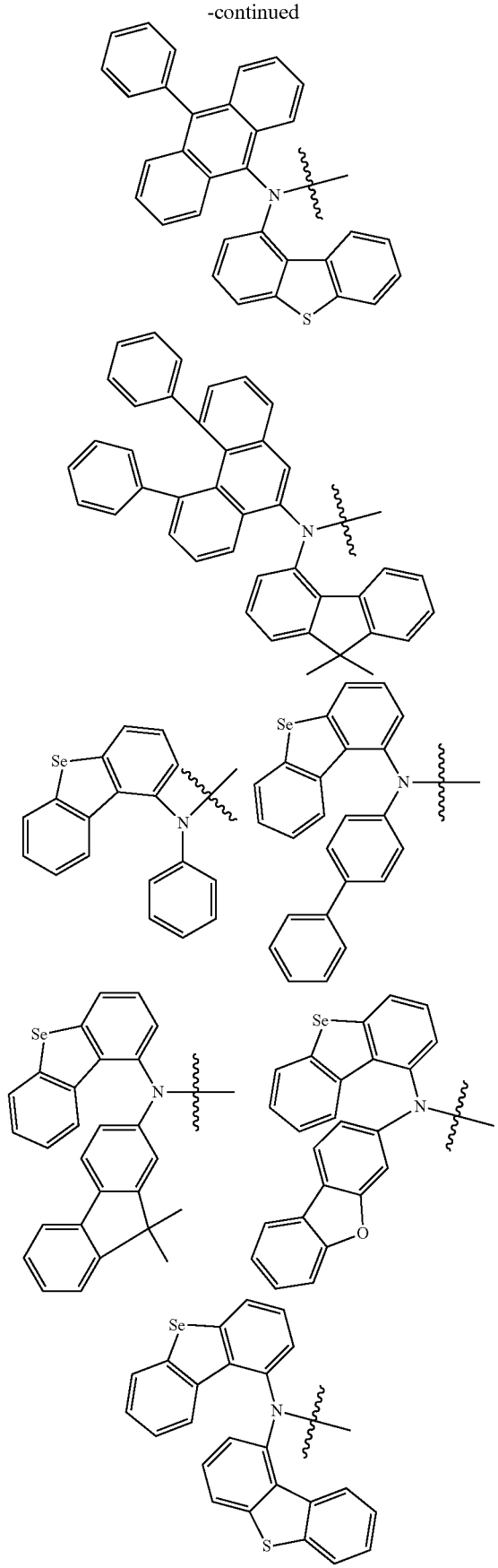
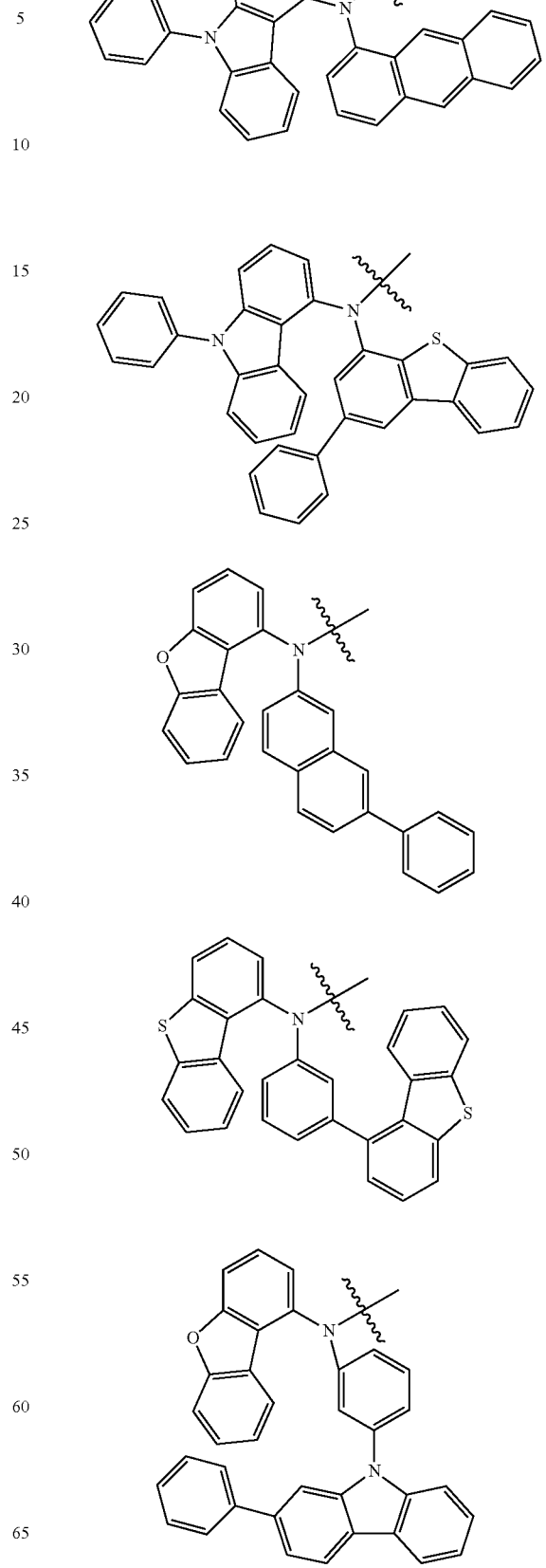

-continued
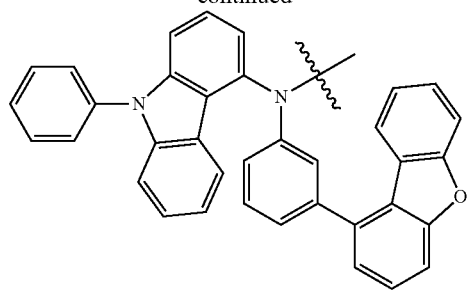
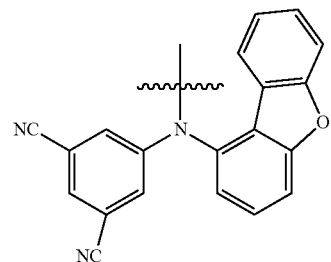
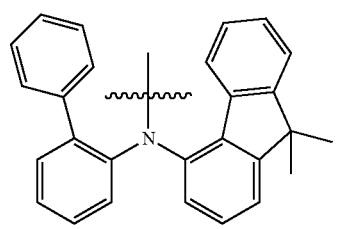
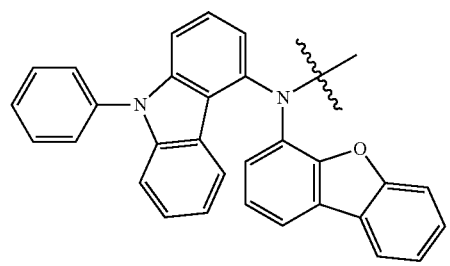
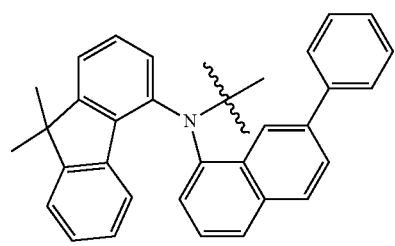
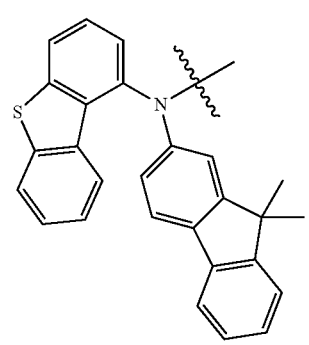
-continued
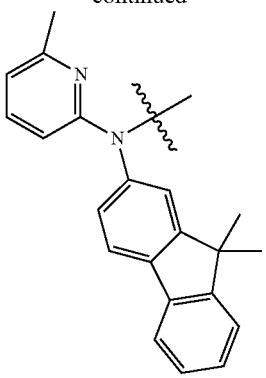
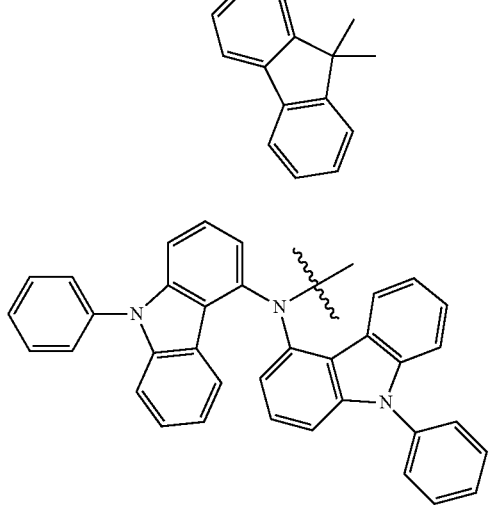
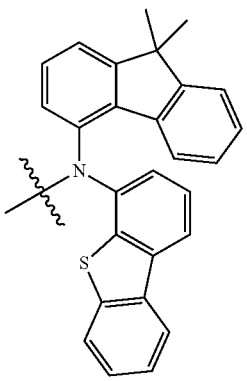
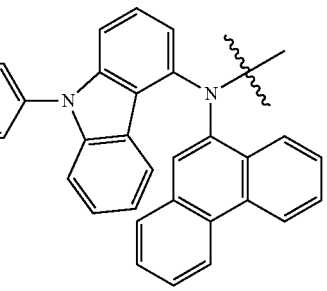
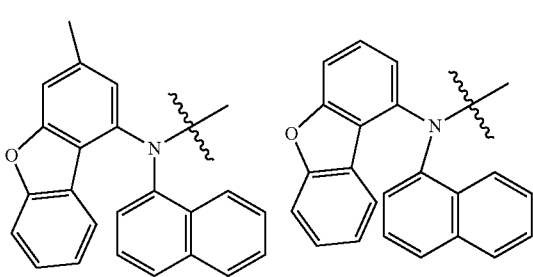

49
-continued
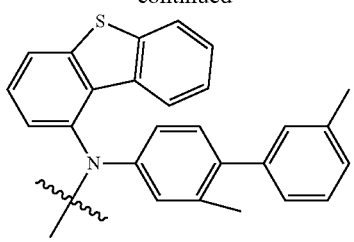
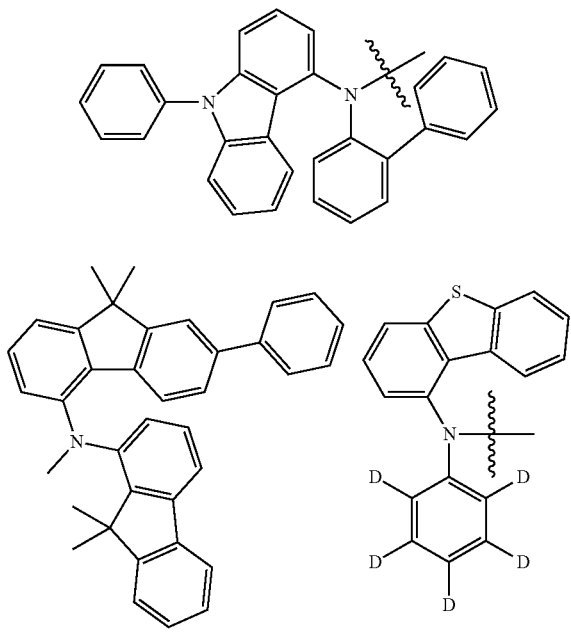
50
Further alternatively,
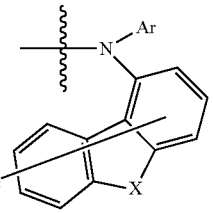
has a structure as follows:
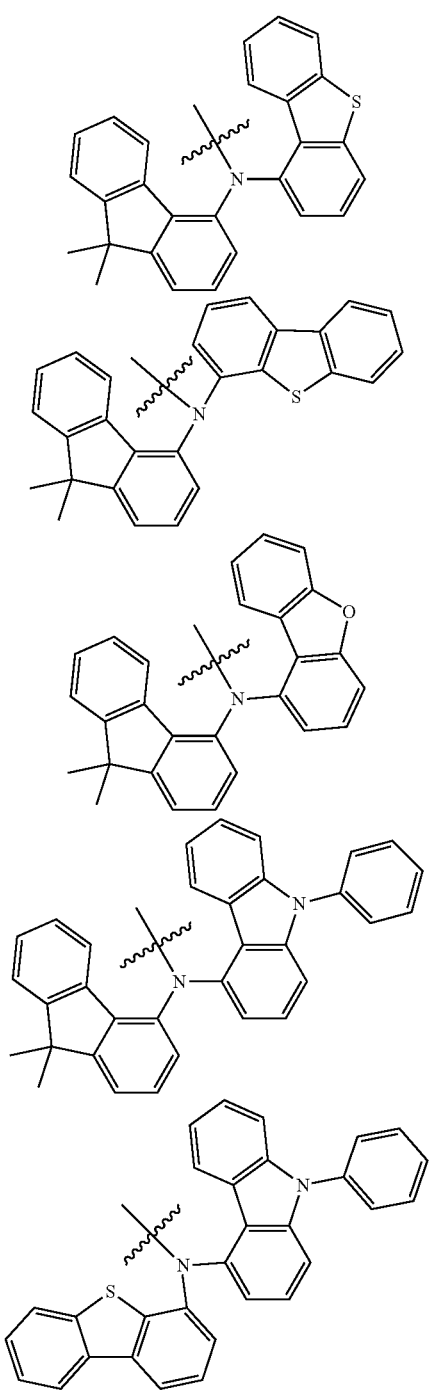

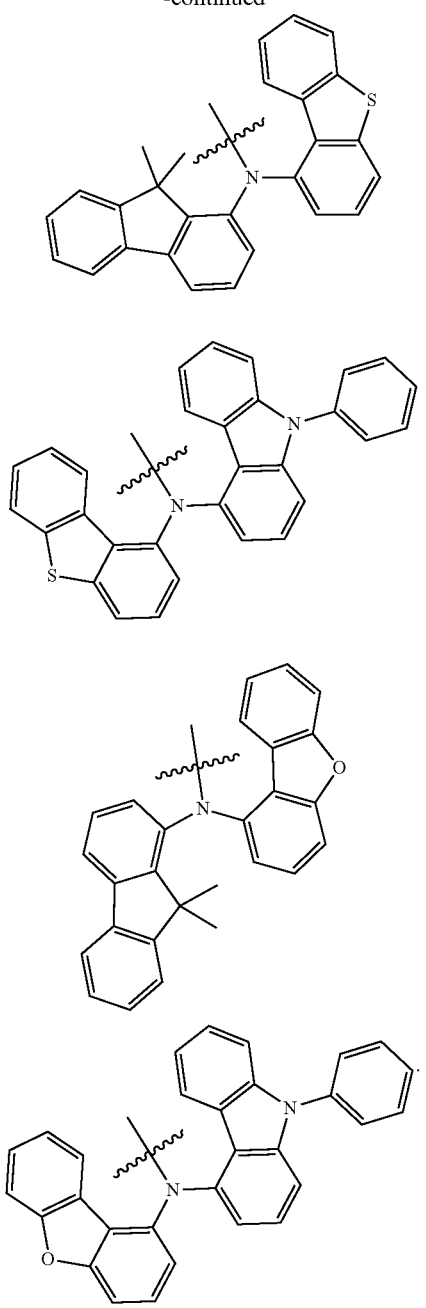
Alternatively, the nitrogen-containing compound is selected from the following compounds:
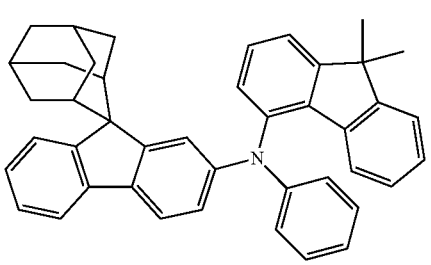
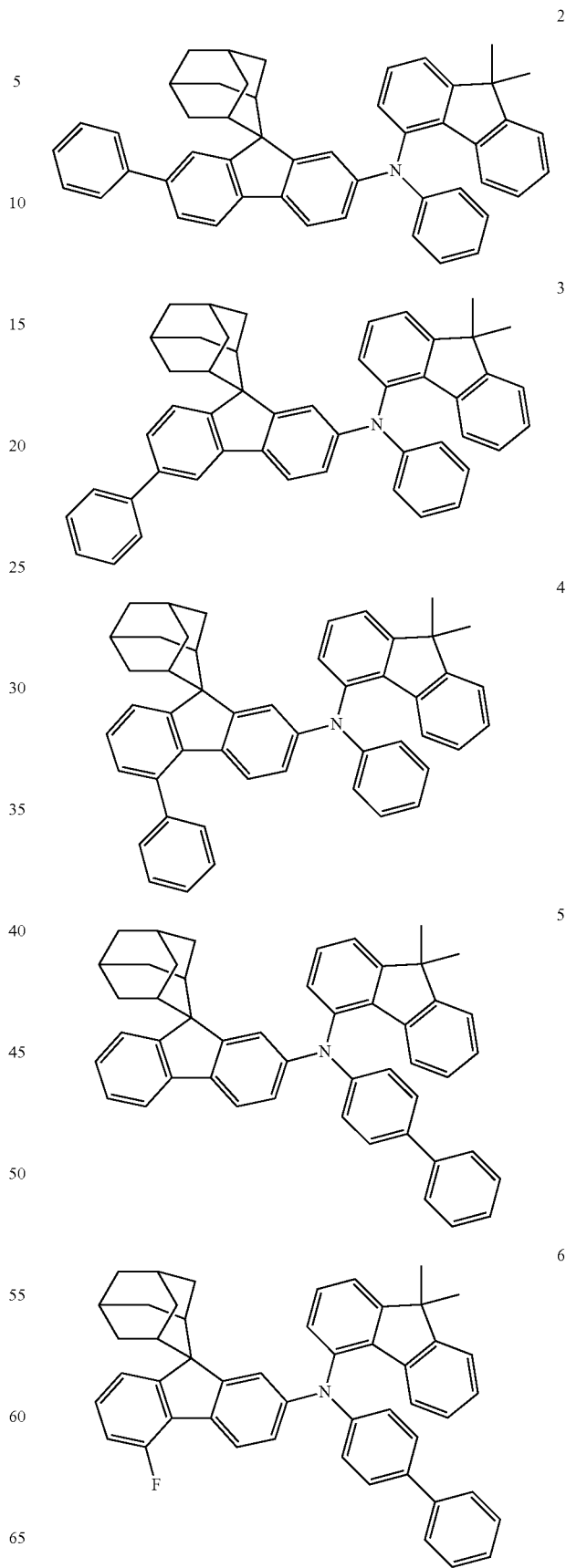

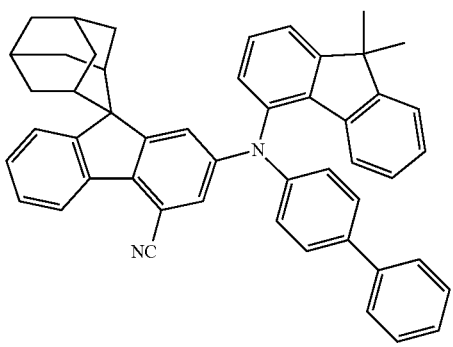
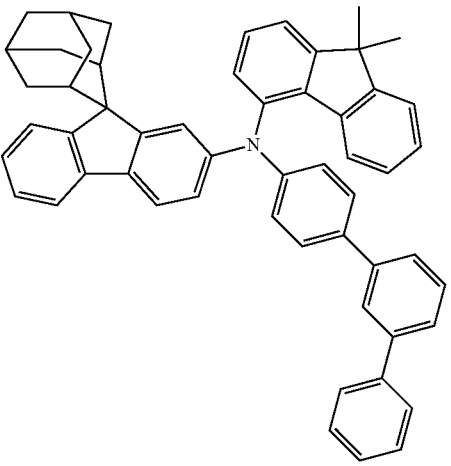
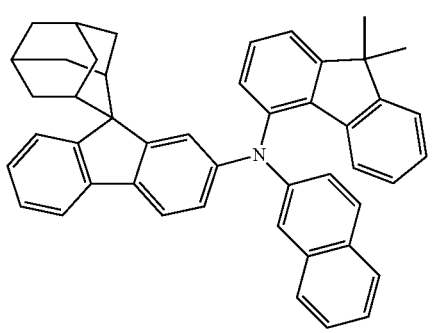
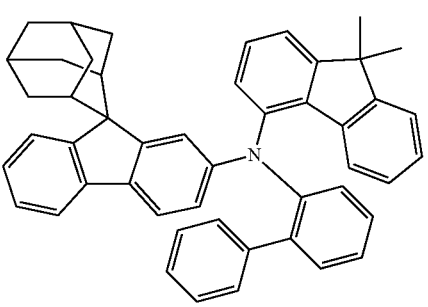
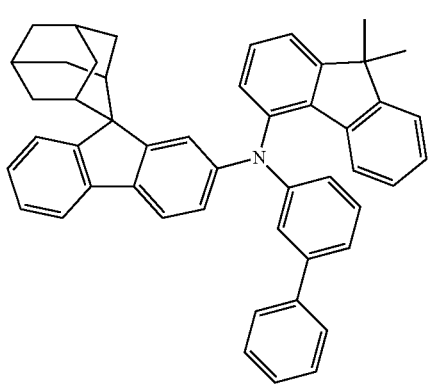
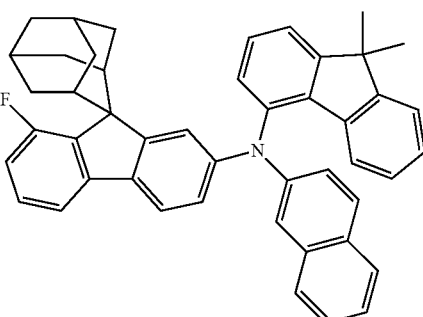
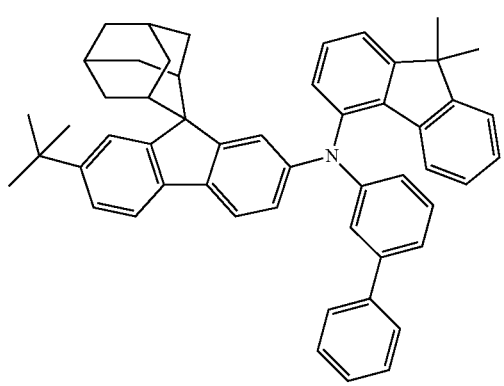
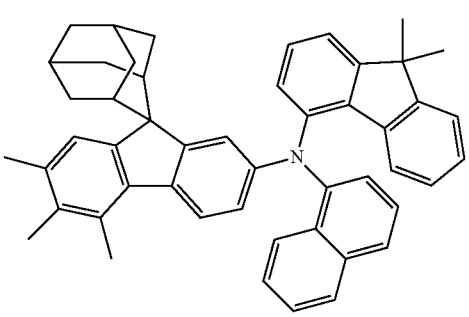

-continued
15
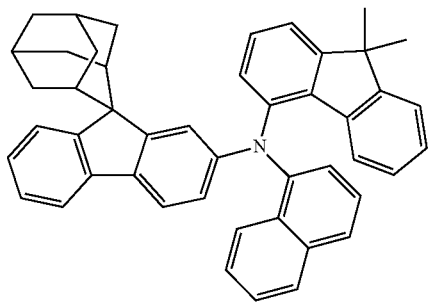
16
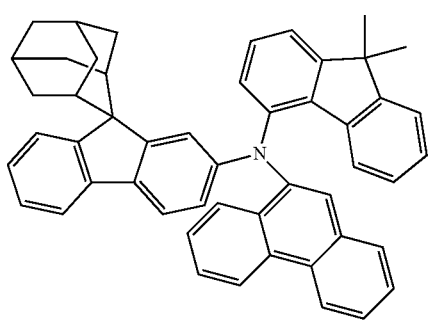
17
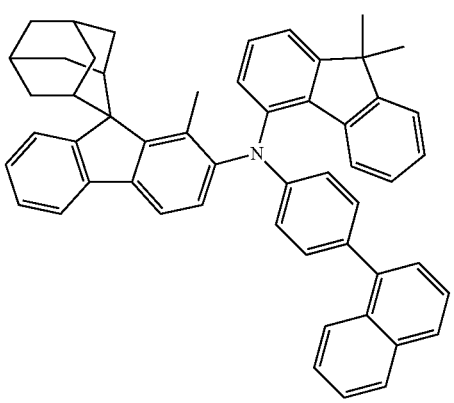
18
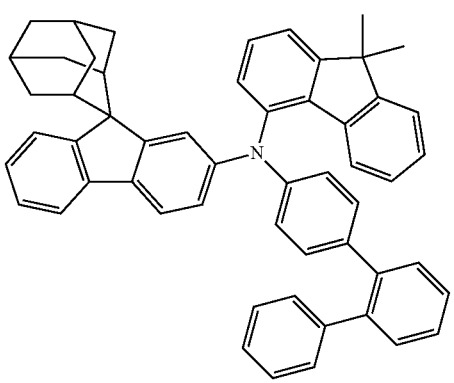
-continued
19
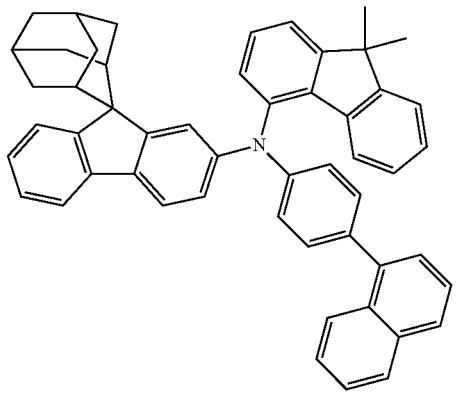
20
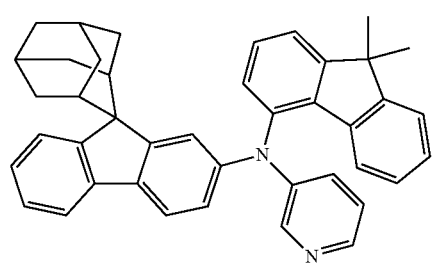
21
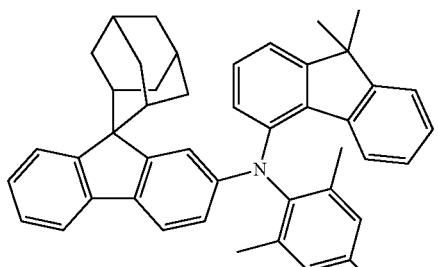
22
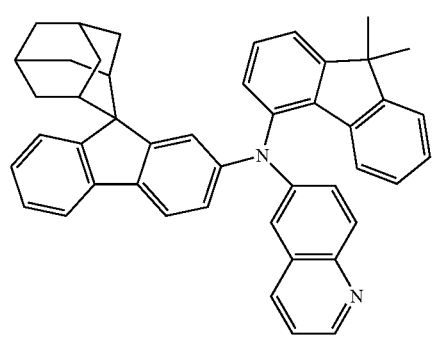
23
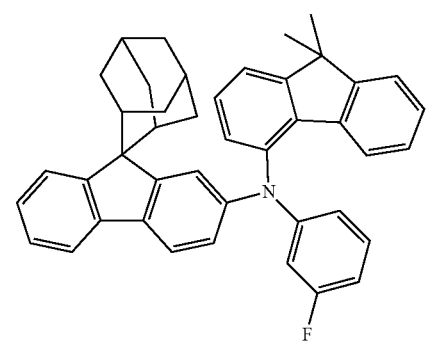

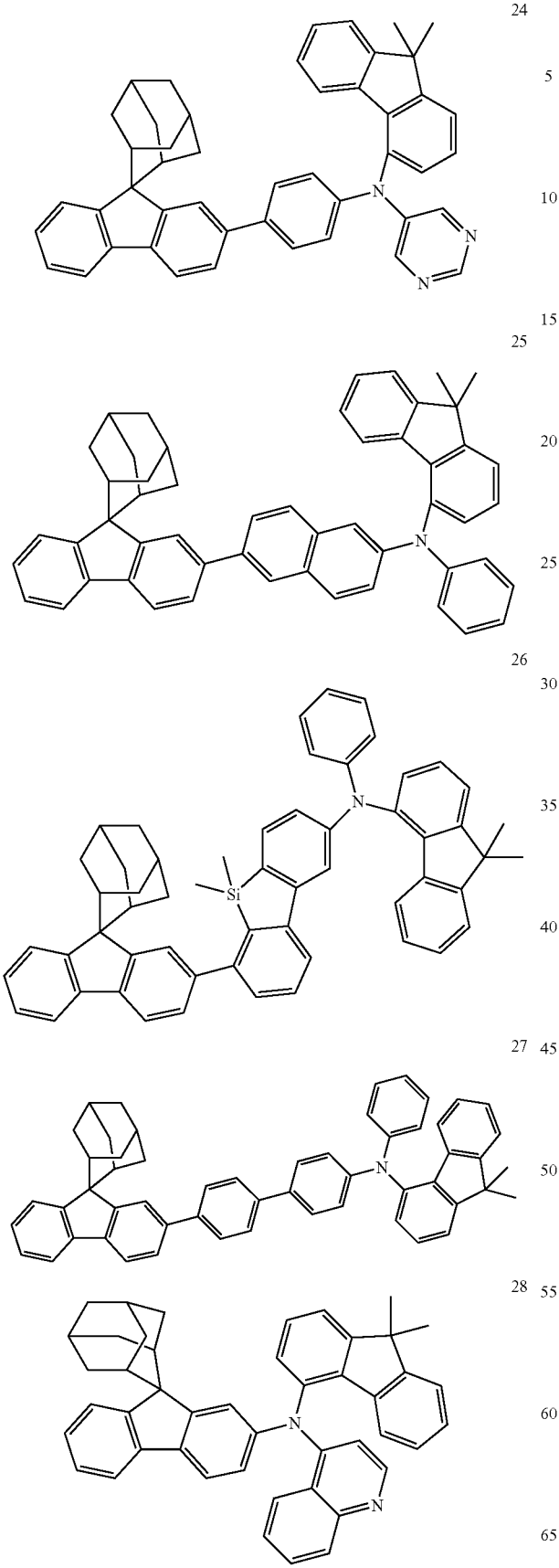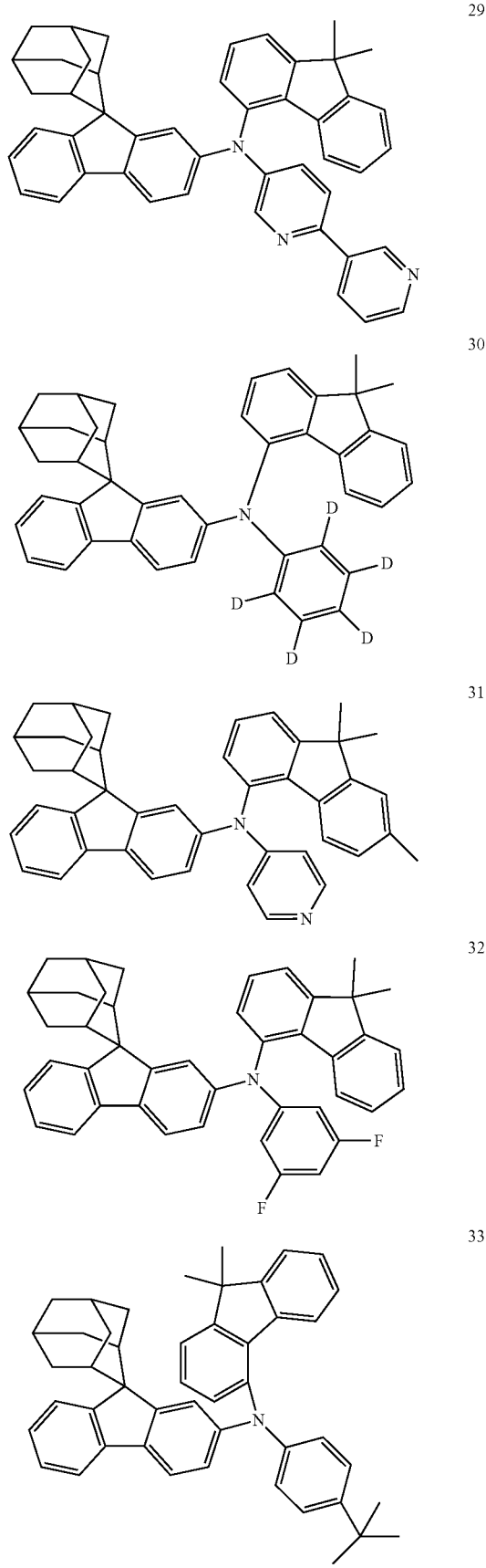

-continued
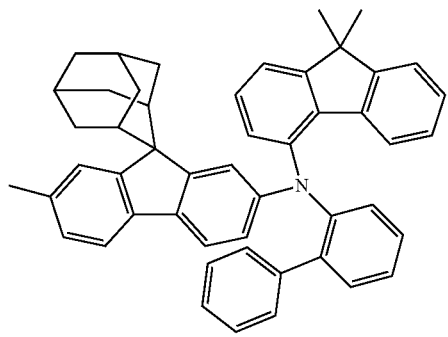
34
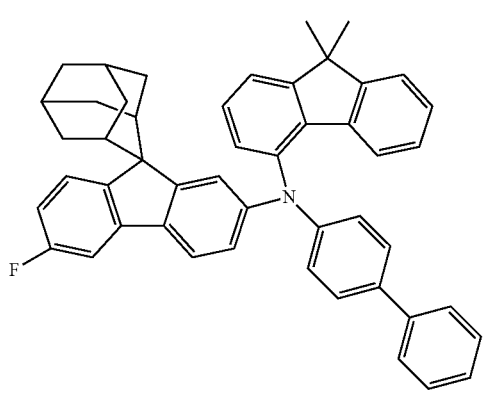
35
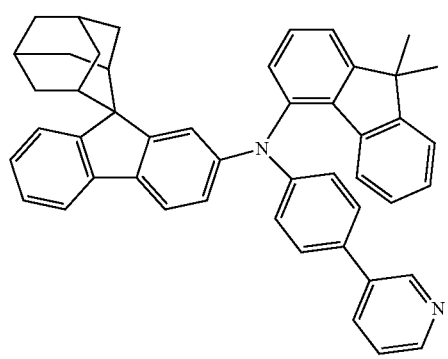
36
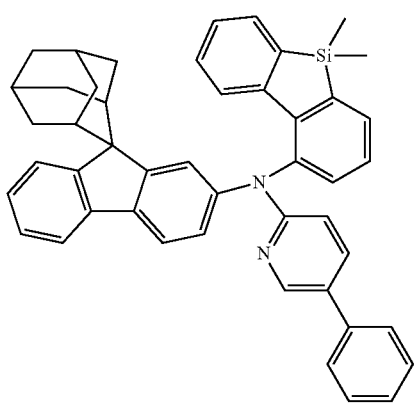
37
-continued
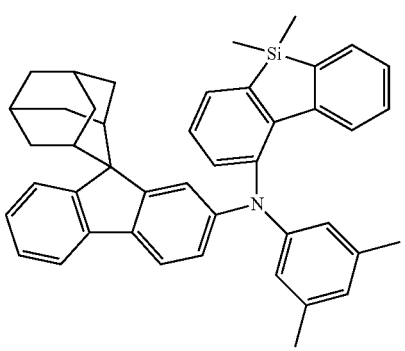
38
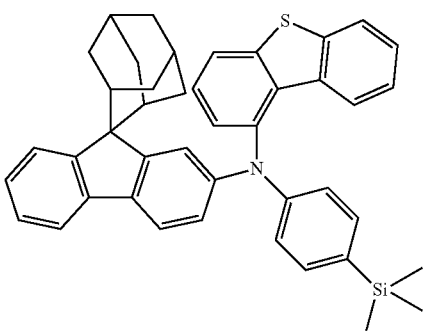
39
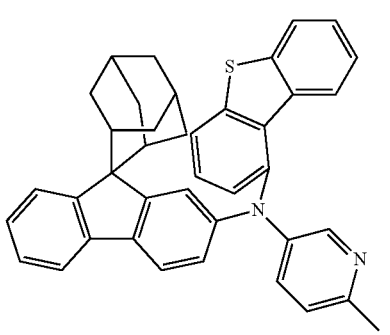
40
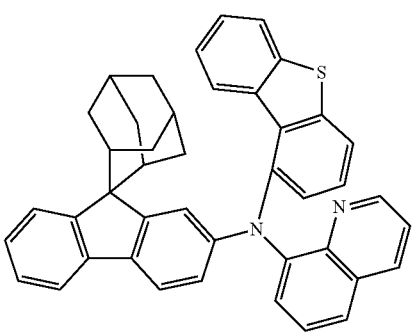
41
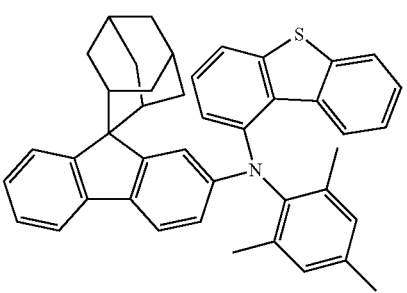
42

43
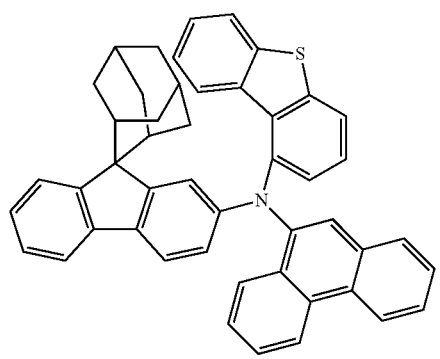
44
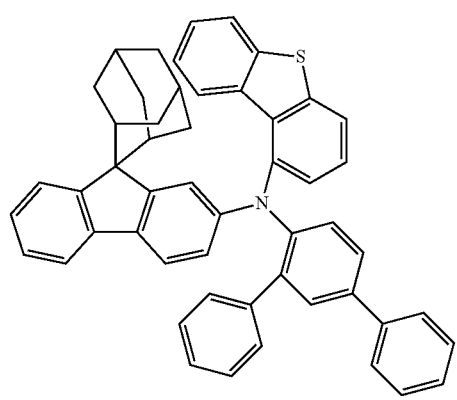
45
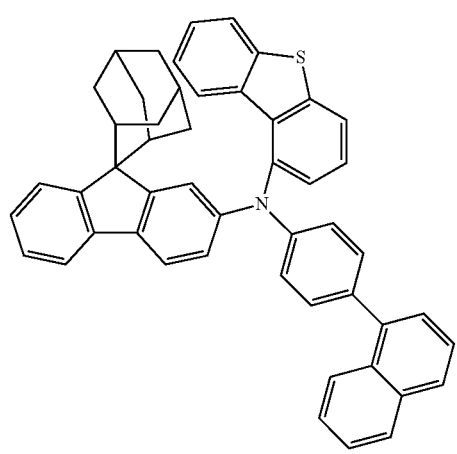
46
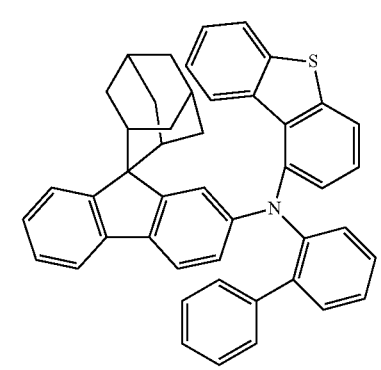
47
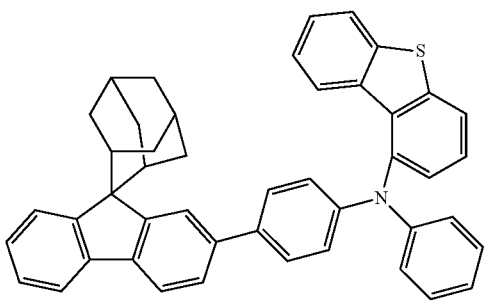
48
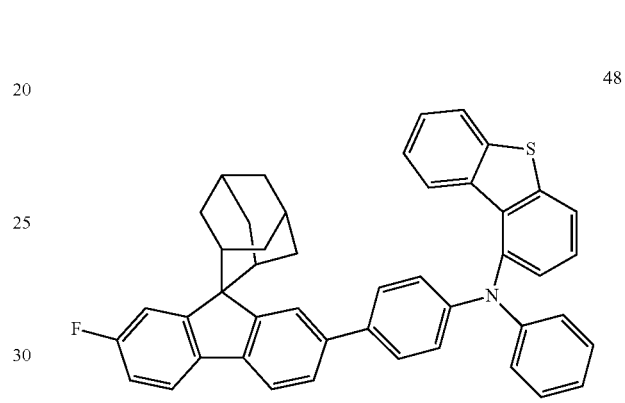
49
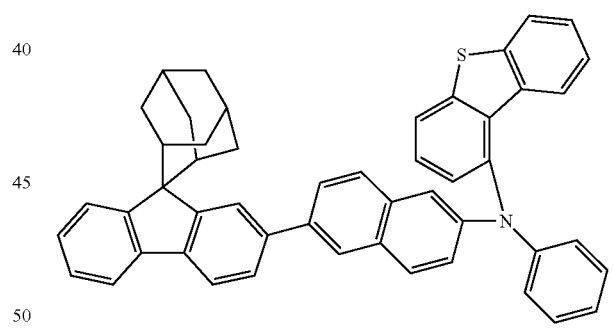
50
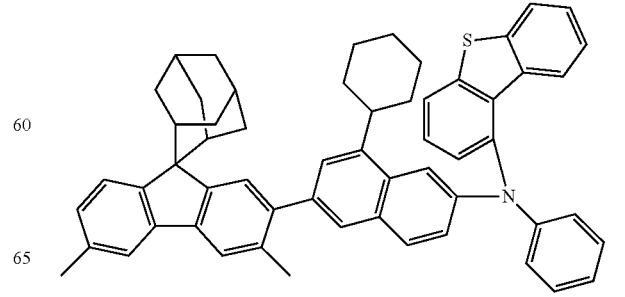

51
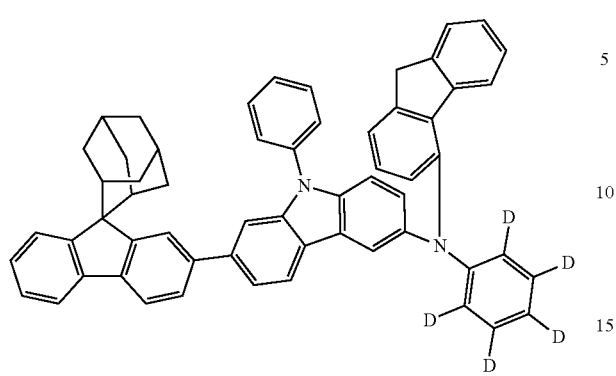
52
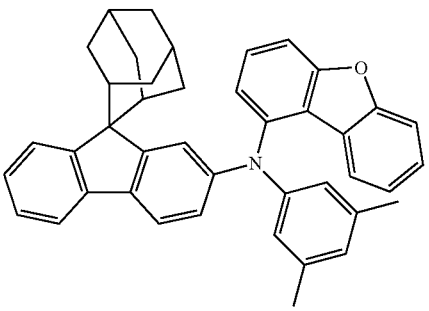
53
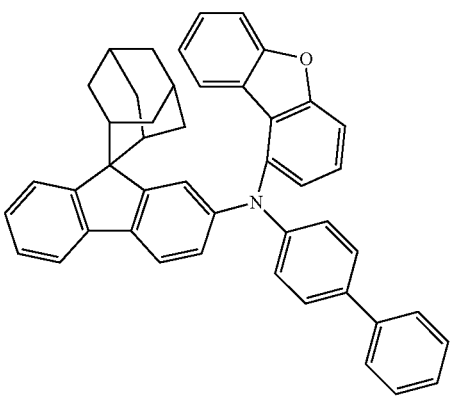
54
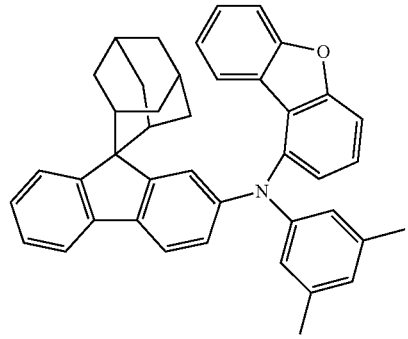
55
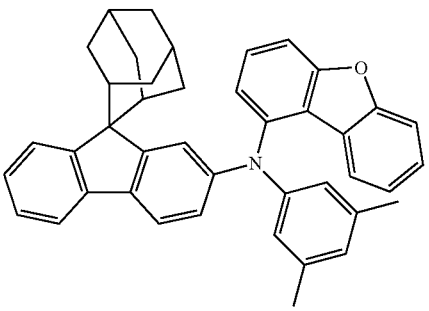
56
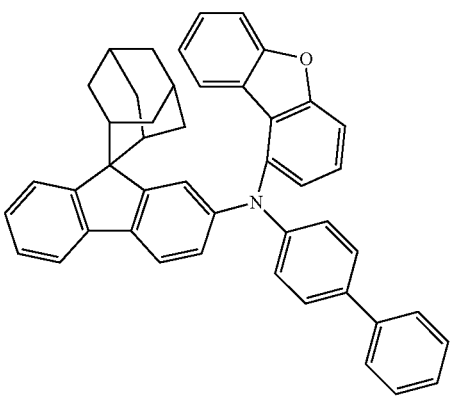
57
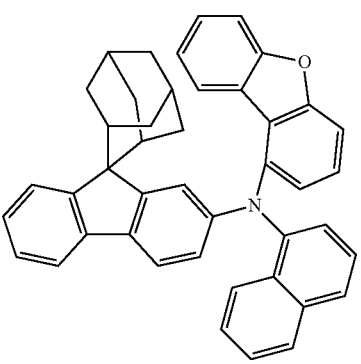
58
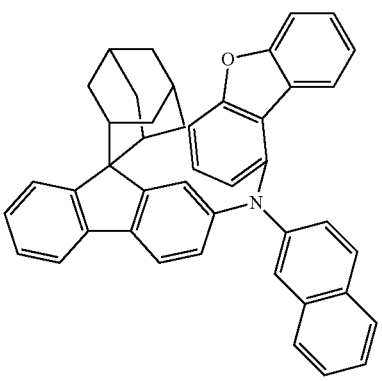

-continued
59
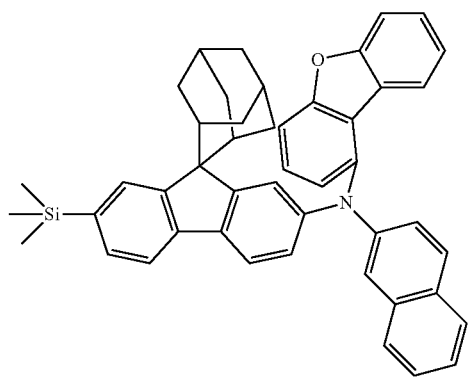
60
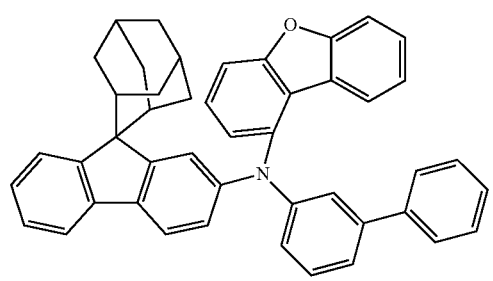
61
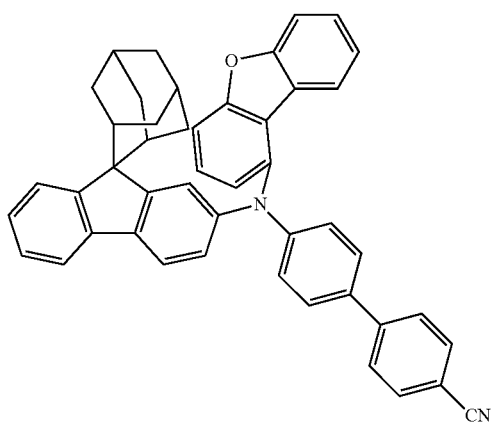
62
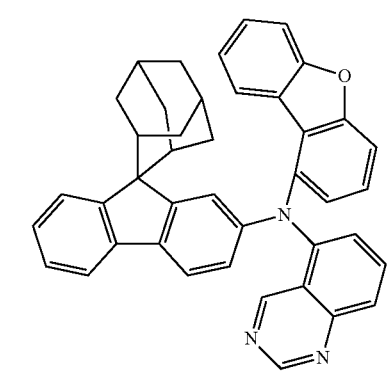
-continued
63
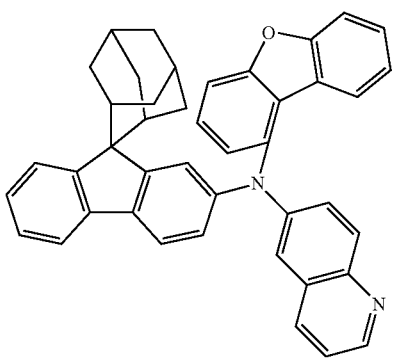
64
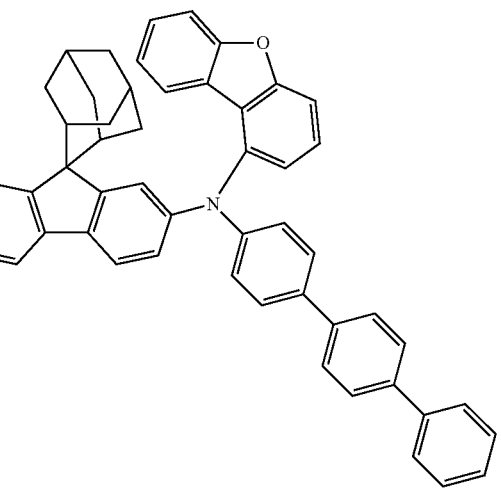
65
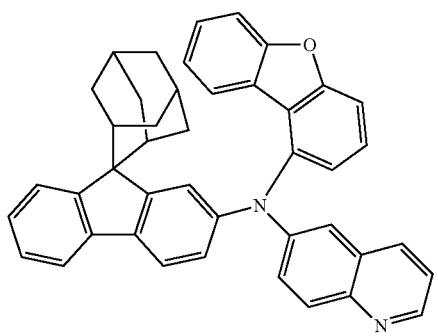
66
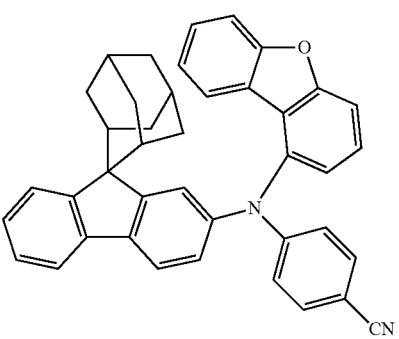

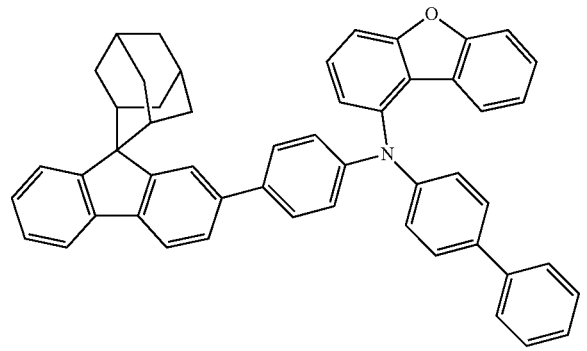
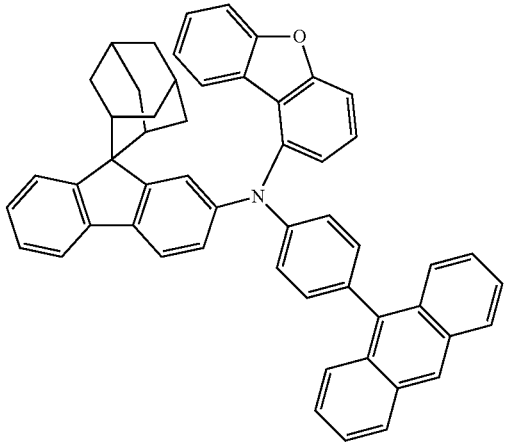
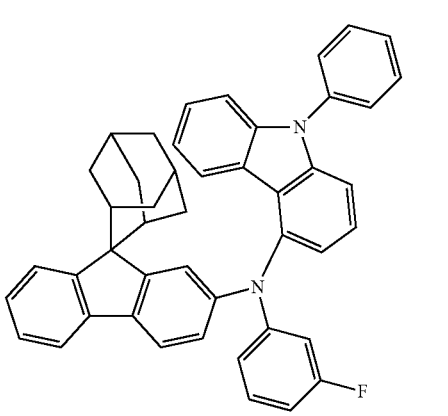
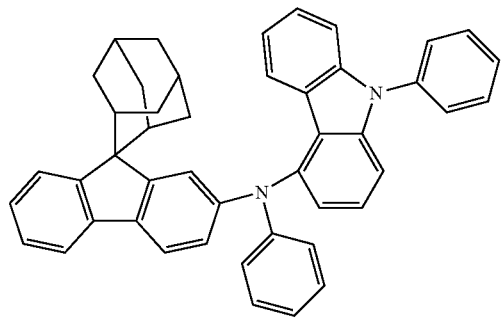
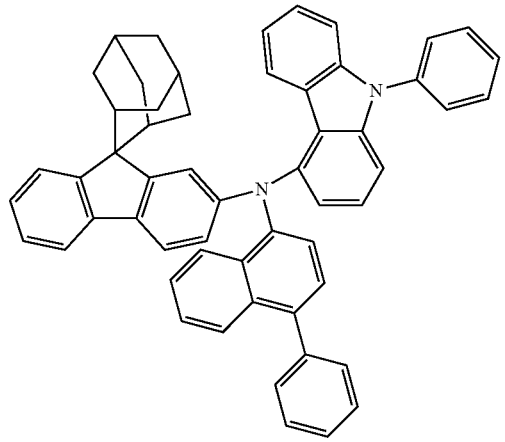

69 70
-continued -continued
75 78
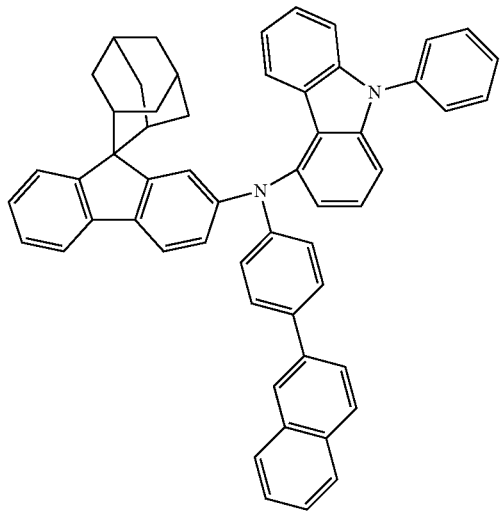
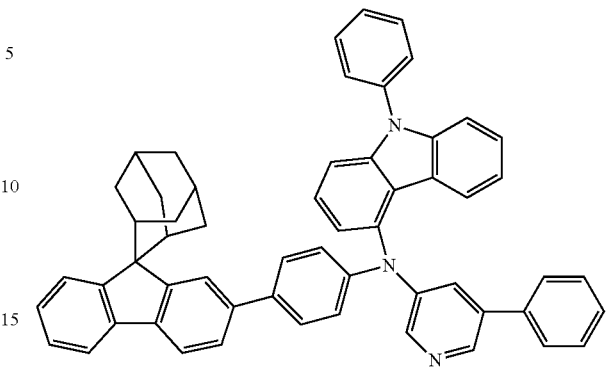
76 79
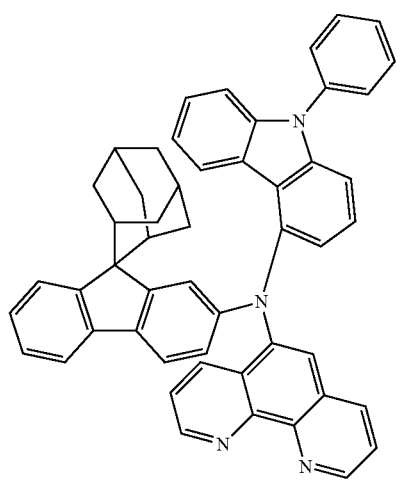
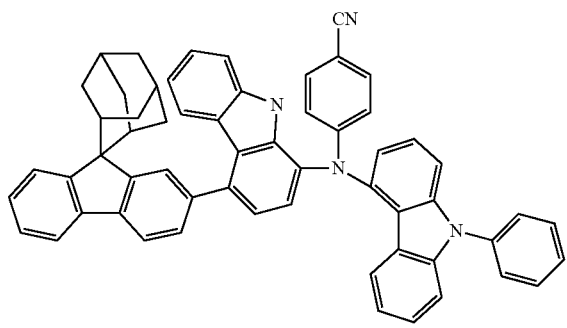
77 80
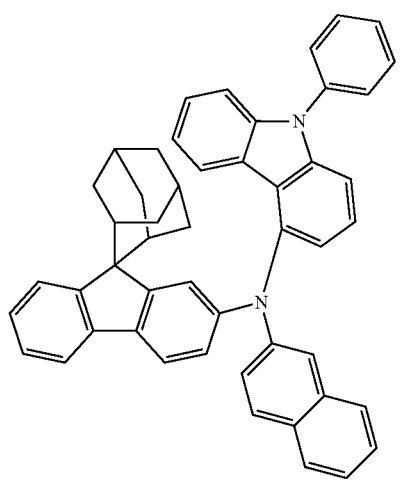
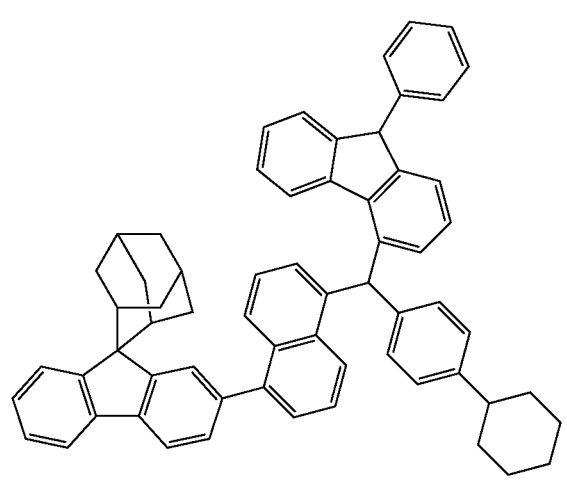

-continued
81
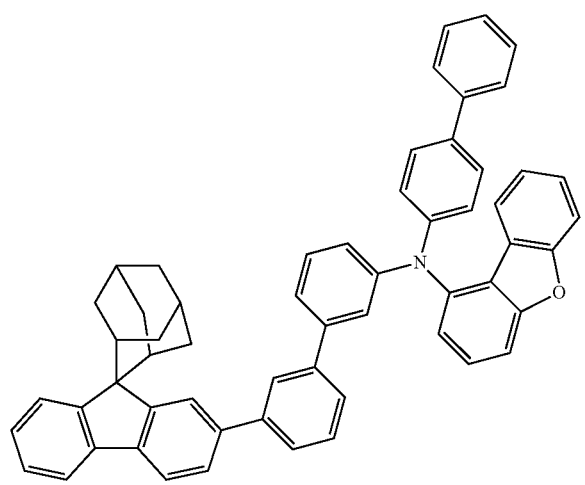
82
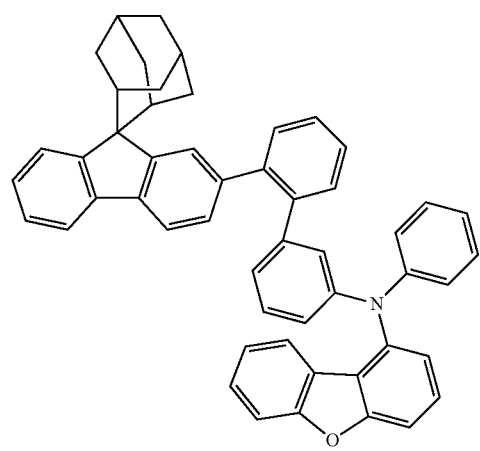
83
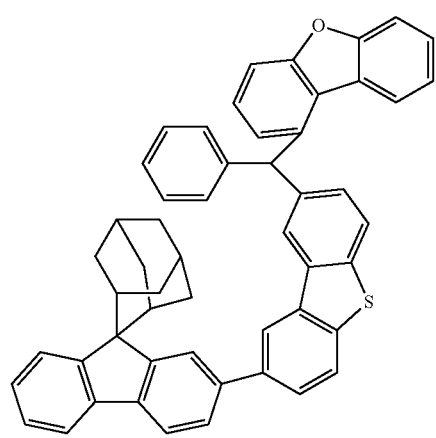
-continued
84
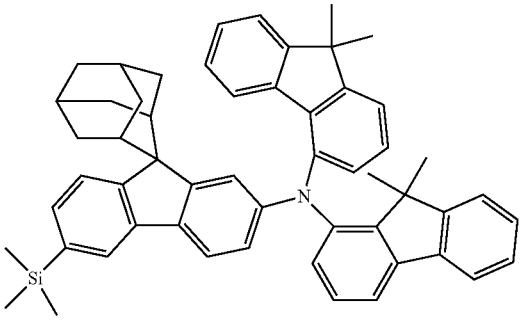
85
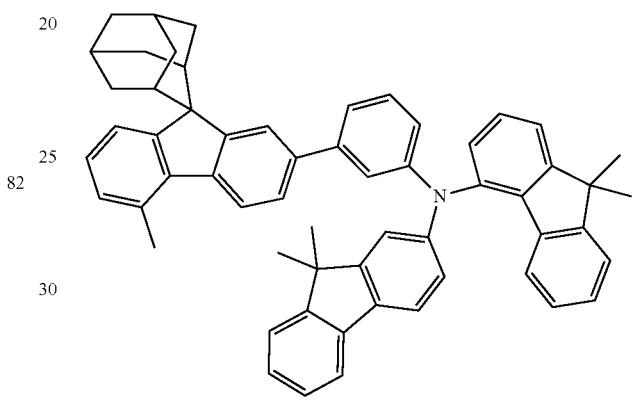
86
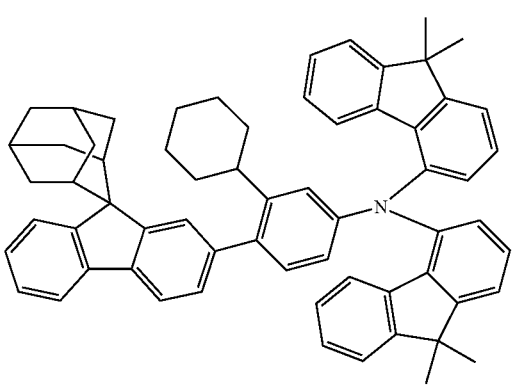
87
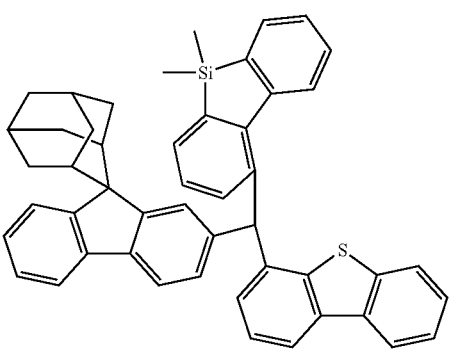

88
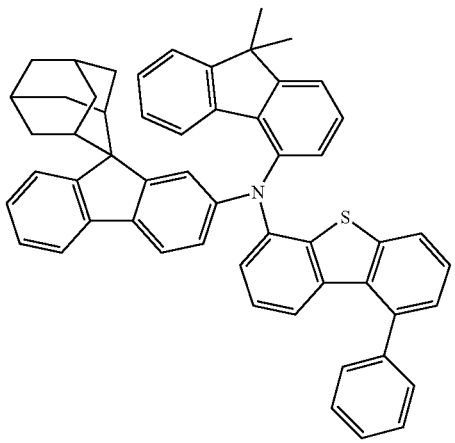
89
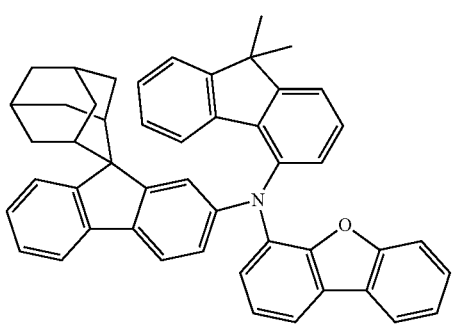
90
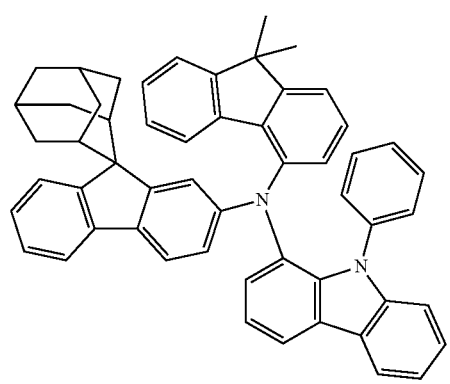
91
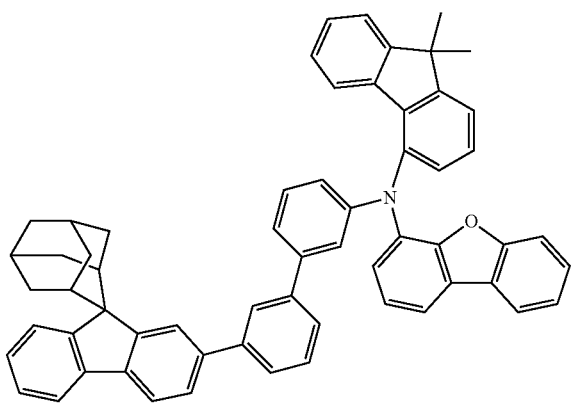
92
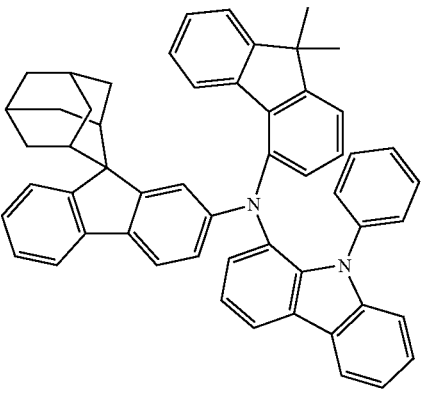
93
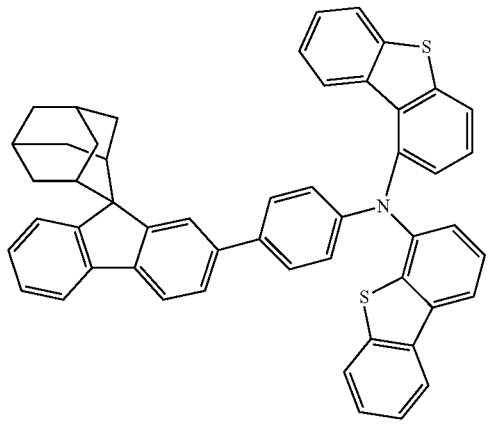
94
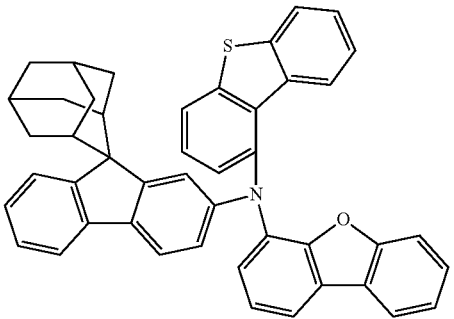
95
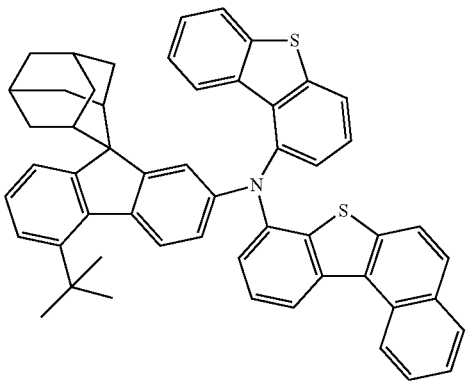

96
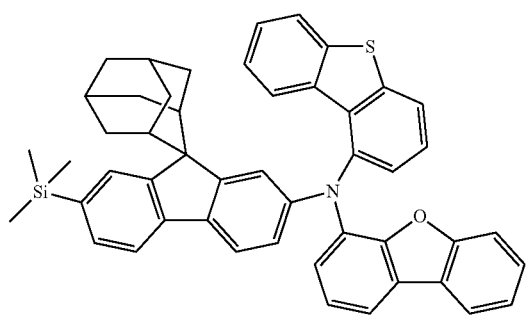
97
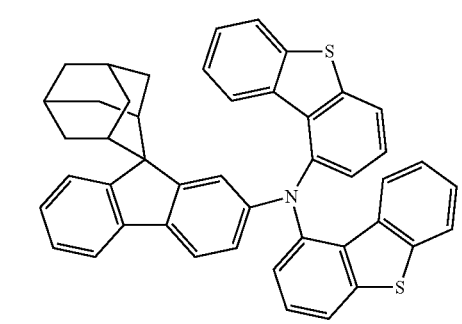
98
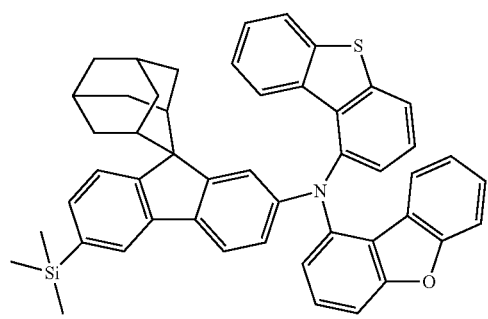
99
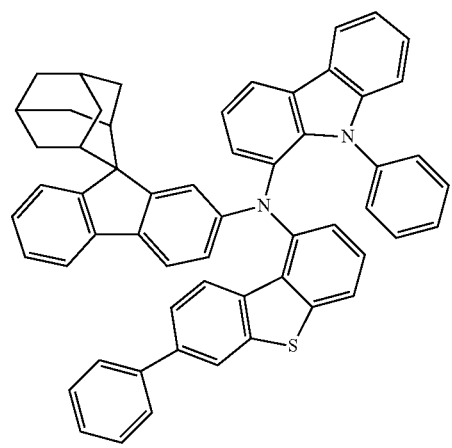
100
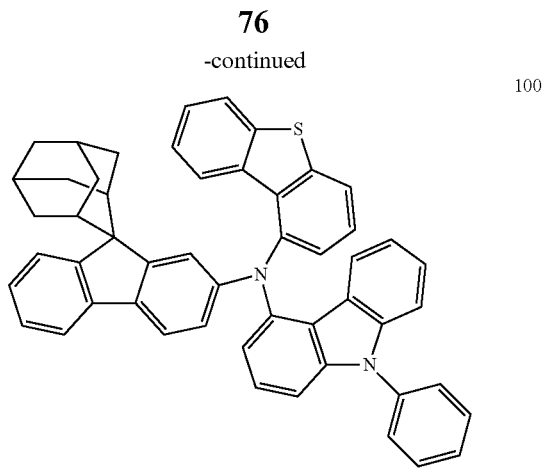
101
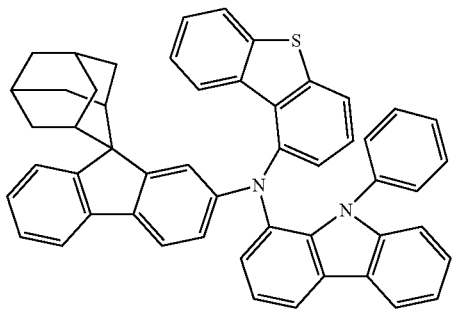
102
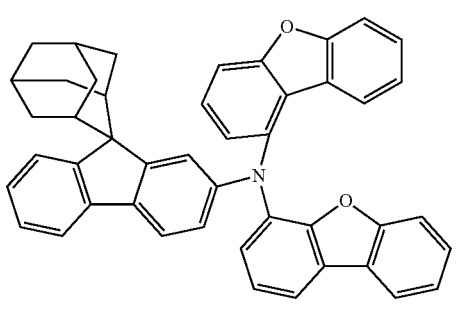
103
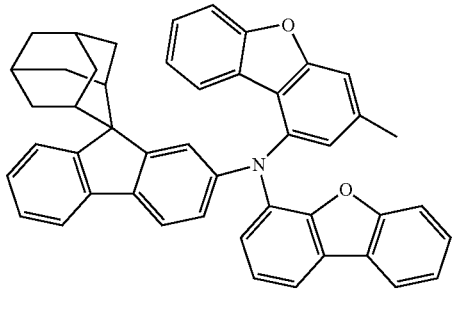
104
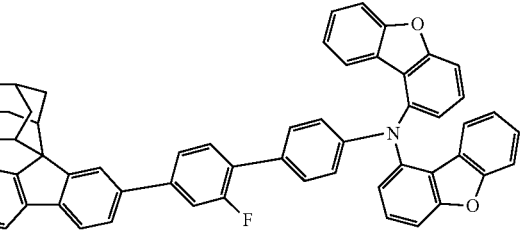

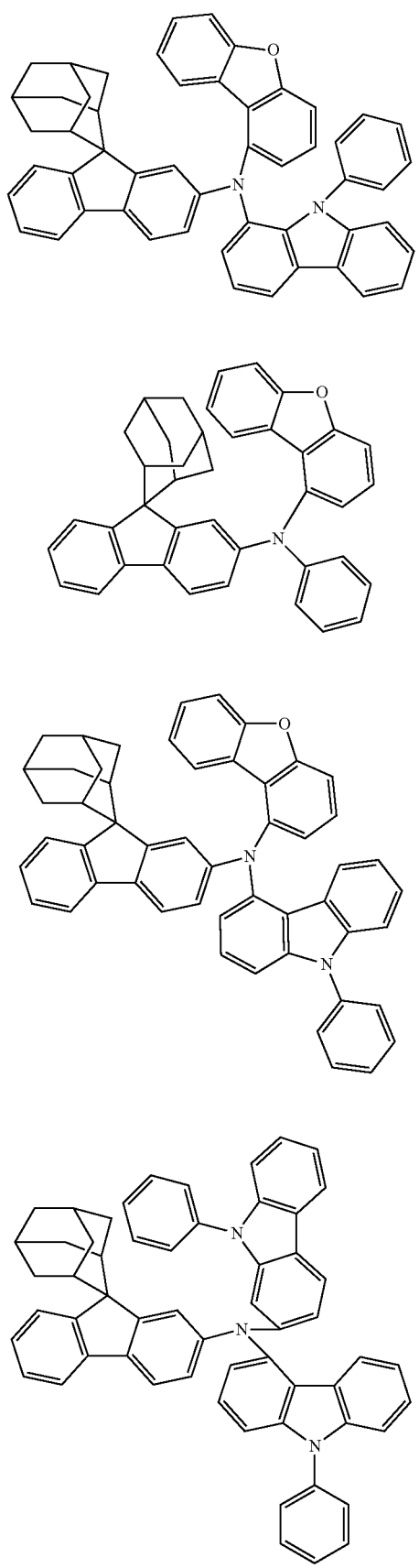
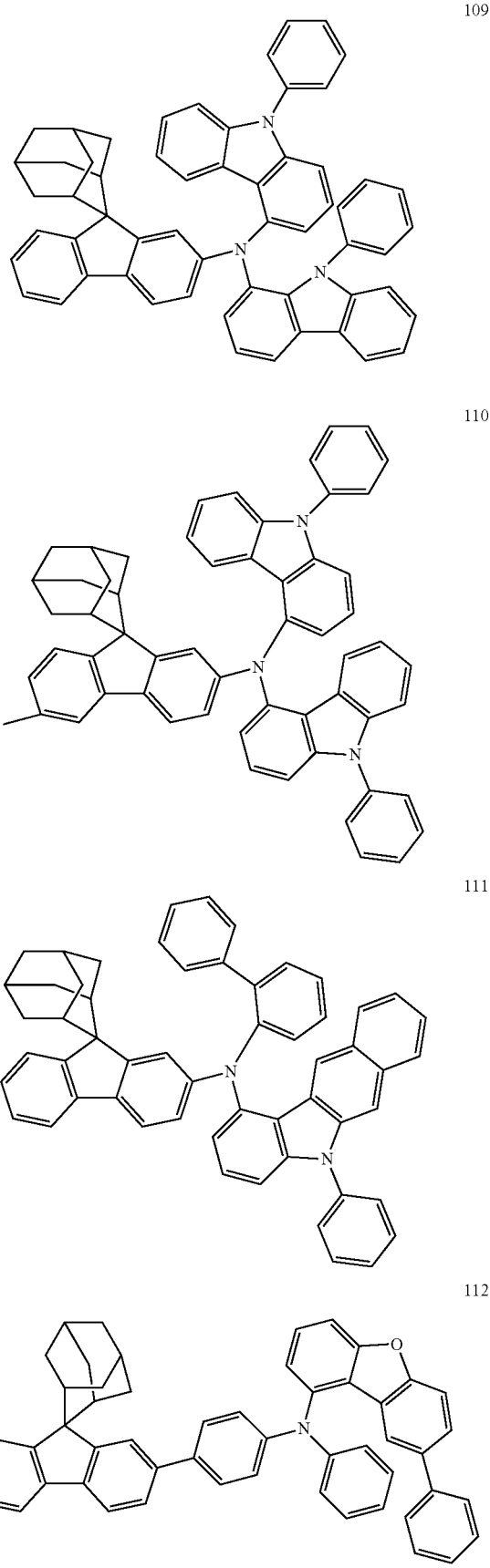

-continued
113
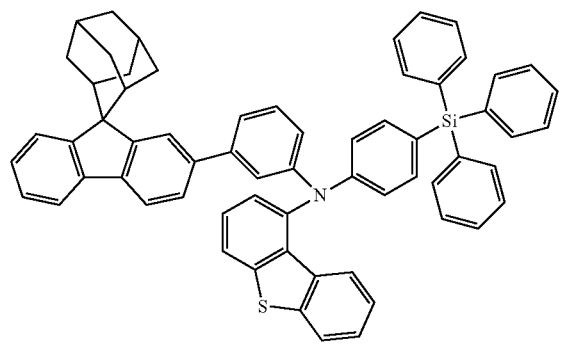
114
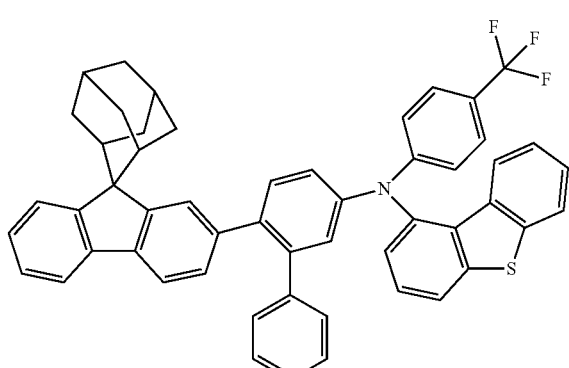
115
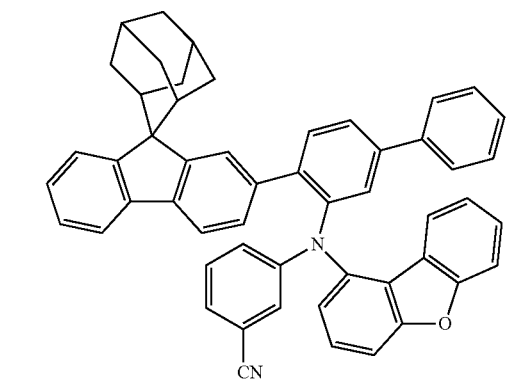
116
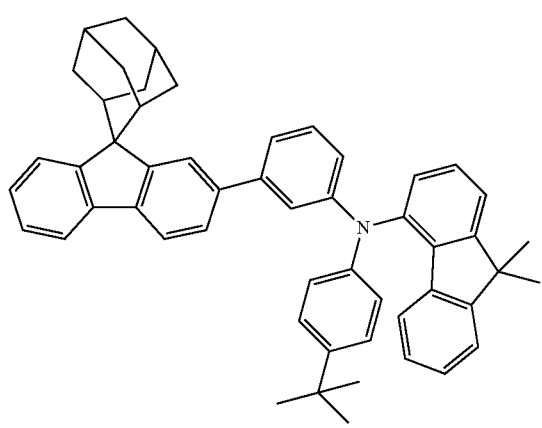
-continued
117
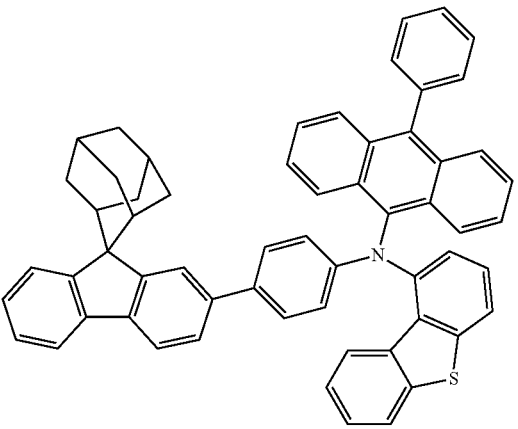
118
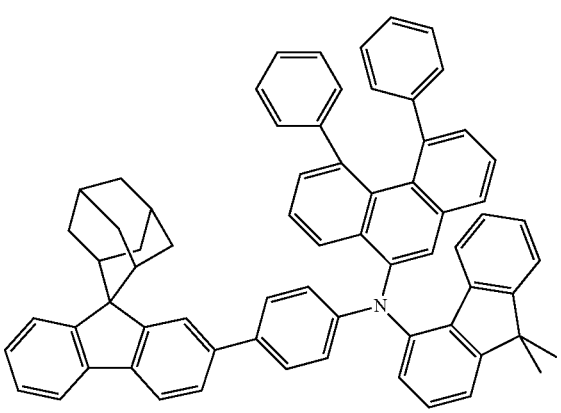
119
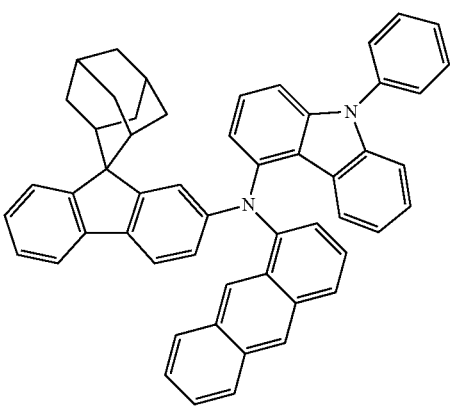
120
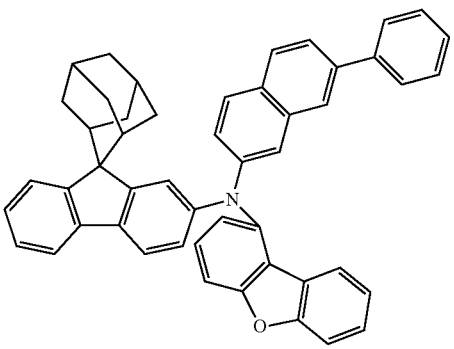

121
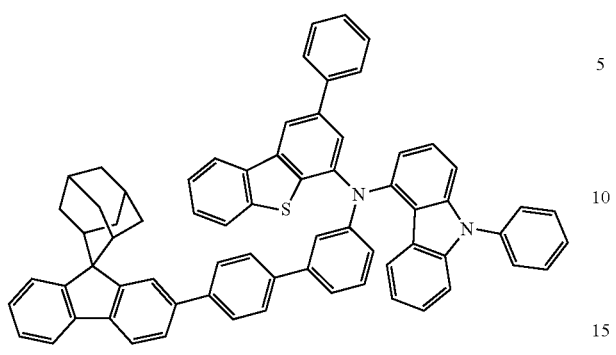
122
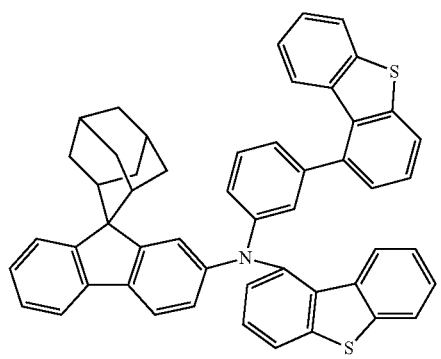
123
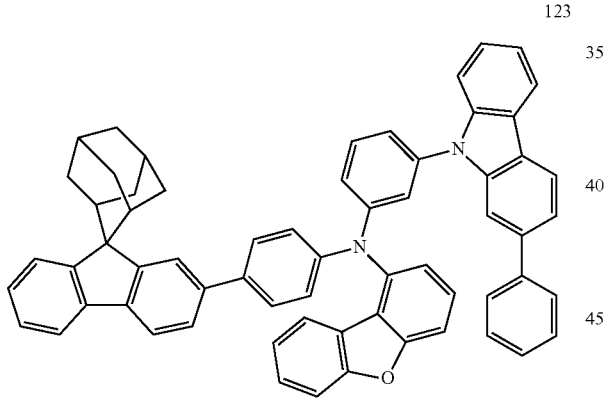
124
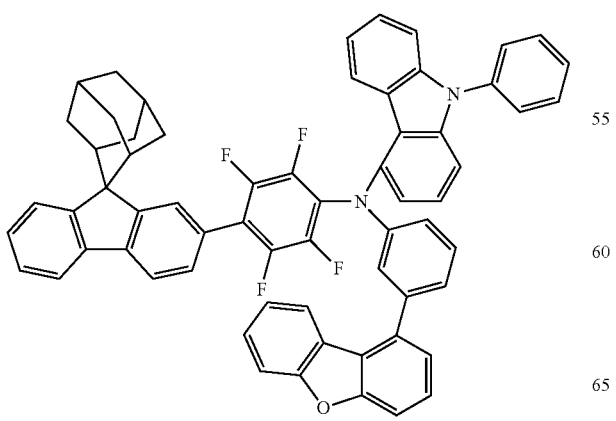
125
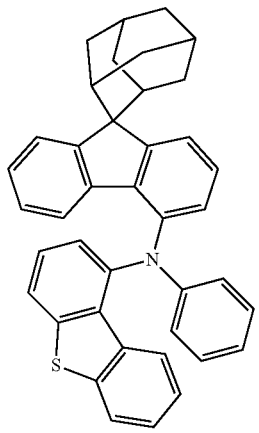
126
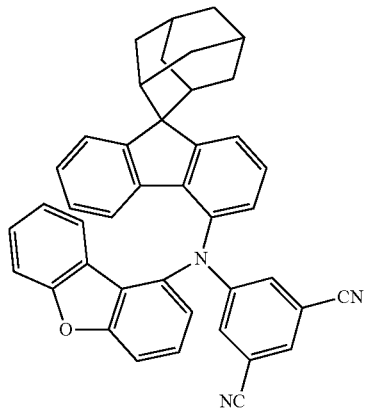
127
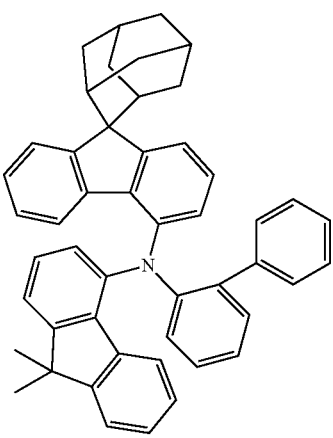

128
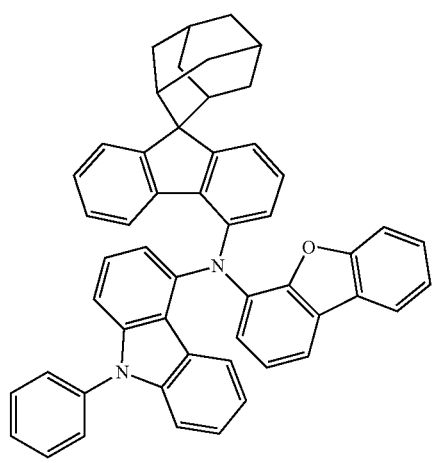
129
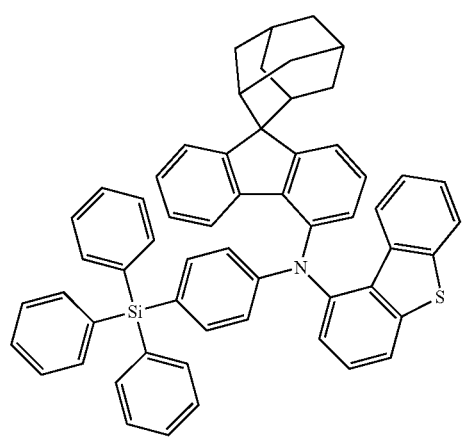
130
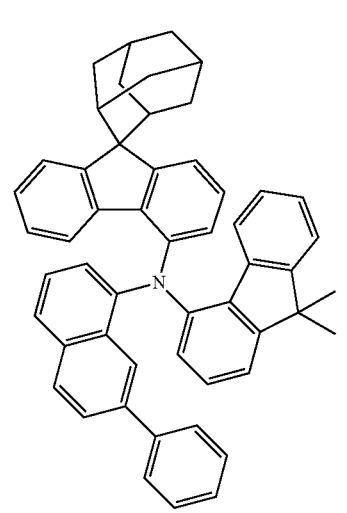
131
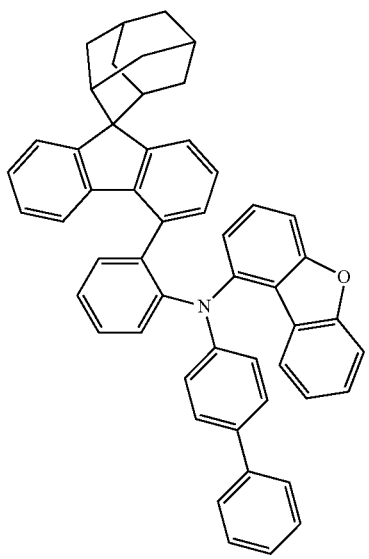
132

133
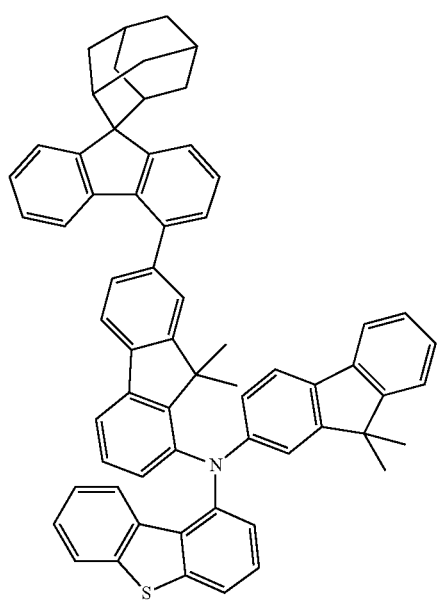
134
135
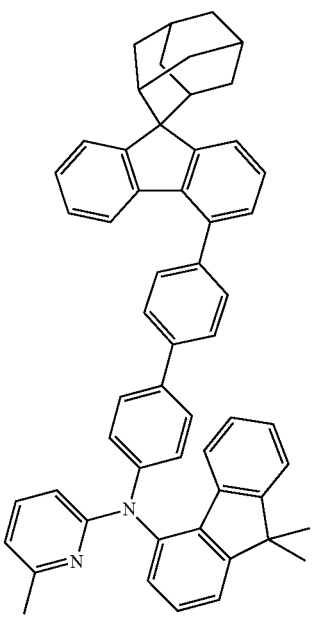
136
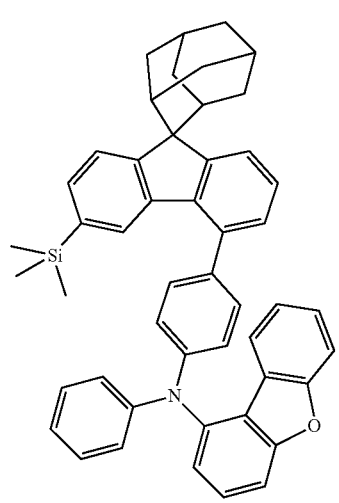

137
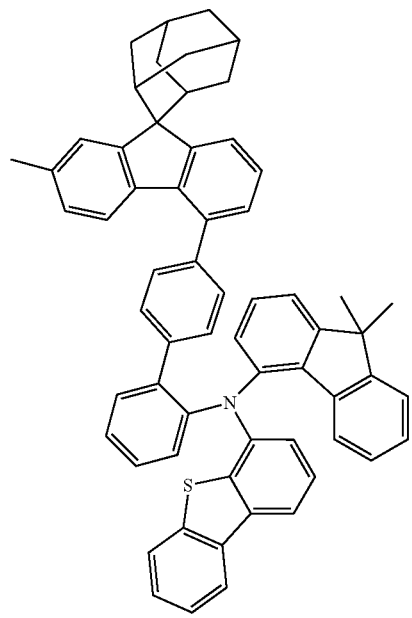
138
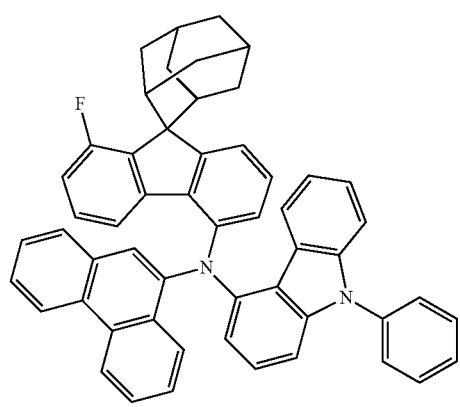
139
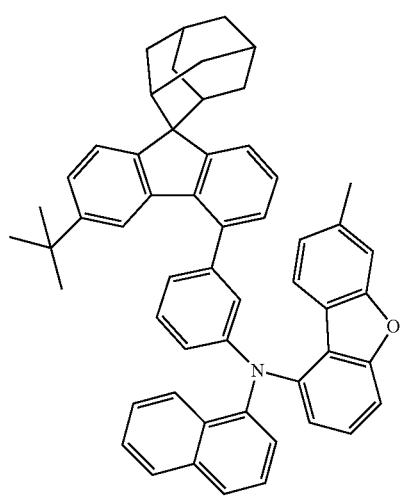
140
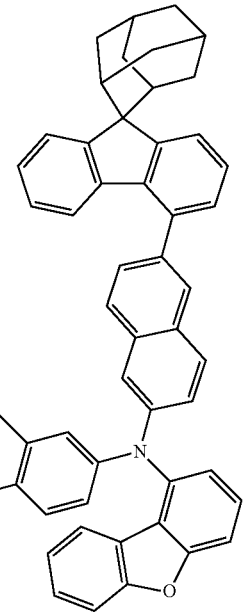
141
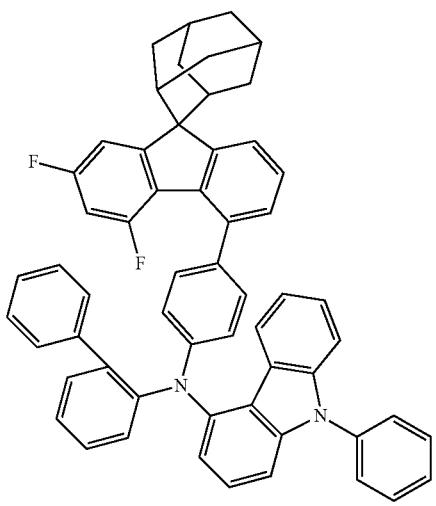
142

143
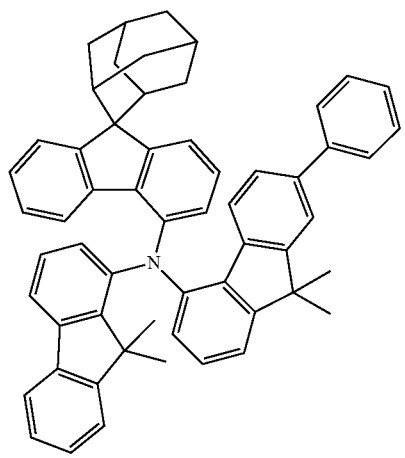
146
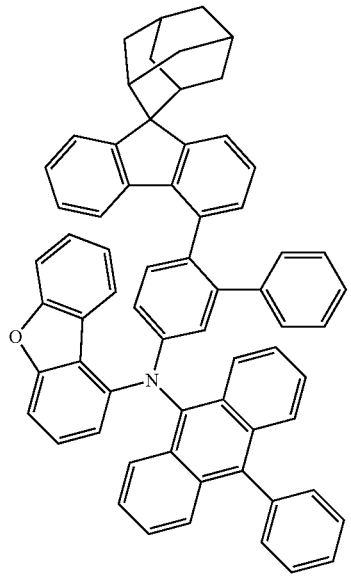
144
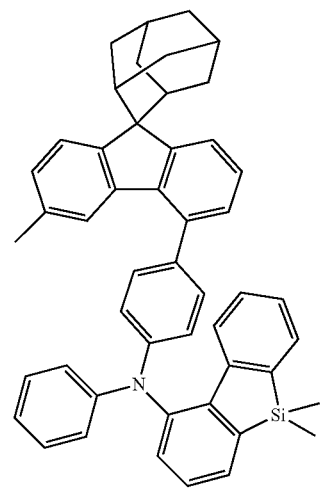
147
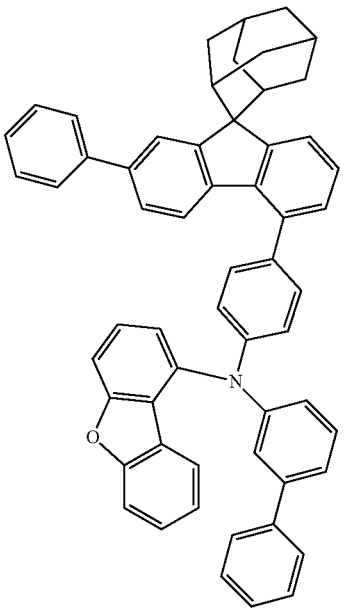
145
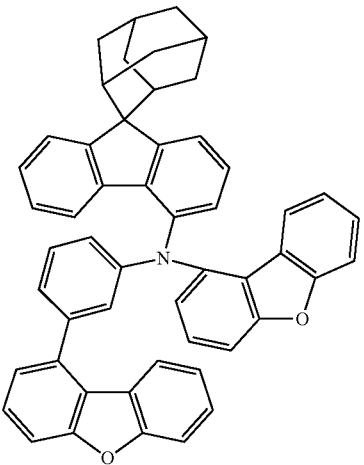
149

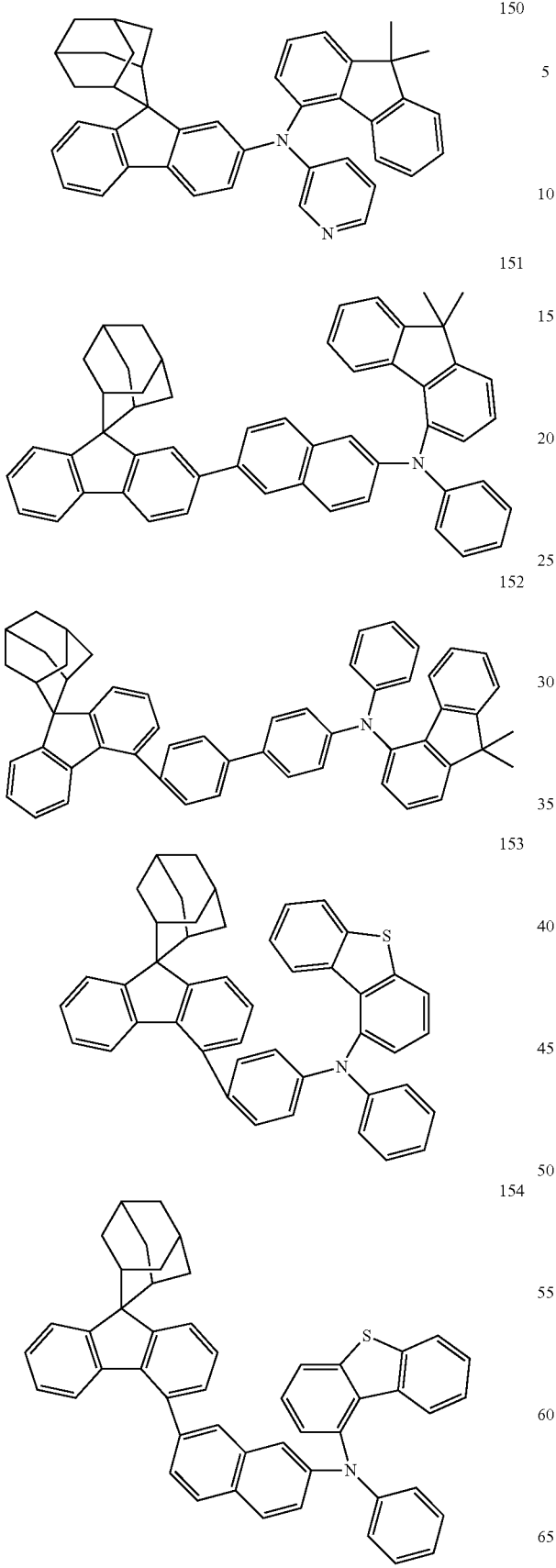
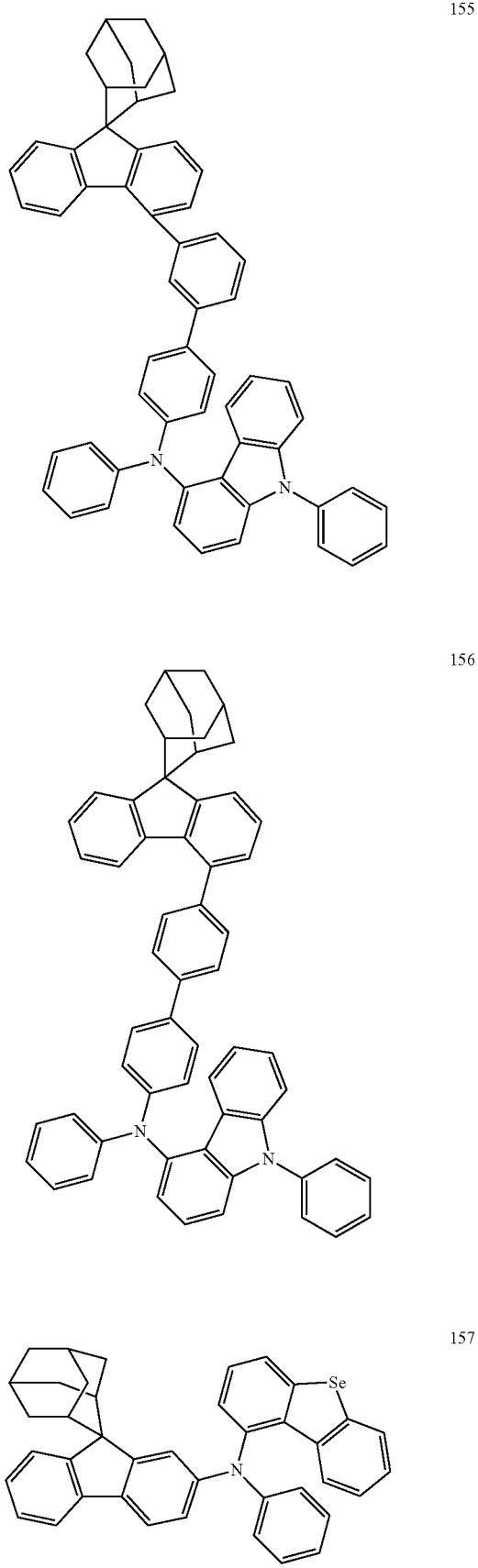

158
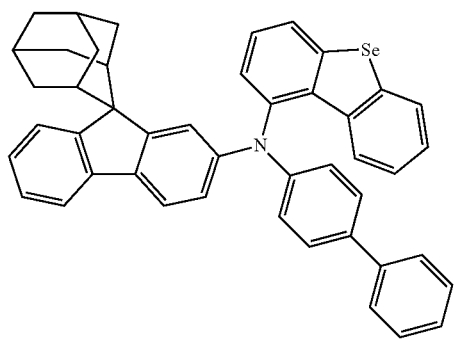
159
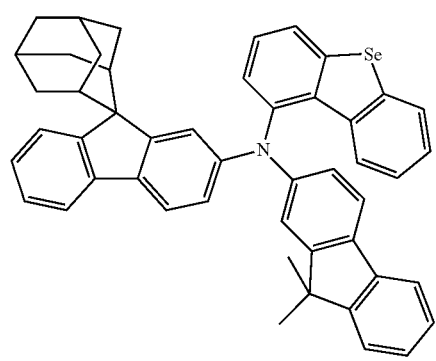
160
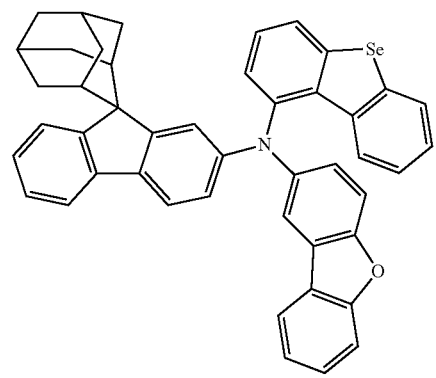
161
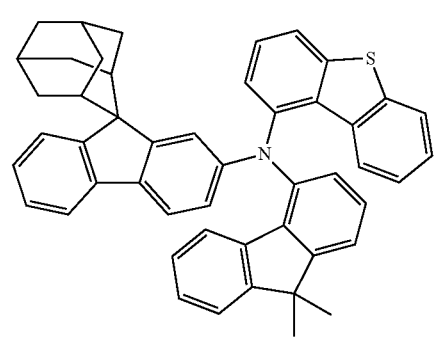
162
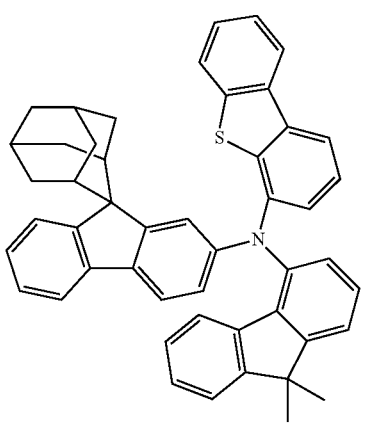
163
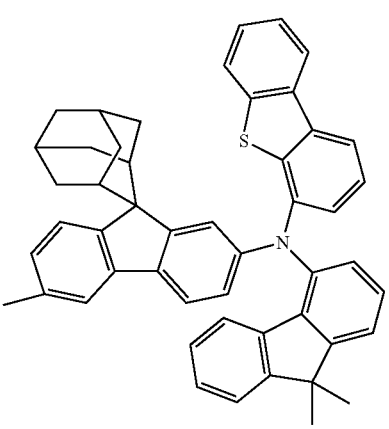
164
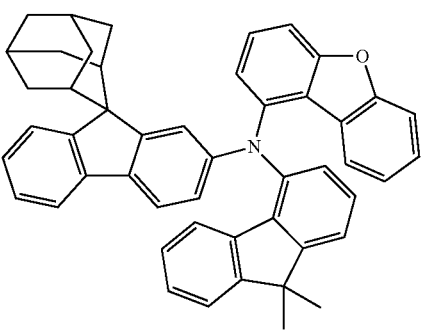
165
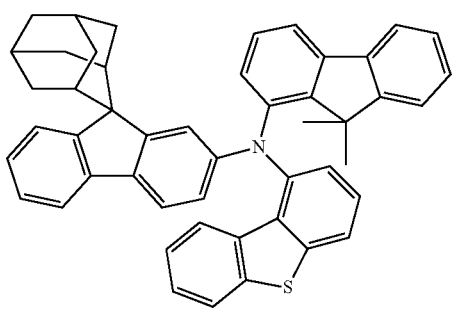

| 95 -continued | 96 -continued |
|---|---|
| 166 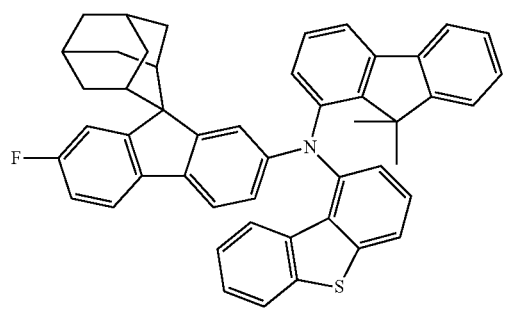 | 170 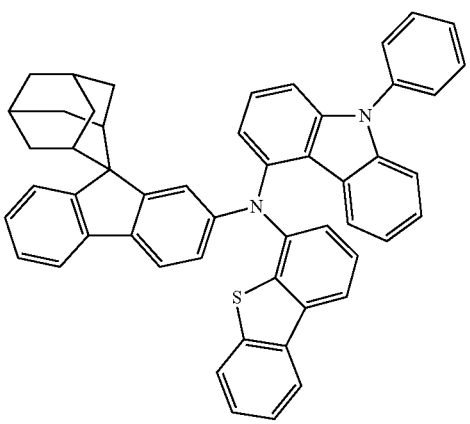 |
| 167 | 171 |
| 168 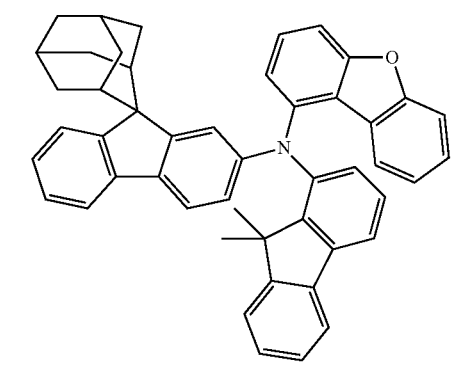 | 172 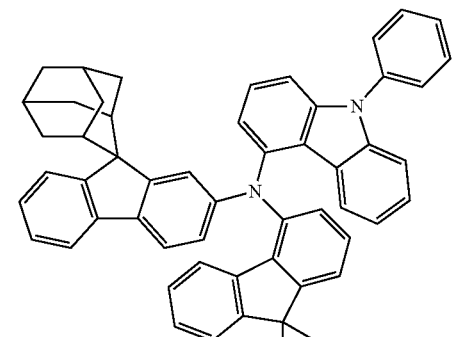 |
| 169 | 173 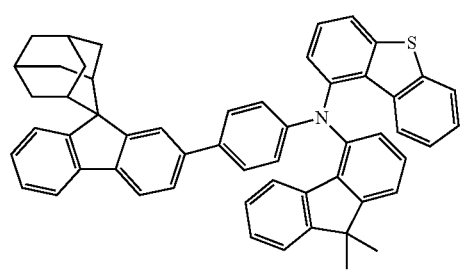 |

174
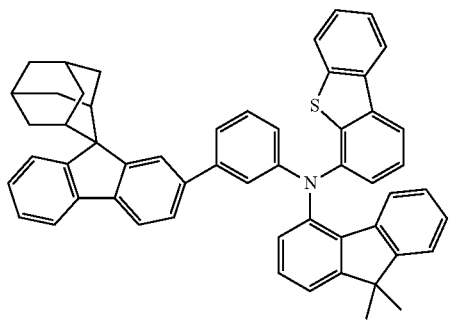
178
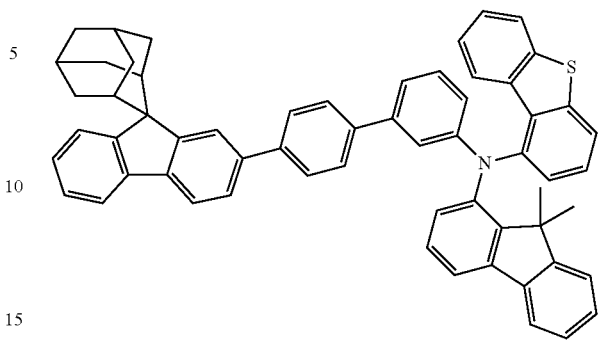
175
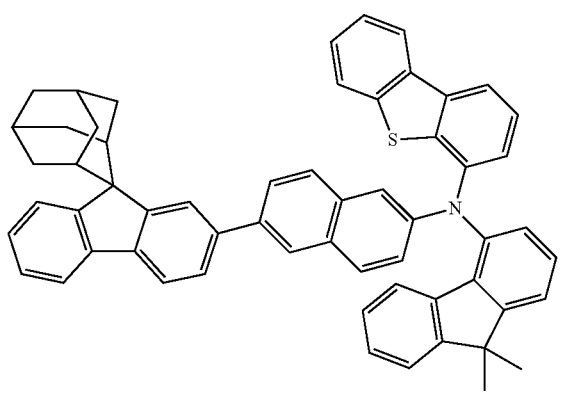
179
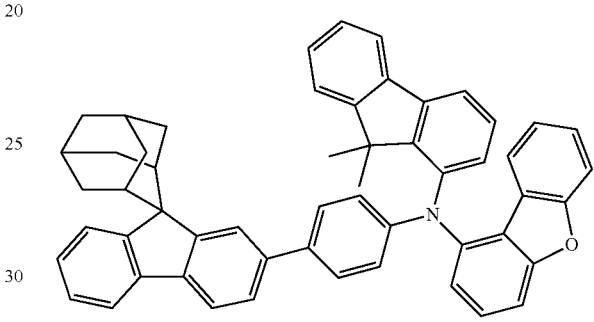
176
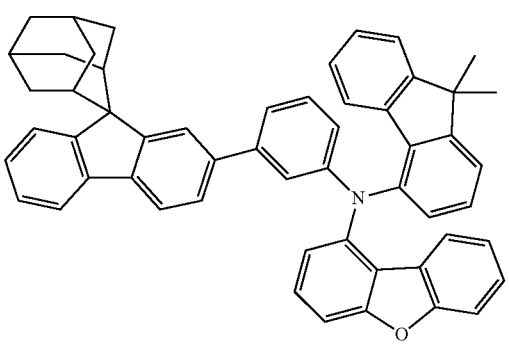
180
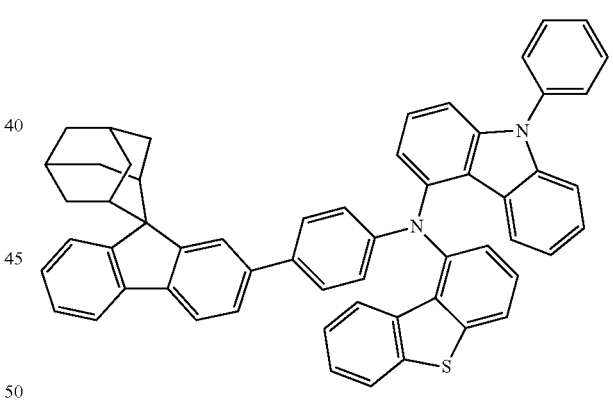
177
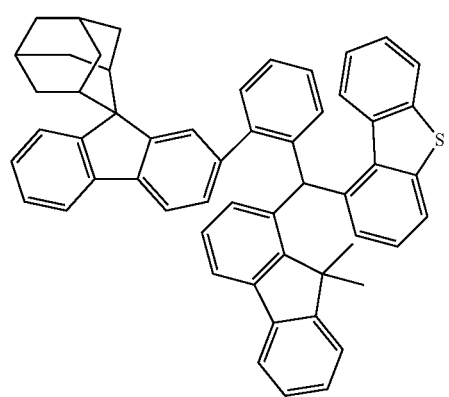
181
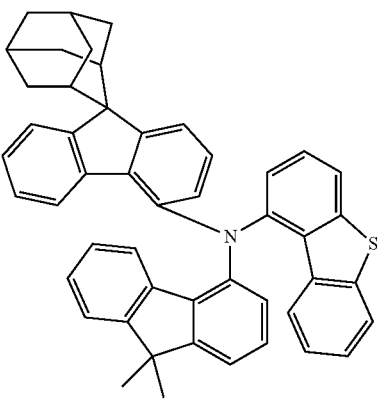

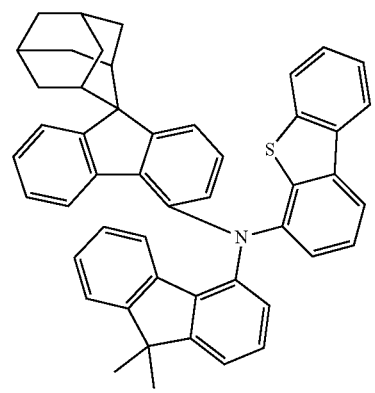
182
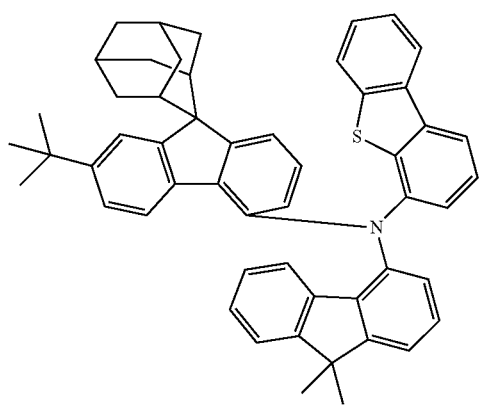
183
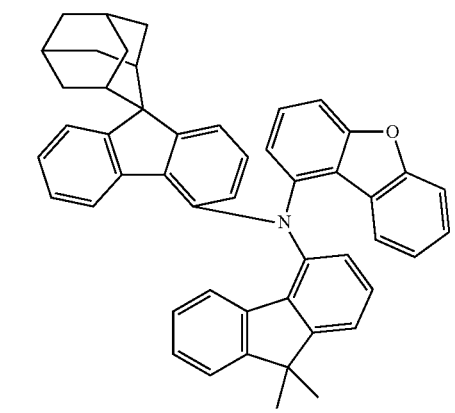
184
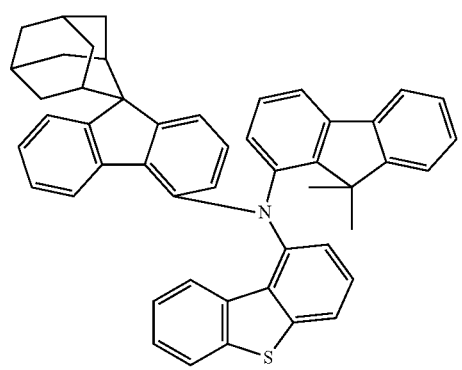
185
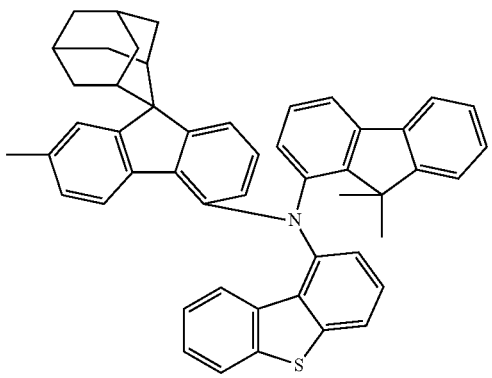
186
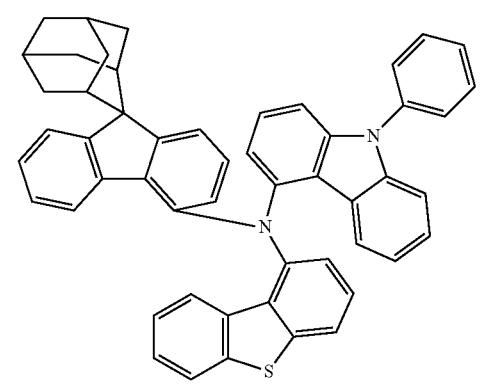
187
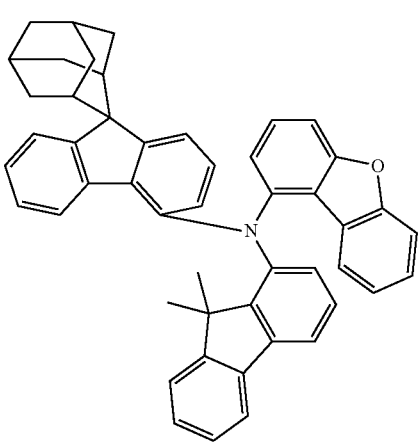
188
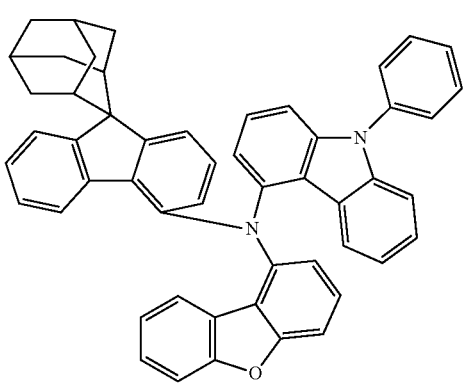
189

101
-continued
190
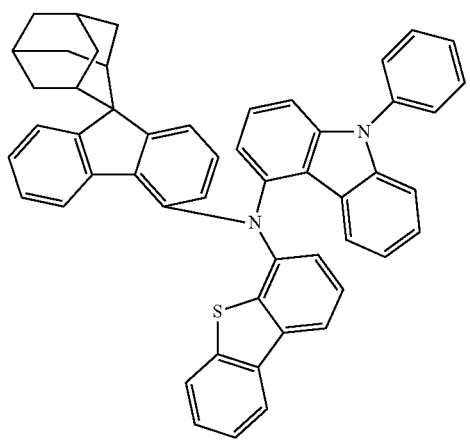
191
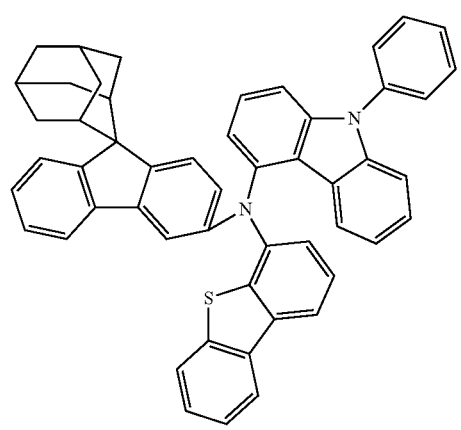
192
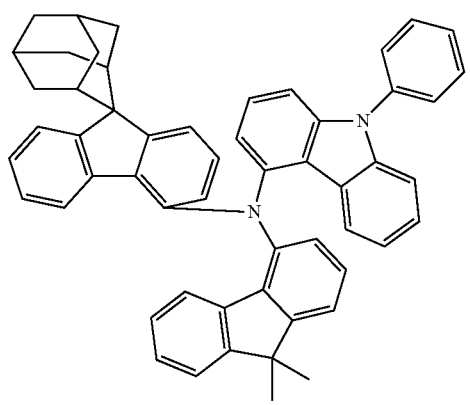
102
-continued
193
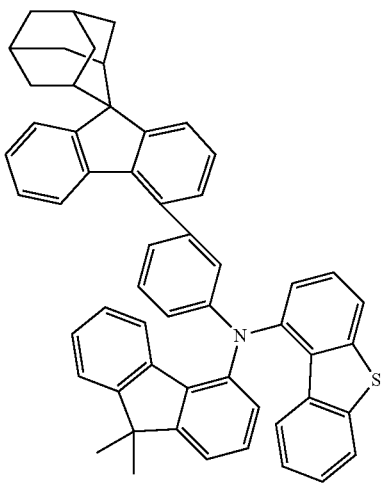
194
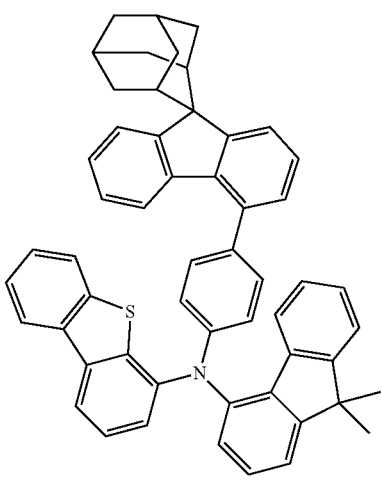
195
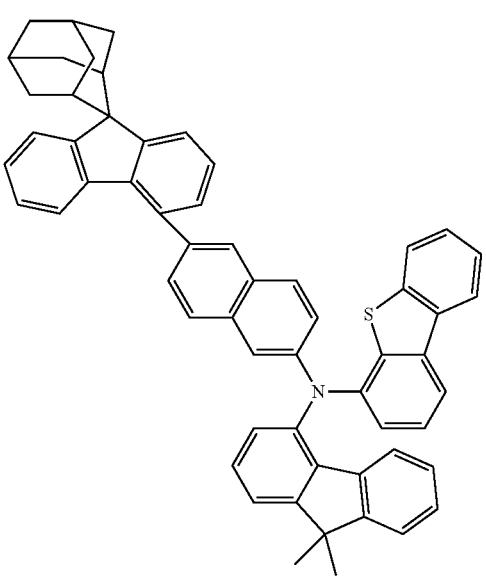

196 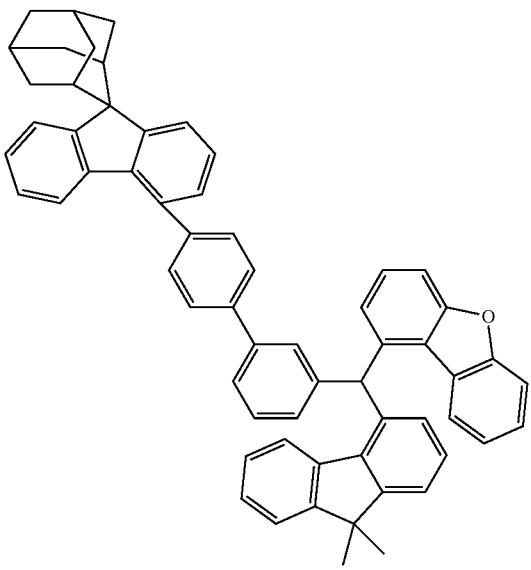

197 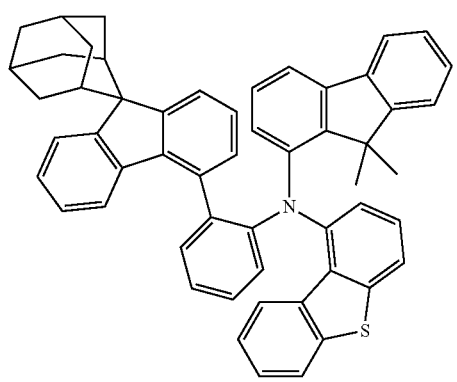

198 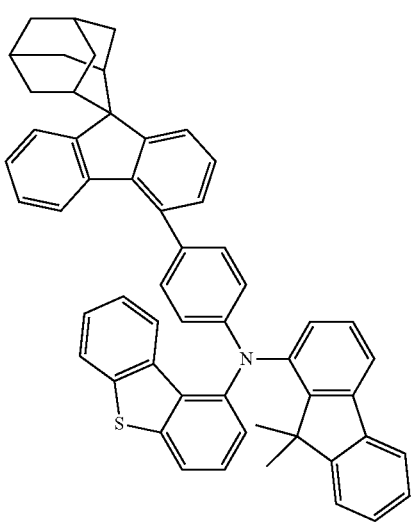

199 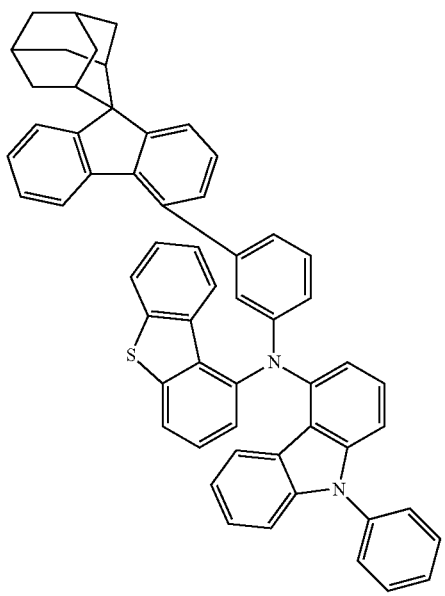

200 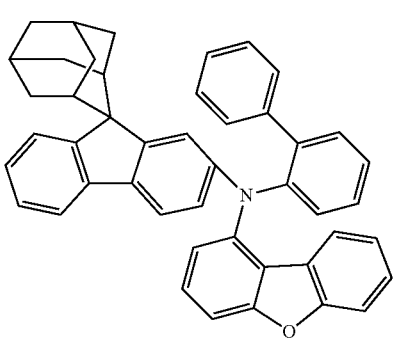

The present disclosure does not specifically limit the methods of synthesis of the nitrogen-containing compound provided, and those skilled in the art may determine a suitable synthesis method according to the organic compound of the present disclosure in conjunction with preparation methods provided in the synthesis example section. In other words, the synthesis example section of the present disclosure provides example methods for the preparation of nitrogen-containing compounds, with raw materials used being obtainable by commercial or well-known processes in the art. All nitrogen-containing compounds provided herein may be obtained by those skilled in the art in accordance with these example preparation methods, and each of specific methods for the preparation of such nitrogen-containing compounds will not be described in detail herein, and those skilled in the art should not consider this to be a limitation of the present disclosure.

A second aspect of the present disclosure provides an electronic component including an anode and a cathode which is arranged oppositely to the anode, and a functional layer disposed between the anode and the cathode, wherein the functional layer may contain the nitrogen-containing compound of the first aspect of the present disclosure.

The nitrogen-containing compound provided herein may be used to form at least one organic film layer of the functional layer to improve lifetime characteristic of the electronic component.

Alternatively, the functional layer includes a hole transporting layer, and the hole transporting layer comprises the nitrogen-containing compound provided by the present disclosure. The hole transporting layer may be composed of the nitrogen-containing compound provided by the present disclosure, or may be composed of the nitrogen-containing compound provided by the present disclosure and other materials. The hole transporting layer may include one or two or more layers.

Alternatively, the electronic component is an organic electroluminescent device or a photoelectric conversion device. The organic electroluminescent device may be a green light device, a red light device, or a blue light device.

According to one exemplary embodiment, the hole transporting layer includes a first hole transporting layer and a second hole transporting layer, wherein the first hole transporting layer is closer to the anode than the second hole transporting layer, and the second hole transporting layer comprises the nitrogen-containing compound.

According to one embodiment, the electronic component is an organic electroluminescent device. As shown in FIG. 1, the organic electroluminescent device may include an anode 100, a first hole transporting layer 321, a second hole transporting layer 322, an organic light-emitting layer 330 as an energy conversion layer, an electron transporting layer 340, and a cathode 200 which are sequentially stacked.

Alternatively, the anode 100 includes the following anode material, which is preferably a material having a large escape work (work function) that facilitates holes injection into the functional layer. Specific examples of anode materials include metals such as nickel, platinum, vanadium, chromium, copper, zinc, and gold or alloys thereof; metal oxides such as zinc oxide, indium oxide, indium tin oxide (ITO), and indium zinc oxide (IZO); combinations of metals and oxides such as ZnO:Al or $SnO_2$:Sb; or conductive polymers such as poly(3-methylthiophene), poly[3,4-(ethylidene-1,2-dioxy)thiophene] (PEDT), polypyrrole and polyaniline, but are not limited thereto. It is preferable to a transparent electrode containing indium tin oxide (ITO) as the anode.

Alternatively, the first hole transporting layer 321 may include one or more hole transport materials, which may be selected from carbazole polymers, carbazole-linked triarylamines, or other types of compounds, without any particular limitation in the present disclosure. For example, the first hole transporting layer 321 may be composed of the compound TCTA.

Alternatively, the organic light-emitting layer 330 may be composed of a single light-emitting material, or may include a host material and a guest material. Alternatively, the organic light-emitting layer 330 is composed of a host material and a guest material. Holes injected into the organic light-emitting layer 330 and electrons injected into the organic light-emitting layer 330 may be recombined in the organic light-emitting layer 330 to form excitons, and the excitons transfer energy to the host material, then the host material transfers energy to the guest material, thereby enabling the guest material to emit light.

The host material of the organic light-emitting layer 330 may be a metal chelate compound, a bis-styryl derivative, an aromatic amine derivative, a dibenzofuran derivative, or other types of materials, and the present disclosure does not make any special limitation on this.

The guest material of the organic light-emitting layer 330 may be a compound having a condensed aryl ring or a derivative thereof, a compound having a heteroaryl ring or a derivative thereof, an aromatic amine derivative, or other material, and the present disclosure does not make any special limitation on this.

The electron transporting layer 340 may be a monolayer structure or a multilayer structure, and may include one or more electron transport materials. The electron transport materials may be selected from, but are not limited to, a benzimidazole derivative, an oxadiazole derivative, a quinoxaline derivative, or other electron transport materials. In an example of the present disclosure, the electron transporting layer 340 may be composed of TPBi and LiQ, or of DBimiBphen and LiQ.

In the present disclosure, the cathode 200 may include a cathode material, which is a material having a small escape work and facilitating electrons injection into the functional layer.

Specific examples of cathode materials include, but are not limited to, metals such as magnesium, calcium, sodium, potassium, titanium, indium, yttrium, lithium, gadolinium, aluminum, silver, tin, and lead, or alloys thereof; or multilayer materials such as LiF/Al, Liq/Al, $LiO_2$/Al, LiF/Ca, LiF/Al and $BaF_2$/Ca. It is preferable to include a metal electrode containing magnesium and silver as a cathode.

Alternatively, as shown in FIG. 1, a hole injection layer 310 may further be disposed between the anode 100 and the first hole transporting layer 321, so as to enhance the ability of injecting holes into the first hole transporting layer 321. The hole injection layer 310 may be made of a benzidine derivative, a starburst arylamine compound, a phthalocyanine derivative, or other materials, and the present disclosure does not make any special limitation on this. For example, the hole injection layer 310 may be composed of HAT-CN or m-MTDATA.

Alternatively, as shown in FIG. 1, an electron injection layer 350 may further be disposed between the cathode 200 and the electron transporting layer 340, so as to enhance the ability of injecting electrons into the electron transporting layer 340. The electron injection layer 350 may include an inorganic material such as an alkali metal sulfide, an alkali metal halide, or a complex of an alkali metal and an organic substance. For example, the electron injection layer 350 may include LiQ.

According to one embodiment, the organic electroluminescent device is a blue light device.

Figure 3:
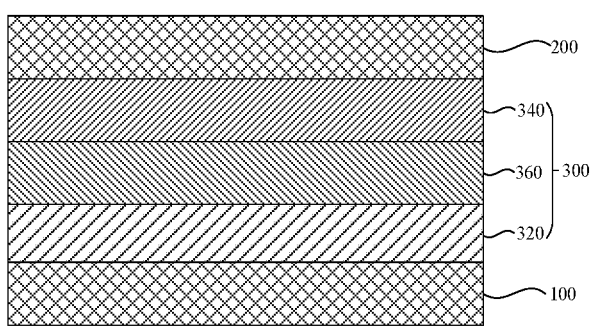
FIG. 3 is a schematic structural view of a photoelectric conversion device according to one embodiment of the present disclosure.

According to another embodiment, the electronic component may be a photoelectric conversion device. As shown in FIG. 3, the photoelectric conversion device may include an anode 100 and a cathode 200 which is arranged oppositely to the anode, and a functional layer 300 disposed between the anode 100 and cathode 200. The functional layer 300 includes the nitrogen-containing compound provided in the present disclosure.

According to one embodiment, as shown in FIG. 3, the functional layer 300 includes a hole transporting layer 320 including the nitrogen-containing compound of the present disclosure. The hole transporting layer 320 may be composed of the nitrogen-containing compound provided by the present disclosure, or may be composed of the nitrogen-containing compound provided by the present disclosure and other materials.

Alternatively, the hole transporting layer 320 may further include an inorganic dopant material to improve hole transport performance of the hole transporting layer 320.

According to one specific embodiment, as shown in FIG. 3, the photoelectric conversion device may include an anode 100, a hole transporting layer 320, a photoelectric conversion layer 360, an electron transporting layer 340, and a cathode 200 which are sequentially stacked.

Alternatively, the photoelectric conversion device may be a solar cell, in particular, an organic thin film solar cell. For example, in one embodiment of the present disclosure, the solar cell may include an anode, a hole transporting layer, a photoelectric conversion layer, an electron transporting layer, and a cathode that are sequentially stacked, wherein the hole transporting layer includes the nitrogen-containing compound of the present disclosure.

A third aspect of the present disclosure provides an electronic device including the electronic component according to the second aspect of the present disclosure.

Figure 2:
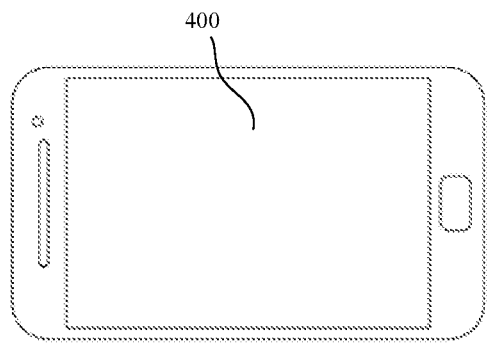
FIG. 2 is a schematic structural view of a first electronic device according to one embodiment of the present disclosure.

According to one embodiment, as shown in FIG. 2, the electronic device is a first electronic device 400 including the organic electroluminescent device. The first electronic device 400 may be, for example, a display device, a lighting device, an optical communication device, or other types of electronic devices, and may include, for example, but not limited to, a computer screen, a mobile phone screen, a television, an electronic paper, an emergency light, an optical module and the like.

Figure 4:
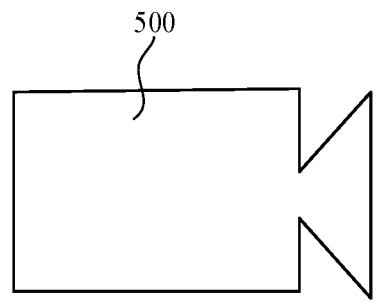
FIG. 4 is a schematic structural view of a second electronic device according to one embodiment of the present disclosure.

According to another embodiment, as shown in FIG. 4, the electronic device is a second electronic device 500 including the photoelectric conversion device. The second electronic device 500 may be, for example, a solar power generation device, an optical detector, a fingerprint recognition device, an optical module, a CCD camera, or other types of electronic devices.

All compounds prepared by synthetic methods not mentioned in the present disclosure are obtained from commercially available raw material products.

The present disclosure is further described below by way of examples, but the present disclosure is not limited thereto.

Synthesis examples are used to describe the synthesis of nitrogen-containing compounds of the present disclosure.

The compounds of the present disclosure can be synthesized by the following synthesis route:

Formula (1)

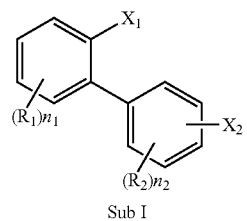

Sub I

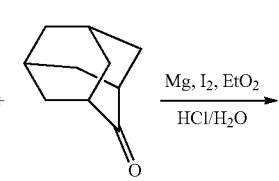

Mg, I$_2$, EtO$_2$
HCl/H$_2$O

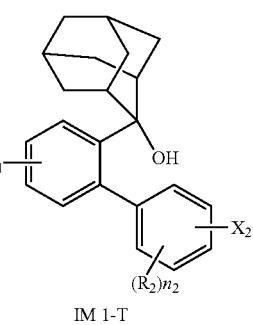

IM 1-T

Formula (2)

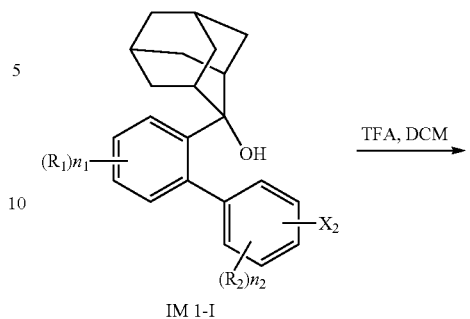

IM 1-I

TFA, DCM

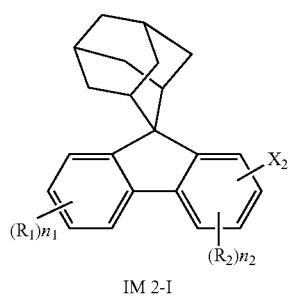

IM 2-I

Optionally, when L is not single bond, the steps shown in Formulae (3-1) and (3-2) are included:

Formula (3-1)

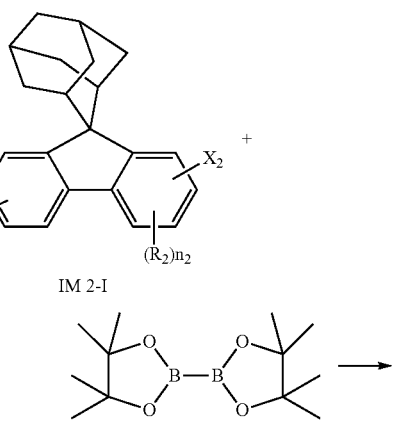

IM 2-I

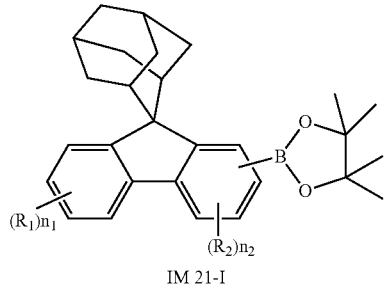

IM 21-I

-continued

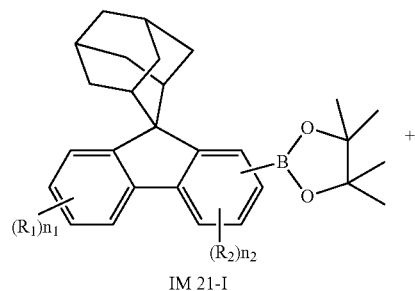

IM 21-I

+

Formula (3-2)

$X_3-L-Y \longrightarrow$

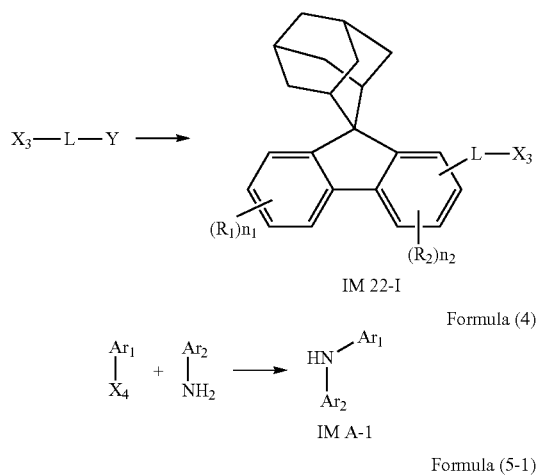

IM 22-I $\underset{X_4}{Ar_1} + \underset{NH_2}{Ar_2} \longrightarrow HN\underset{Ar_2}{\overset{Ar_1}{\diagdown}}$

IM A-1

Formula (4)

Formula (5-1)

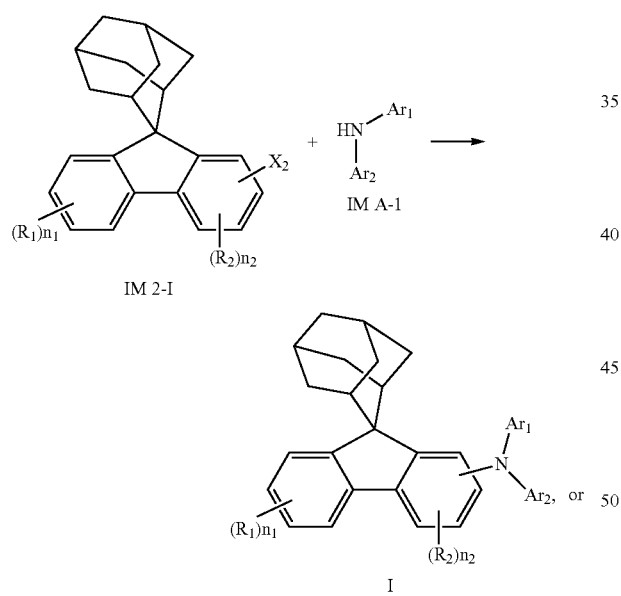

IM 2-I

+ IM A-1 →

I

Formula (5-2)

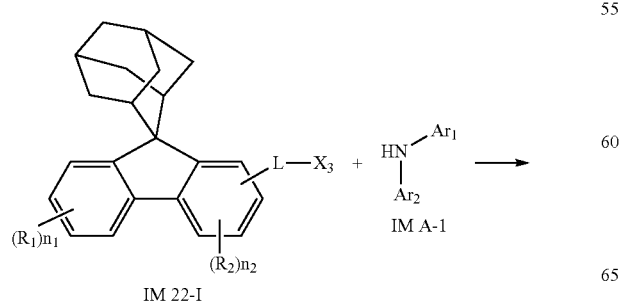

IM 22-I + IM A-1 →

-continued

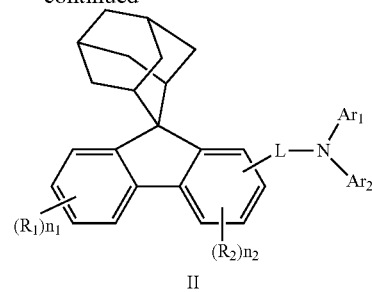

II

The specific structure of the raw material Sub I is as follows:

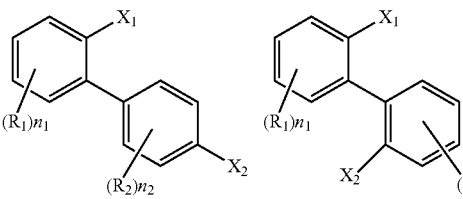

Accordingly, in formula (5-1), the specific structure of compound I is as follows:

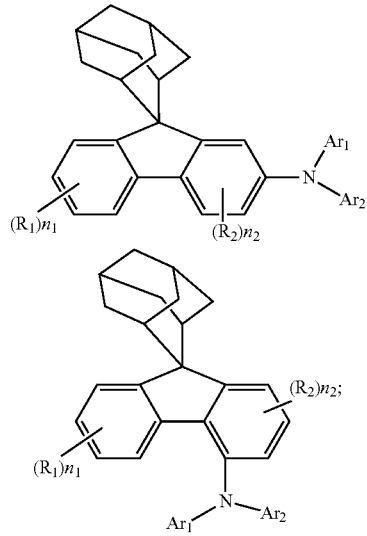

The specific structure of compound II in formula (5-2) is as follows:

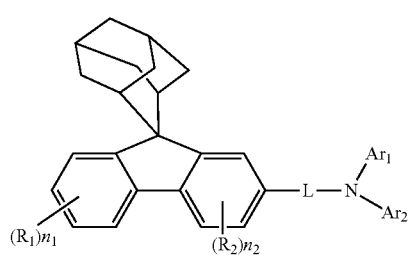

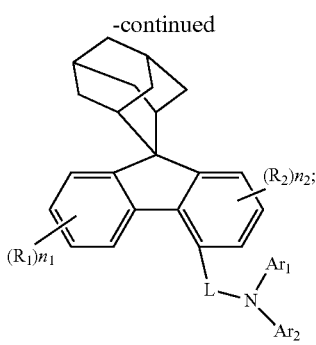

Unless otherwise stated, $R_1$, $R_2$, $n_1$, $n_2$ and L are defined as described above. $Ar_1$ is defined in the same way as Ar, and $Ar_2$ is defined in the same way

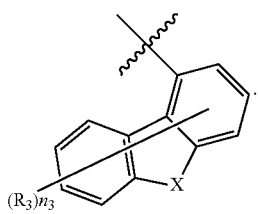

$X_1$ is selected from Br or I, $X_2$ is selected from Cl or Br, $X_3$ is selected from Cl or Br, and Y is I.

To illustrate specific synthetic methods for individual compounds, the following are examples of specific synthetic methods for some of the compounds of the present disclosure.

Synthesis Example 1: Synthesis of Compound 2

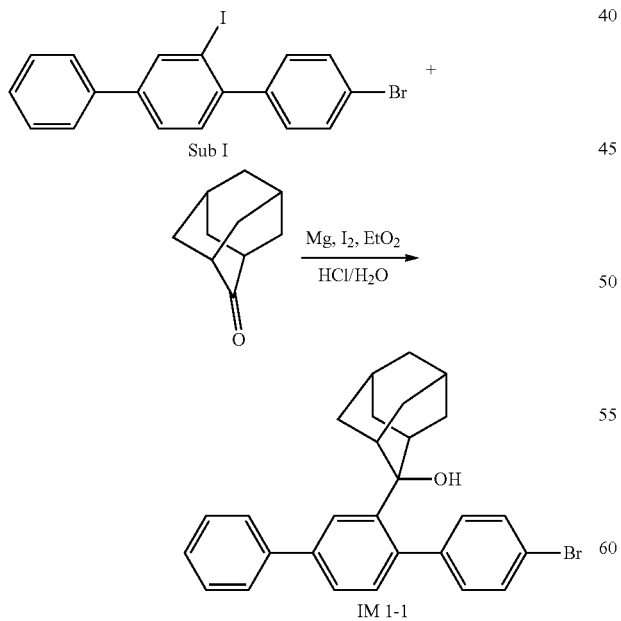

(1) Under nitrogen atmosphere, 1.1 g (45 mmol) of dried magnesium granules treated with dilute hydrochloric acid and 30 mL of diethyl ether were placed in a dried three-necked flask, and 0.1 g of iodine granules was added thereinto. A diethyl ether solution (20 mL) in which a raw material Sub 1 (7.89 g, 18 mmol) was dissolved was slowly added into the flask dropwise under stirring. After the completion of dropping addition, the solution was heated to reflux (35° C.) and reacted for 2 hours. Then the reaction solution was cooled to 0° C., and a solution of diethyl ether (20 mL) in which adamantanone (2.72 g, 18 mmol) was dissolved was slowly added dropwise. After the completion of dropping addition, the solution was again heated to reflux (35° C.), and reacted for 8 hours under stirring. The reaction solution was slowly cooled to room temperature, 5% hydrochloric acid was added slowly until pH <7, and then extracted three times with 60 mL of ethyl acetate. Organic phases were combined, dried with 5 g of magnesium sulfate, and filtered. The filtrate was distilled under reduced pressure to remove the solvent. The obtained crude was purified by silica gel column chromatography with a mixed solvent of dichloromethane and n-heptane at a ratio of 1:4 (at a volume ratio), then a intermediate IM 1-1 was obtained (5.5 g, yield: 66%).

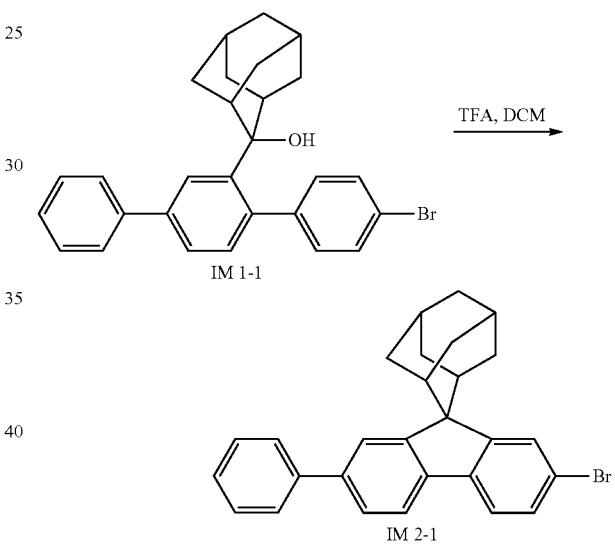

(2) Under the protection of nitrogen, 5 g (11 mmol) of the intermediate IM 1-1 and 3.7 g (33 mmol) of trifluoroacetic acid were added to a three-necked flask, and 50 mL of dichloromethane was added thereinto, and stirred at room temperature (25° C.) for 5 hours. Then, a aqueous solution of sodium hydroxide was added into the reaction solution until the pH became neutral, and then the mixture was separated. Organic phase was dried with magnesium sulfate, then filtered, and the filtrate was distilled under reduced pressure to remove the solvent. The obtained crude was purified by silica gel column chromatography with n-heptane, a intermediate IM 2-1 was obtained (4.1 g, yield: 85%).

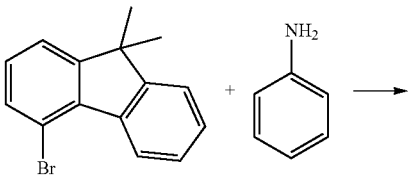

-continued

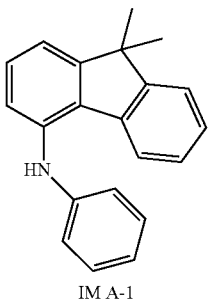

IM A-1

-continued

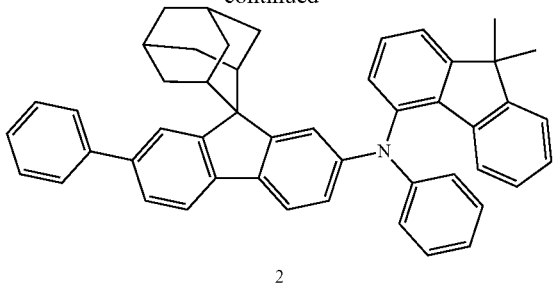

2

(3) Under the protection of nitrogen, 3.5 g (12.8 mmol) of 4-bromo-9,9'-dimethylfluorene, 1.2 g (12.8 mmol) of aniline, 0.12 g (0.13 mmol) of tris(dibenzylideneacetone)dipalladium, 0.12 g (0.26 mmol) of 2-dicyclohexylphosphino-2', 4',6'-triisopropylbiphenyl, 2.46 g (25.6 mmol) of sodium tert-butoxide, and 35 mL of toluene were added into a three-necked flask, the flask was heated to 110° C. and reacted under reflux for 4 hours. The reaction solution was washed with water, and separated. Organic phase was dried with magnesium sulfate, and then filtered. The filtrate was distilled under reduced pressure to remove the solvent. The obtained crude was recrystallized twice from a mixed solvent of dichloromethane and n-heptane (at a volume ratio of 1:5) to obtain Intermediate IM A-1 (3.2 g, yield: 87%).

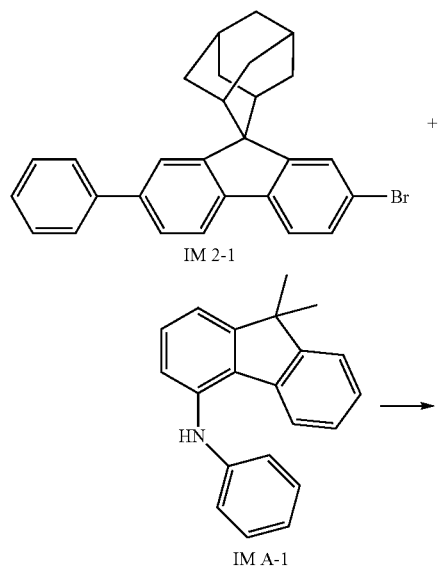

(4) Under the protection of nitrogen, 4 g (10 mmol) of the intermediate IM 2-1 and 2.88 g (10 mmol) of the intermediate IM A-1, 0.1 g (0.1 mmol) of tris(dibenzylideneacetone) dipalladium, 0.08 g (0.2 mmol) 2-dicyclohexylphosphino-2',6'-dimethoxybiphenyl, 1.9 g (20 mmol) of sodium tert-butoxide, and 40 mL of toluene were added into a three-necked flask, the flask was heated to 110° C., and reacted under reflux for 10 hours. The reaction solution was cooled to room temperature, washed with water, and separated. Organic phase was dried with magnesium sulfate, and then filtered. The filtrate was distilled under reduced pressure to remove the solvent. The obtained crude was recrystallized twice from toluene to obtain Compound 2 (4.95 g, yield: 76%). Mass spectrometry: m/z=646.3[M+H]$^+$.

NMR data for compound 2: $^1$H NMR (400 MHz, CD$_2$Cl$_2$): 8.09 (d, 1H), 7.91 (m, 2H), 7.79-7.71 (d, 4H), 7.59-7.29 (m, 12H), 7.18-7.00 (m, 4H), 2.91 (d, 2H), 2.61 (d, 2H), 2.16 (s, 1H), 1.90 (s, 3H$_4$), 1.77 (d, 2H), 1.69 (d, 2H), 1.60 (s, 2H), 1.50 (s, 6H) ppm.

Synthesis Examples 2 to 12

The compounds shown in Table 1 were synthesized with reference to the method of Synthesis Example 1, except that the raw material Sub 1 in step (1) was replaced with individual raw material Sub I in Table 1; the 4-bromo-9,9'-dimethylfluorene in step (3) was replaced with the raw material Sub II, and the aniline was replaced with the raw material Sub III. The used main raw materials, and the yield from individual final step and the mass spectrometry results of compounds are shown in Table 1.

TABLE 1

| Synthesis Example | Compound No. | Compound Structure | Sub I | Sub II | Sub III | yield (%) | mass spectrum [M + H]$^+$ |
|---|---|---|---|---|---|---|---|
| 2 | 1 | (structure) | (structure) | (structure) | (structure) | 83 | 570.3 |

TABLE 1-continued

| Synthesis Example | Compound No. | Compound Structure | Sub I | Sub II | Sub III | yield (%) | mass spectrum [M + H]+ |
|---|---|---|---|---|---|---|---|
| 3 | 5 | 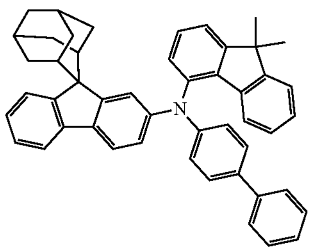 [SMILES: CC1(C)c2ccccc2-c2c(N(c3ccc(-c4ccccc4)cc3)c3ccc4c(c3)C3(c5ccccc5-4)C4CC5CC(C4)CC3C5)cccc21] | | | | 72 | 646.3 |
| 4 | 20 | 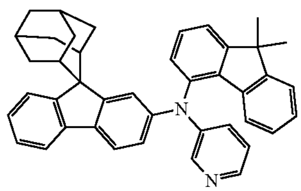 [SMILES: CC1(C)c2ccccc2-c2c(N(c3cccnc3)c3ccc4c(c3)C3(c5ccccc5-4)C4CC5CC(C4)CC3C5)cccc21] | | | | 70 | 571.3 |
| 5 | 21 | 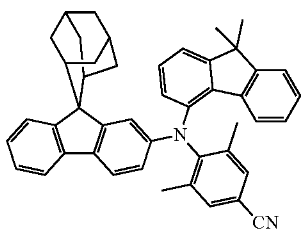 [SMILES: Cc1cc(C#N)cc(C)c1N(c1ccc2c(c1)C1(c3ccccc3-2)C2CC3CC(C2)CC1C3)c1cccc2c1-c1ccccc1C2(C)C] | | | | 54 | 623.3 |
| 6 | 30 | 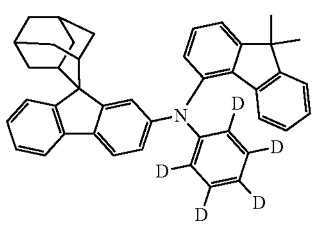 [SMILES: [2H]c1c([2H])c([2H])c(N(c2ccc3c(c2)C2(c4ccccc4-3)C3CC4CC(C3)CC2C4)c2cccc3c2-c2ccccc2C3(C)C)c([2H])c1[2H]] | | | | 69 | 575.3 |
| 7 | 41 | 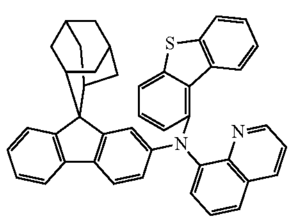 [SMILES: c1ccc2c(c1)-c1ccc(N(c3cccc4cccnc34)c3cccc4sc5ccccc5c34)cc1C21C2CC3CC(C2)CC1C3] | | | | 72 | 611.2 |
| 8 | 62 | 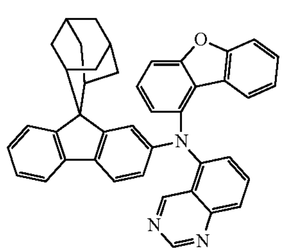 [SMILES: c1ccc2c(c1)-c1ccc(N(c3cccc4ncncc34)c3cccc4oc5ccccc5c34)cc1C21C2CC3CC(C2)CC1C3] | | | | 77 | 596.3 |

TABLE 1-continued

| Synthesis Example | Compound No. | Compound Structure | Sub I | Sub II | Sub III | yield (%) | mass spectrum [M + H]+ |
|---|---|---|---|---|---|---|---|
| 9 | 72 | 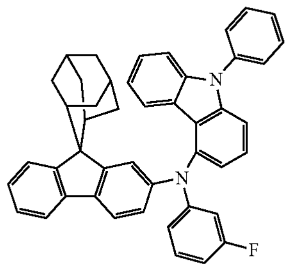 [SMILES: Fc1cccc(N(c2ccc3c(c2)C2(c4ccccc4-3)C3CC4CC(C3)CC2C4)c2cccc3c2c2ccccc2n3-c2ccccc2)c1] | | | | 65 | 637.3 |
| 10 | 89 | 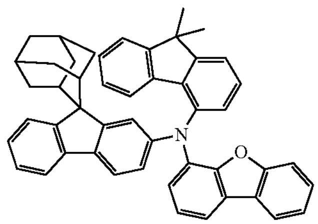 [SMILES: CC1(C)c2ccccc2-c2c(N(c3ccc4c(c3)C3(c5ccccc5-4)C4CC5CC(C4)CC3C5)c3cccc4c3oc3ccccc34)cccc21] | | | | 84 | 660.3 |
| 11 | 102 | 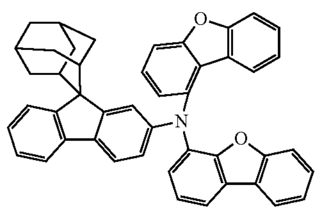 [SMILES: c1ccc2c(c1)-c1ccc(N(c3cccc4c3oc3ccccc34)c3cccc4oc5ccccc5c34)cc1C21C2CC3CC(C2)CC1C3] | | | | 75 | 634.3 |
| 12 | 161 | 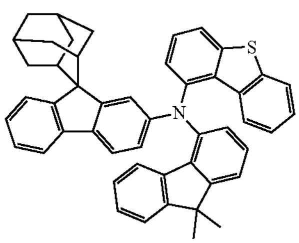 [SMILES: CC1(C)c2ccccc2-c2c(N(c3ccc4c(c3)C3(c5ccccc5-4)C4CC5CC(C4)CC3C5)c3cccc4sc5ccccc5c34)cccc21] | | | | 80 | 676.3 |

Synthesis Example 13: Synthesis of Compound 24

Synthesis of Intermediate IM 2-2:

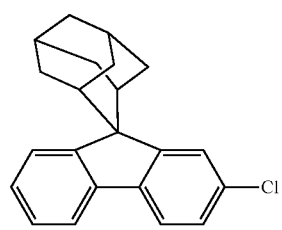

IM 2-2

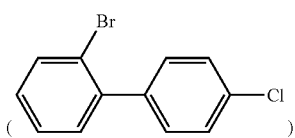 [SMILES: Clc1ccc(-c2ccccc2Br)cc1]

to give intermediate IM 2-2 (137 g. yield: 80%).

Intermediate IM 2-2 was synthesized with reference to the method of steps (1) and (2) in Synthesis Example 1, except that the raw material Sub 1 in step (1) was replaced with 2-bromo-4'-chloro-1,1'-biphenyl

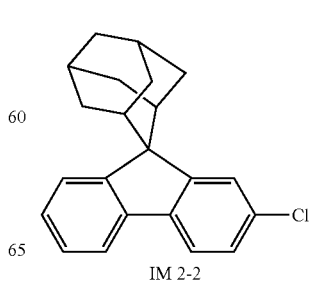

IM 2-2

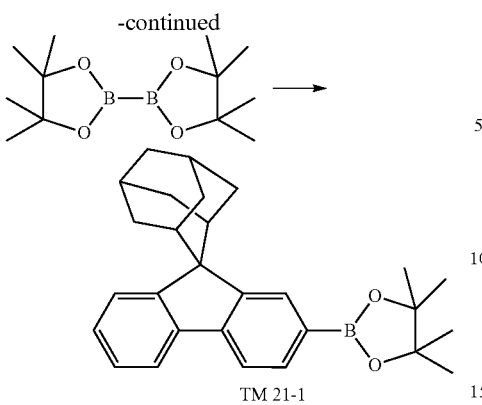

TM 21-1

Step I: Under the protection of nitrogen, 4.8 g (15 mmol) of the intermediate IM 2-2, 2.3 g (9 mmol) of bis(pinacolato)diboron, 2.9 g (30.0 mmol) of potassium acetate (KAc), 0.11 g (0.15 mmol) of PdCl₂(dppf) and 29 mL of dioxane were added into a three-necked flask, the flask was heat to 101° C., and reacted under reflux for 24 h. The reaction solution was washed with water, extracted three times with ethyl acetate, and separate. Organic phase was dried with magnesium sulfate, and then the magnesium sulfate was filtered off. The filtrate was distilled under reduced pressure to remove the solvent. The obtained solid was dissolved with a mixed solvent of dichloromethane and n-heptane at a ratio of 1:5 (at a volume ratio), then the obtained crude was purified by column chromatography to obtain Intermediate IM 21-1 (4.8 g, yield: 77%).

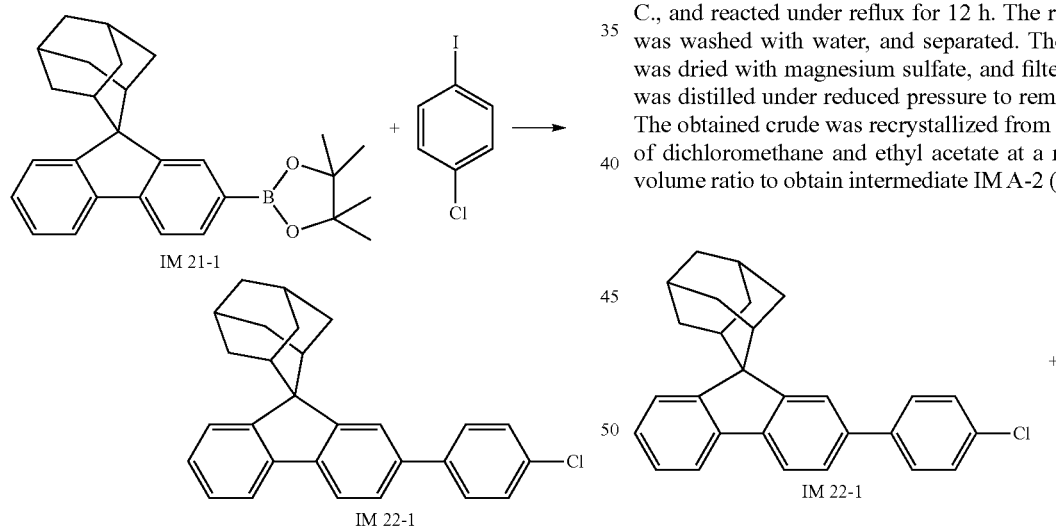

IM 21-1

IM 22-1

Step II: under the protection of nitrogen, a mixture of 4.8 g (11.6 mmol) intermediate IM 21-1, 2.8 g (11.6 mmol) of p-chloroiodobenzene, 0.13 g (0.12 mmol) of tetrakis(triphenylphosphine)palladium, 0.04 g (0.12 mmol) tetrabutylammonium bromide and 3.2 g (23.3 mmol) potassium carbonate was added to a three-necked flask, and 29 mL/10 mL of toluene/water-mixing solvent was added into the flask. The mixture was heated under stirring to 80° C., and reacted for 12 hours. The reaction solution was washed with water, extracted with toluene, and separated. Organic phase was dried with magnesium sulfate, and then the magnesium sulfate was removed by filtration. The filtrate was distilled under reduced pressure to remove the solvent. The obtained solid was recrystallized from dichloromethane to obtain intermediate IM 22-1 (3.7 g, yield: 81%).

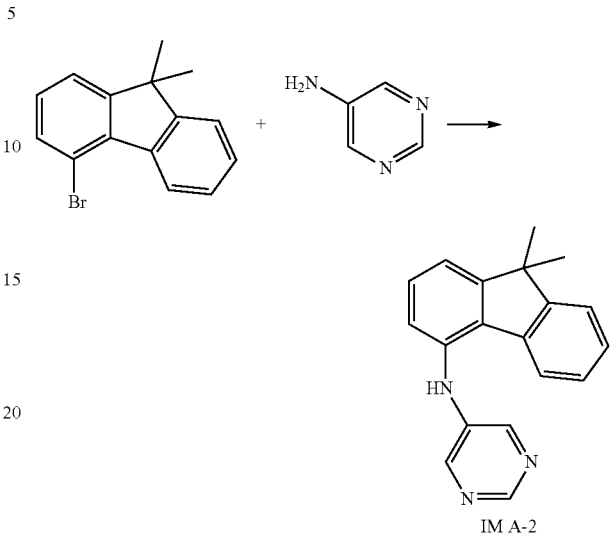

IM A-2

Step III: Under the protection of nitrogen, 3.7 g (13.5 mmol) of 4-bromo-9,9'-dimethylfluorene, 1.3 g (13.5 mmol) of 5-aminopyrimidine, 0.12 g (0.14 mmol) of tris(dibenzylideneacetone)dipalladium, 0.13 g (0.27 mmol) of 2-dicyclohexylphosphino-2',4',6'-triisopropylbiphenyl, 2.6 g (27 mmol) of sodium tert-butoxide, and 40 mL of toluene were added to a three-necked flask, the flask was heated to 110° C., and reacted under reflux for 12 h. The reaction solution was washed with water, and separated. The organic phase was dried with magnesium sulfate, and filtered. The filtrate was distilled under reduced pressure to remove the solvent. The obtained crude was recrystallized from a mixed solvent of dichloromethane and ethyl acetate at a ratio of 1:1 at a volume ratio to obtain intermediate IM A-2 (3.2 yield: 83%).

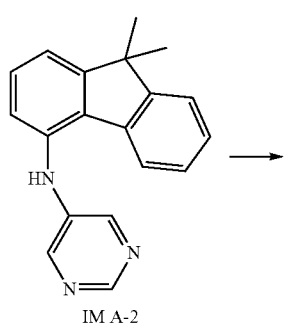

IM A-2

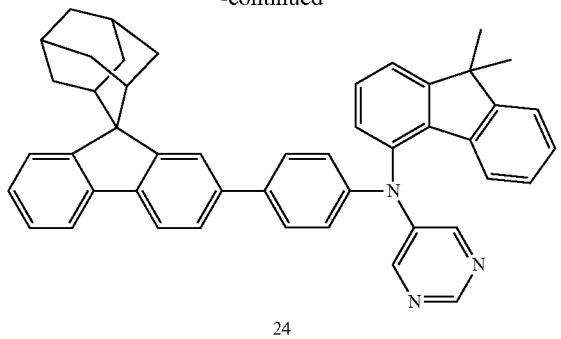

24

Step IV: Under the protection of nitrogen, 3.2 g (8 mmol) of intermediate IM 22-1, 2.3 g (8 mmol) of intermediate IM A-2, 0.07 g (0.08 mmol) of tris(dibenzylideneacetone)dipalladium, 0.06 g (0.16 mmol) of 2-dicyclohexylphosphino-2', 6'-dimethoxybiphenyl, 1.5 g of (16 mmol) of sodium tert-butoxide, and 30 mL of toluene were added to a three-necked flask, the flask was heated to 110° C., and reacted under reflux for 8 h. The reaction solution was cooled to room temperature, washed with water, and separated. The organic phase was dried with magnesium sulfate, and then filtered. The filtrate was distilled under reduced pressure to remove the solvent. The obtained crude was recrystallized from toluene to obtain Compound 24 (2.8 g, yield: 54%). Mass spectrometry: m/z=648.3[M+H]$^+$.

Synthesis Examples 14 to 19

The compounds shown in Table 2 were synthesized with reference to the method of Synthesis Example 13, except that the p-chloroiodobenzene in step II was replaced with the raw material Sub A; the 4-bromo-9,9'-dimethylfluorene of step III was replaced with the raw material Sub II, and 5-aminopyrimidine was replaced with the raw material Sub III. The used main raw materials, and the yield from individual final step and the mass spectrometry results of compounds are shown in Table 2.

TABLE 2

| Synthesis Example | Compound No. | Compound Structure | Sub A | Sub II | Sub III | yield (%) | mass spectrum [M + H]$^+$ |
|---|---|---|---|---|---|---|---|
| 14 | 25 | 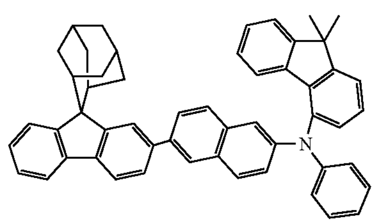 [SMILES: CC1(C)c2ccccc2-c2c(N(c3ccccc3)c3ccc4cc(-c5ccc6c(c5)C5(c7ccccc7-6)C6CC7CC(C6)CC5C7)ccc4c3)cccc21] | Cl-naphthyl-Br | 4-Br-9,9-dimethylfluorene | H$_2$N-phenyl | 63 | 696.4 |
| 15 | 27 | 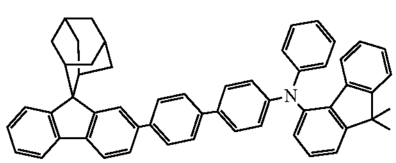 [SMILES: CC1(C)c2ccccc2-c2c(N(c3ccccc3)c3ccc(-c4ccc(-c5ccc6c(c5)C5(c7ccccc7-6)C6CC7CC(C6)CC5C7)cc4)cc3)cccc21] | I-biphenyl-Cl | N-phenyl-fluorenyl | | 72 | 722.4 |
| 16 | 47 | 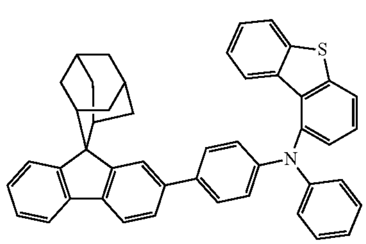 [SMILES: c1ccc(N(c2ccc(-c3ccc4c(c3)C3(c5ccccc5-4)C4CC5CC(C4)CC3C5)cc2)c2cccc3sc4ccccc4c23)cc1] | I-phenyl-Cl | Br-dibenzothiophene | | 77 | 636.3 |
| 17 | 49 | 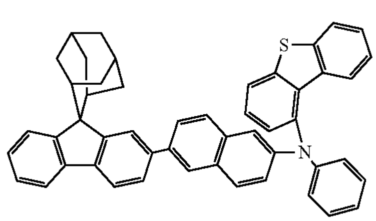 [SMILES: c1ccc(N(c2ccc3cc(-c4ccc5c(c4)C4(c6ccccc6-5)C5CC6CC(C5)CC4C6)ccc3c2)c2cccc3sc4ccccc4c23)cc1] | Cl-naphthyl-Br | Br-dibenzothiophene | | 78 | 686.3 |

TABLE 2-continued

| Synthesis Example | Compound No. | Compound Structure | Sub A | Sub II | Sub III | yield (%) | mass spectrum [M + H]+ |
|---|---|---|---|---|---|---|---|
| 18 | 67 | 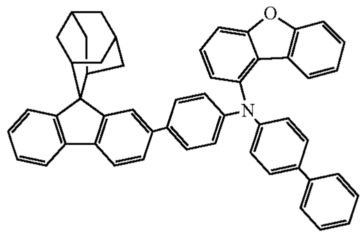 [SMILES: c1ccc(-c2ccc(N(c3ccc(-c4ccc5c(c4)C4(c6ccccc6-5)C5CC6CC(C5)CC4C6)cc3)c3cccc4oc5ccccc5c34)cc2)cc1] | I-C6H4-Cl | Br-dibenzofuran | H2N-biphenyl | 68 | 696.3 |
| 19 | 69 | 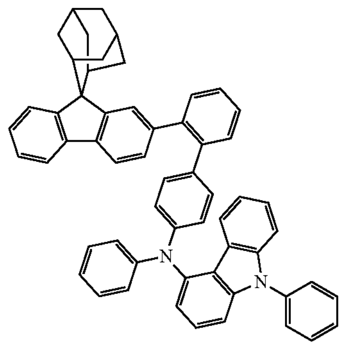 [SMILES: c1ccc(N(c2ccc(-c3ccccc3-c3ccc4c(c3)C3(c5ccccc5-4)C4CC5CC(C4)CC3C5)cc2)c2cccc3c2c2ccccc2n3-c2ccccc2)cc1] | 2-Br-2'-Cl-biphenyl | 1-Br-4-phenylcarbazole | H2N-Ph | 65 | 771.4 |

Synthesis Examples 20 to 25

Synthesis of Intermediate IM 2-3:

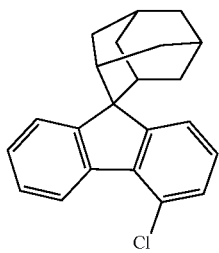

IM 2-3

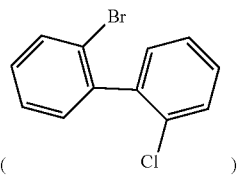 [SMILES: Clc1ccccc1-c1ccccc1Br]

The intermediate IM 2-3 was synthesized with reference to the method of steps (1) and (2) in Synthesis Example 1, except that the raw material Sub 1 in step (1) was replaced with 2-bromo-2'-chloro-1,1'-biphenyl to obtain intermediate IM 2-3 (103 g, yield: 76%).

The compounds shown in Table 3 were synthesized with reference to the method of Synthesis Example 1, except that the synthesis was started from the step (3), the 4-bromo-9,9'-dimethylfluorene in step (3) was replaced with the raw material Sub II, the aniline was replaced with the raw material Sub III, and the intermediate IM 2-1 in step (4) was replaced with the intermediate IM 2-3. The used main raw materials, and the yield from individual final step and mass spectrometry results of compounds are shown in Table 3.

TABLE 3

| Synthesis Example | Compound No. | Structure | IM 2-3 | Sub II | Sub III | yield (%) | mass spectrum [M + H]+ |
|---|---|---|---|---|---|---|---|
| 20 | 125 | 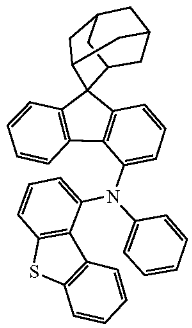 [SMILES: c1ccc(N(c2cccc3c2-c2ccccc2C32C3CC4CC(C3)CC2C4)c2cccc3sc4ccccc4c23)cc1] | | | | 55 | 560.2 |
| 21 | 126 | 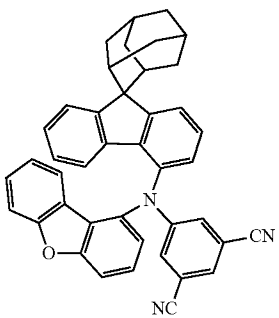 [SMILES: N#Cc1cc(C#N)cc(N(c2cccc3c2-c2ccccc2C32C3CC4CC(C3)CC2C4)c2cccc3oc4ccccc4c23)c1] | | | | 82 | 594.3 |
| 22 | 127 | 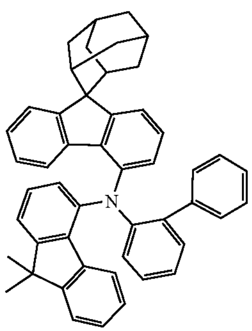 [SMILES: CC1(C)c2ccccc2-c2c(N(c3ccccc3-c3ccccc3)c3cccc4c3-c3ccccc3C43C4CC5CC(C4)CC3C5)cccc21] | | | | 63 | 646.3 |

TABLE 3-continued

| Synthesis Example | Compound No. | Structure | IM 2-3 | Sub II | Sub III | yield (%) | mass spectrum [M + H]+ |
|---|---|---|---|---|---|---|---|
| 23 | 128 | 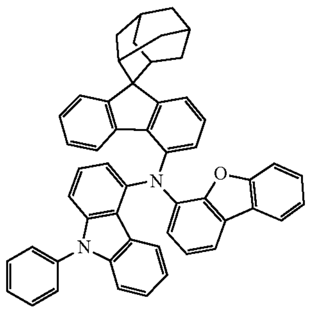 [SMILES: c1ccc(-n2c3ccccc3c3c(N(c4cccc5c4-c4ccccc4C54C5CC6CC(C5)CC4C6)c4cccc5c4oc4ccccc45)cccc32)cc1] | | | | 71 | 709.3 |
| 24 | 130 | 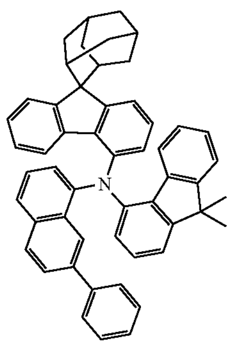 [SMILES: CC1(C)c2ccccc2-c2c(N(c3cccc4c3-c3ccccc3C43C4CC5CC(C4)CC3C5)c3cccc4ccc(-c5ccccc5)cc34)cccc21] | | | | 48 | 696.4 |
| 25 | 192 | 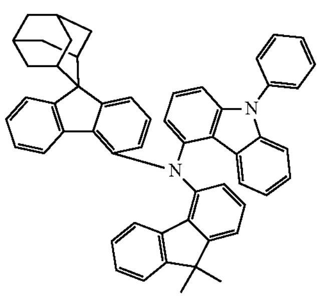 [SMILES: CC1(C)c2ccccc2-c2c(N(c3cccc4c3-c3ccccc3C43C4CC5CC(C4)CC3C5)c3cccc4c3c3ccccc3n4-c3ccccc3)cccc21] | | | | 66 | 735.4 |

Synthesis Examples 26 to 30

The compounds shown in Table 4 were synthesized with reference to the method of Synthesis Example 13, except that the intermediate IM 2-2 of step I was replaced with the intermediate IM 2-3, and the p-chloroiodobenzene of step 11 was replaced with the raw material Sub A; the 4-bromo-9,9'-dimethylfluorene of step III was replaced with the raw material Sub B, the 5-aminopyrimidine was replaced with the raw material Sub C. The used main raw materials, and the yield from individual final step and mass spectrometry results of compounds are shown in Table 4.

TABLE 4

| Synthesis Example | Compound No. | Structure | Sub A | Sub B | Sub C | Yield (%) | mass spectrum [M + H]+ |
|---|---|---|---|---|---|---|---|
| 26 | 152 | 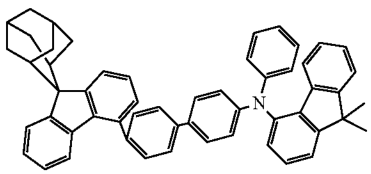 [SMILES: CC1(C)c2ccccc2-c2c(N(c3ccccc3)c3ccc(-c4ccc(-c5cccc6c5-c5ccccc5C65C6CC7CC(C6)CC5C7)cc4)cc3)cccc21] | | | | 70 | 722.4 |
| 27 | 153 | 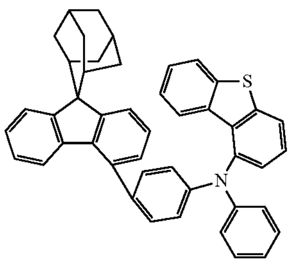 [SMILES: c1ccc(N(c2ccc(-c3cccc4c3-c3ccccc3C43C4CC5CC(C4)CC3C5)cc2)c2cccc3sc4ccccc4c23)cc1] | | | | 72 | 636.3 |
| 28 | 154 | 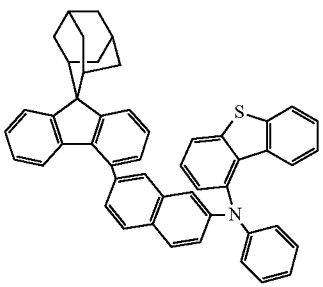 [SMILES: c1ccc(N(c2ccc3ccc(-c4cccc5c4-c4ccccc4C54C5CC6CC(C5)CC4C6)cc3c2)c2cccc3sc4ccccc4c23)cc1] | | | | 71 | 686.3 |

TABLE 4-continued

| Synthesis Example | Compound No. | Structure | Sub A | Sub B | Sub C | Yield (%) | mass spectrum [M + H]⁺ |
|---|---|---|---|---|---|---|---|
| 29 | 155 | 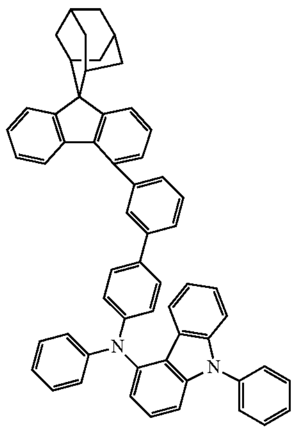 [SMILES: c1ccc(N(c2ccc(-c3cccc(-c4cccc5c4-c4ccccc4C54C5CC6CC(C5)CC4C6)c3)cc2)c2cccc3c2c2ccccc2n3-c2ccccc2)cc1] | | | | 68 | 771.4 |
| 30 | 196 | 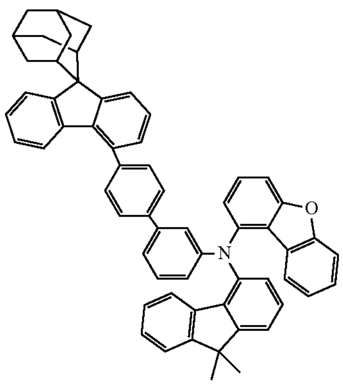 [SMILES: CC1(C)c2ccccc2-c2c(N(c3cccc(-c4ccc(-c5cccc6c5-c5ccccc5C65C6CC7CC(C6)CC5C7)cc4)c3)c3cccc4oc5ccccc5c34)cccc21] | | | | 83 | 812.4 |

NMR data for Compound 153: $^1$H NMR (400 MHz, CD$_2$Cl$_2$): 8.55 (d, 1H), 8.09-7.91 (d, 2H), 7.74-7.71 (m, 2H), 7.61 (d, 4H), 7.55 (d, 4H), 7.43 (t, 4H), 7.21-7.05 (m, 6H), 2.91 (d, 2H), 2.61 (d, 2H$_1$), 2.16 (s, 1H), 1.90 (s, 3H), 1.77 (d, 2H), 1.69 (d, 2H), 1.60 (s, 2H) ppm.

Blue organic electroluminescent devices were manufactured using the following methods.

Example 1

An ITO substrate (manufactured by Corning) with an ITO thickness of 1500 Å was cut into a size of 40 mm (length)× 40 mm (width)×0.7 mm (thickness), and prepared into an experimental substrate having a cathode overlap region, an anode, and an insulating layer pattern by a photolithography process. Surfaces of the experimental substrate were treated using ultraviolet ozone and O$_2$:N$_2$ plasma, to increase work function of the anode (experimental substrate) and remove dross.

A hole injection layer (HIL) with a thickness of 100 Å was formed by vacuum evaporation of m-MTDATA on the experimental substrate (anode), and a first hole transporting layer (HTL1) with a thickness of 950 Å was formed by vacuum evaporation of TCTA on the hole injection layer.

A second hole transporting layer with a thickness of 150 Å was formed by vacuum evaporation of Compound 1 on the first hole transporting layer.

A light-emitting layer (EML) with a thickness of 220 Å was formed by using α,β-ADN as a host with doping BD-1 at a film thickness ratio of 100:3.

An electron transporting layer (ETL) with a thickness of 300 Å was formed by mixing and evaporating DBimiBphen and LiQ at a weight ratio of 1:1, and an electron injection layer (EIL) with a thickness of 10 Å was formed by evaporating LiQ on the electron transporting layer, and then a cathode with a thickness of 120 Å was formed by mixing and vacuum-evaporating magnesium (Mg) and silver (Ag) at an evaporation rate of 1:9 on the electron injection layer.

A CP-1 with a thickness of 650 Å was vacuum-evaporated on the cathode to complete the manufacturing of the blue organic light-emitting device.

Examples 2 to 30

A corresponding blue organic electroluminescent device was prepared in the same manner as in Example 1 except that using a second hole transporting layer material (HTL2 material) listed in Table 6 instead of Compound 1 in Example 1.

Comparative Examples 1 to 4

A blue organic electroluminescent device was prepared in the same manner as in Example 1 except that using NPB, Compound A, Compound B and Compound C instead of Compound 1 in Example 1, respectively.

The structural formulaes of the main materials used in the above Examples and Comparative Examples are shown in Table 5.

TABLE 5

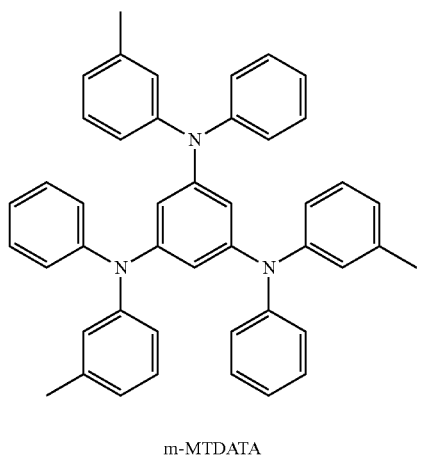

m-MTDATA

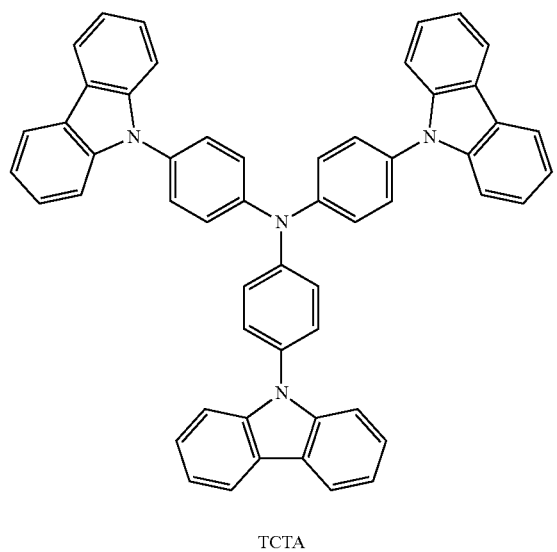

TCTA

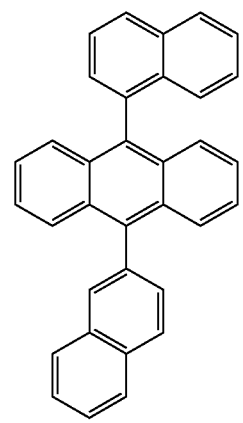 [SMILES: c1ccc2cc(-c3c4ccccc4c(-c4cccc5ccccc45)c4ccccc34)ccc2c1]

α, β-ADN

TABLE 5-continued
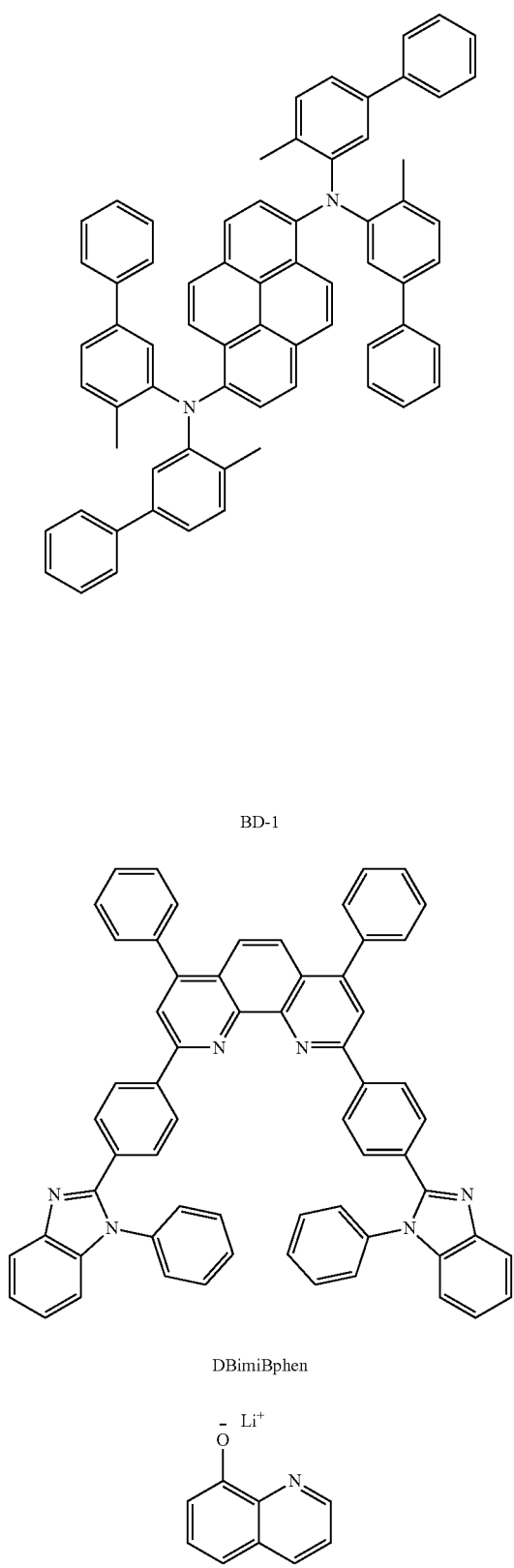
BD-1
DBimiBphen
LiQ
TABLE 5-continued
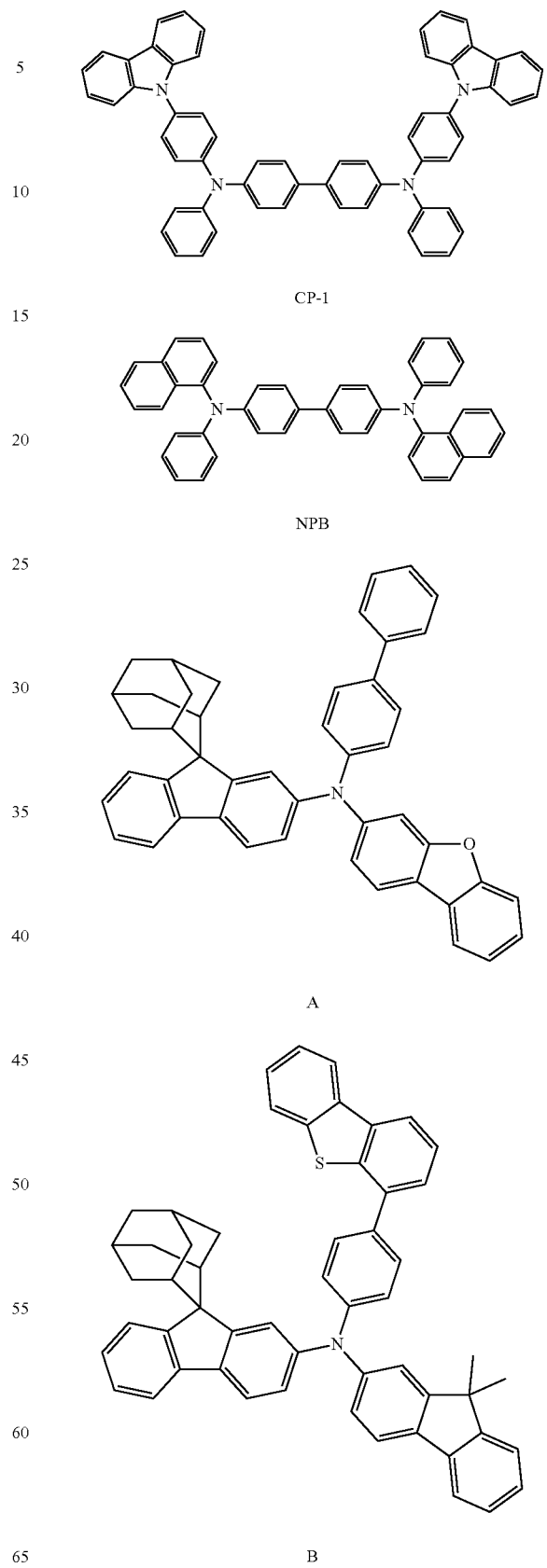
CP-1
NPB
A
B TABLE 5-continued

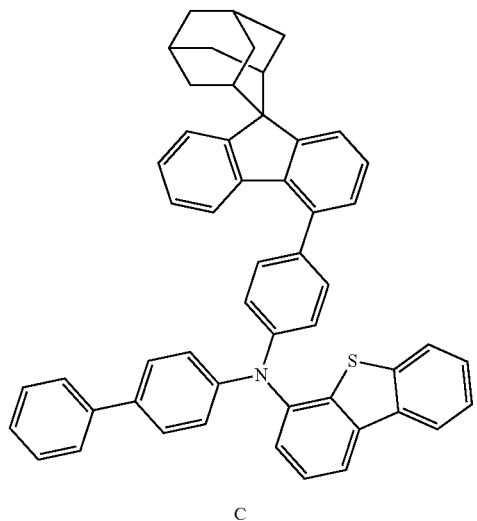

C

For the blue organic electroluminescent devices prepared in Examples 1 to 30 and Comparative Examples 1 to 4, the drive voltages and color coordinates of the devices were tested under a condition of 10 mA/cm$^1$, and the T95 lifetimes of the devices were tested under a condition of 15 mA/cm$^2$. The results are shown in Table 6:

TABLE 6

| No. | HTL2 material | drive voltage (V) | color coordinate CIEy | T95 lifetime (h) |
|---|---|---|---|---|
| Example 1 | Compound 1 | 4.05 | 0.050 | 266 |
| Example 2 | Compound 2 | 4.06 | 0.048 | 268 |
| Example 3 | Compound 5 | 4.09 | 0.048 | 271 |
| Example 4 | Compound 20 | 4.16 | 0.049 | 285 |
| Example 5 | Compound 21 | 4.07 | 0.051 | 267 |
| Example 6 | Compound 30 | 3.90 | 0.048 | 268 |
| Example 7 | Compound 41 | 4.03 | 0.048 | 278 |
| Example 8 | Compound 62 | 3.96 | 0.051 | 273 |
| Example 9 | Compound 72 | 4.09 | 0.048 | 266 |
| Example 10 | Compound 89 | 4.05 | 0.051 | 298 |
| Example 11 | Compound 102 | 3.93 | 0.050 | 297 |
| Example 12 | Compound 161 | 4.01 | 0.050 | 296 |
| Example 13 | Compound 24 | 4.03 | 0.049 | 271 |
| Example 14 | Compound 25 | 4.06 | 0.048 | 275 |
| Example 15 | Compound 27 | 4.00 | 0.050 | 269 |
| Example 16 | Compound 47 | 4.14 | 0.048 | 276 |
| Example 17 | Compound 49 | 4.06 | 0.048 | 300 |
| Example 18 | Compound 67 | 4.11 | 0.049 | 270 |
| Example 19 | Compound 69 | 4.07 | 0.049 | 278 |
| Example 20 | Compound 125 | 4.07 | 0.051 | 279 |
| Example 21 | Compound 126 | 4.14 | 0.051 | 295 |
| Example 22 | Compound 127 | 4.15 | 0.049 | 268 |
| Example 23 | Compound 128 | 4.07 | 0.051 | 295 |
| Example 24 | Compound 130 | 4.05 | 0.050 | 280 |
| Example 25 | Compound 192 | 3.98 | 0.048 | 299 |
| Example 26 | Compound 152 | 4.11 | 0.050 | 275 |
| Example 27 | Compound 153 | 4.09 | 0.050 | 285 |
| Example 28 | Compound 154 | 4.05 | 0.048 | 289 |
| Example 29 | Compound 155 | 4.06 | 0.051 | 280 |
| Example 30 | Compound 196 | 4.02 | 0.049 | 294 |
| Comparative Example 1 | TCTA | 4.23 | 0.047 | 156 |
| Comparative Example 2 | Compound A | 3.98 | 0.048 | 232 |
| Comparative Example 3 | Compound B | 3.99 | 0.049 | 239 |
| Comparative Example 4 | Compound C | 4.02 | 0.048 | 230 |

Therefore, when the nitrogen-containing compound of the present disclosure is used for the second hole transporting layer (electron-blocking layer) of the organic electroluminescent device, the lifetime of the organic electroluminescent device can be effectively increased at an equivalent level of current efficiency. Specifically, compared with Comparative Example 3, which had a better overall effect among Comparative Examples I to 4, the lifetime was improved by at least 11.3%, while having a lower drive voltage. In particular, comparing Examples 1 to 30 with Comparative Examples 2 to 4, it can be seen that in each of the compounds of the examples, at least one of the aromatic groups directly attached to the nitrogen atom is selected from dibenzo-5-membered fused ring bonded at 4-position, thereby improving the thermal stability of the whole compound, and further improving the lifetime of the OLED device when the compound is used as an electron-blocking layer.

Preferred embodiments of the present disclosure have been described in detail above with reference to the accompanying drawings, however, the present disclosure is not limited to the specific details in the above embodiments. A variety of simple variations of the technical solutions of the present disclosure may be made within the scope of the technical concept of the present disclosure, and all of the simple variations fall within the scope of the present disclosure.

It should also be noted that, each of specific technical features described in the above-described embodiments can be combined in any suitable manner without contradiction, and in order to avoid unnecessary repetition, various possible combinations are not separately described in the present disclosure.

In addition, any combination of various embodiments of the present disclosure may be made, as long as it does not depart from the idea of the present disclosure, and it shall also be considered as the disclosure of the present disclosure.

What is claimed is:

1. A nitrogen-containing compound, having a structure represented by Formula 1:

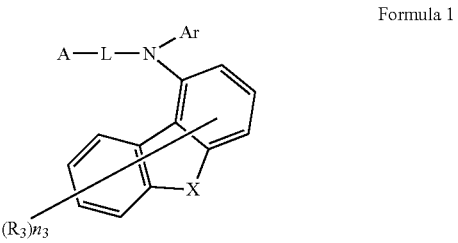

Formula 1 wherein X is selected from O, S, N($R_4$), or C($R_5R_6$), $R_4$ is selected from an aryl with 6 to 12 carbon atoms, or a heteroaryl with 3 to 12 carbon atoms; $R_5$ to $R_6$ are each independently selected from an alkyl with 1 to 4 carbon atoms, or an aryl with 6 to 12 carbon atoms;

Ar is selected from a substituted or unsubstituted aryl with 6 to 26 carbon atoms, or a substituted or unsubstituted heteroaryl with 3 to 24 carbon atoms;

L is selected from single bond, or a substituted or unsubstituted arylene with 6 to 20 carbon atoms;

A has a structure represented by the following Formula 1-1 or Formula 1-2:

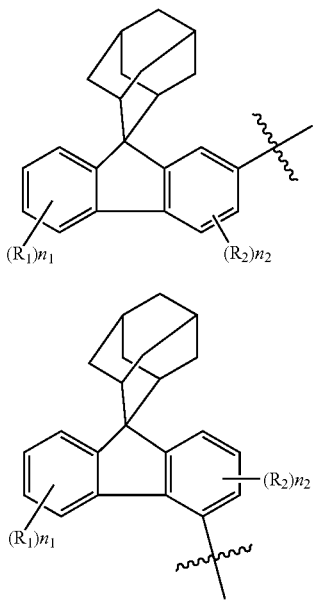

Formula 1-1

Formula 1-2

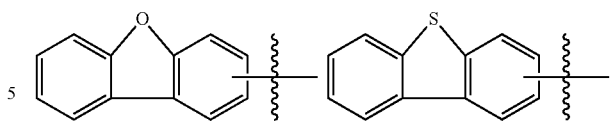
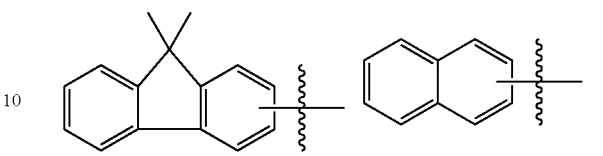
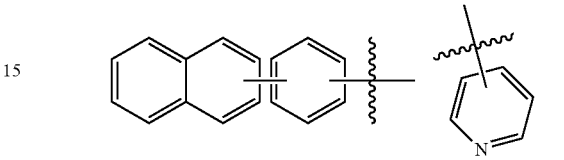
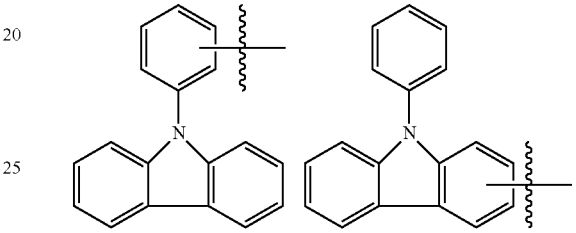
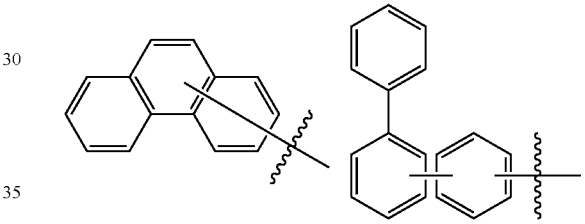

the substituents in L and Ar are the same or different, and are each independently selected from deuterium, fluorine, cyano, an alkyl with 1 to 4 carbon atoms, an alkoxy with 1 to 4 carbon atoms, an alkylthio with 1 to 4 carbon atoms, a haloalkyl with 1 to 4 carbon atoms, a cycloalkyl with 5 to 10 carbon atoms, an aryl with 6 to 15 carbon atoms, a heteroaryl with 5 to 12 carbon atoms, a trialkylsilyl with 3 to 7 carbon atoms, or triphenylsilyl; in L and Ar, optionally, any two adjacent substituents form a ring;

$R_1$ to $R_3$ are the same or different, and are each independently selected from deuterium, fluorine, cyano, an alkyl with 1 to 4 carbon atoms, an alkoxy with 1 to 4 carbon atoms, an alkylthio with 1 to 4 carbon atoms, a fluoroalkyl with 1 to 4 carbon atoms, a cycloalkyl with 5 to 10 carbon atoms, a trialkylsilyl with 3 to 7 carbon atoms, or an aryl with 6 to 12 carbon atoms; and $n_1$, $n_2$ and $n_3$ respectively represent the number of $R_1$, $R_2$ and $R_3$; $R_1$ to $R_3$ are represented by $R_j$, and $n_1$ to $n_3$ are represented by $n_j$, wherein j is a variable representing an integer of 1 to 3; and when j is 1, $n_j$ is selected from 0, 1, 2, 3, or 4; when j is 2, $n_j$ is selected from 0, 1, 2, or 3; when j is 3, $n_j$ is 0, 1, 2, 3, 4, 5, 6, or 7; optionally, any two adjacent $R_j$ form a ring.

2. The nitrogen-containing compound of claim 1, wherein $R_1$ and $R_2$ are each independently selected from deuterium, fluorine, cyano, methyl, ethyl, n-propyl, isopropyl, tert-butyl, methoxy, trifluoromethyl, cyclopentyl, cyclohexyl, trimethylsilyl, phenyl, per or naphthyl.

3. The nitrogen-containing compound of claim 1, wherein Ar is a substituted or unsubstituted group $V_1$, the unsubstituted group $V_1$ is selected from the following groups:

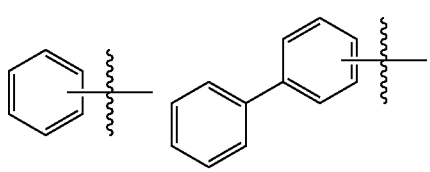

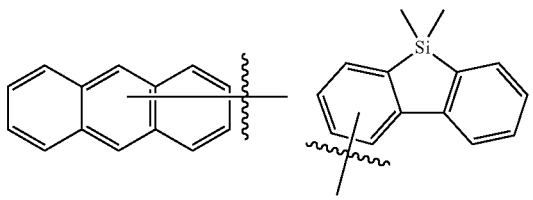
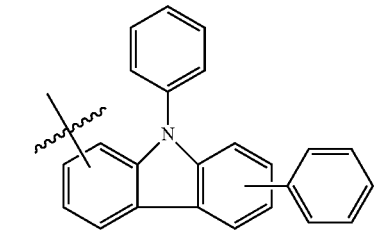
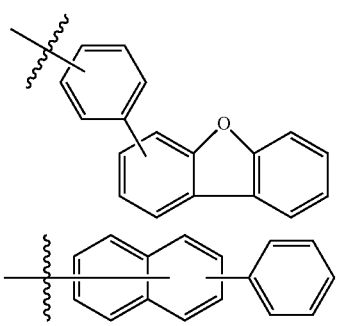

-continued

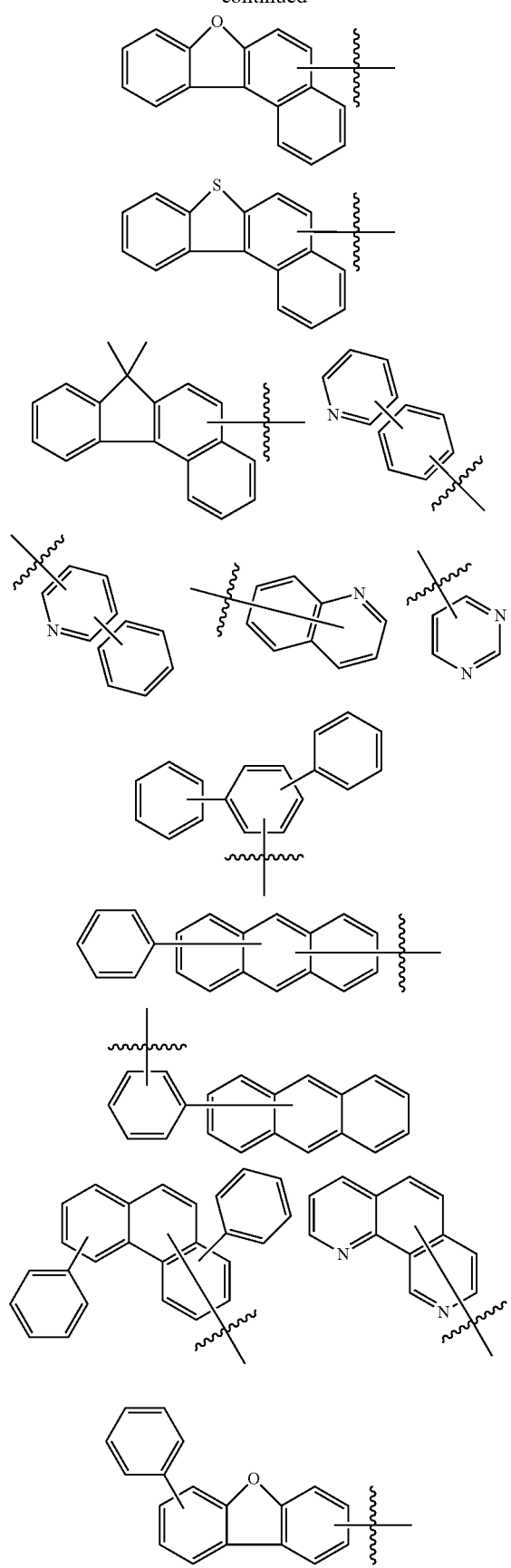

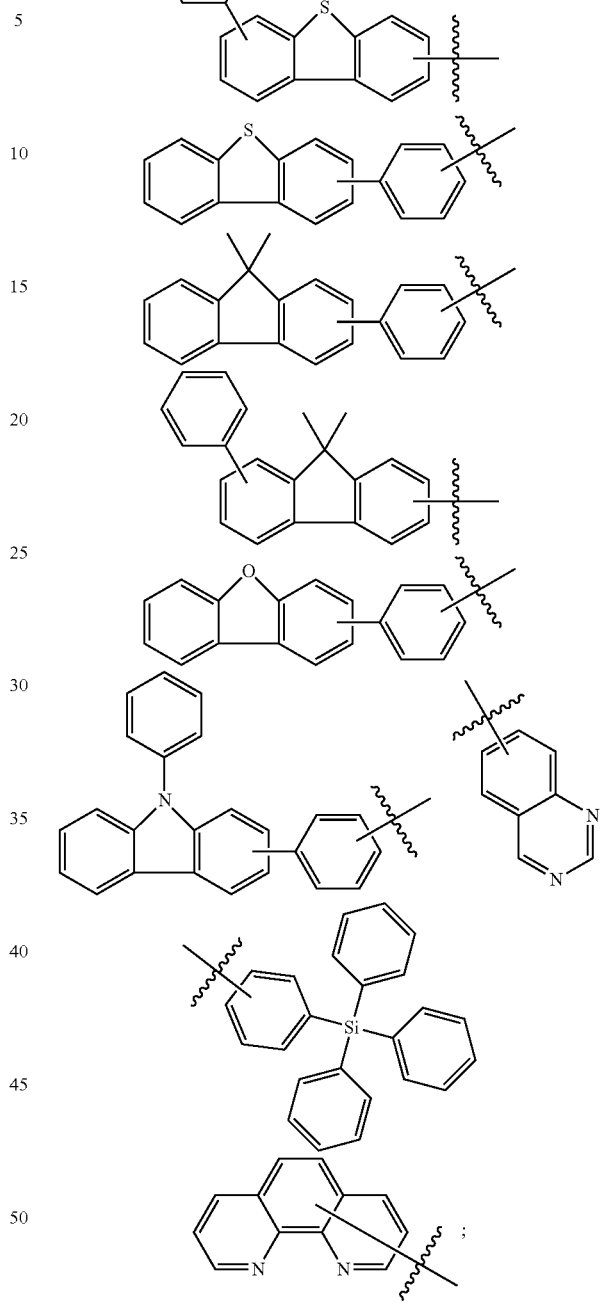

the substituted group $V_1$ has one or two or more substituents, the substituents in the substituted group $V_1$ are independently selected from deuterium, fluorine, cyano, an alkyl with 1 to 4 carbon atoms, an alkoxy with 1 to 4 carbon atoms, an alkylthio with 1 to 4 carbon atoms, a fluoroalkyl with 1 to 4 carbon atoms, a cycloalkyl with 5 to 10 carbon atoms, a trialkylsilyl with 3 to 7 carbon atoms, or pyridyl.

4. The nitrogen-containing compound of claim 1, wherein L is selected from single bond, or a substituted or unsubstituted group $V_2$, the unsubstituted group $V_2$ is selected from the following groups:

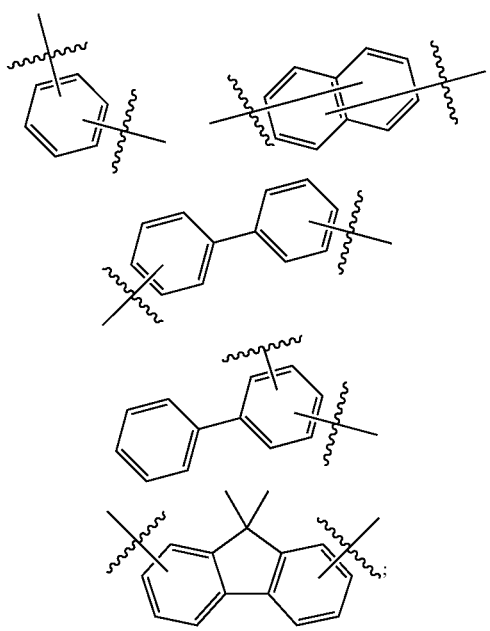

the substituted group $V_2$ has one or two or more substituents, and the substituents in the substituted group $V_2$ are independently selected from deuterium, fluorine, cyano, an alkyl with 1 to 4 carbon atoms, an alkoxy with 1 to 4 carbon atoms, an alkylthio with 1 to 4 carbon atoms, a fluoroalkyl with 1 to 4 carbon atoms, a cycloalkyl with 5 to 10 carbon atoms, a trialkylsilyl with 3 to 7 carbon atoms, an aryl with 6 to 12 carbon atoms, or triphenylsilyl.

5. The nitrogen-containing compound of claim 1, wherein X is selected from O, S, N(Ph), or C(CH$_3$)$_2$, and n$_3$ is selected from 0 or 1; R$_3$ is selected from methyl, tert-butyl, fluorine, cyano, or trimethylsilyl; and Ar is selected from dibenzofuryl, dibenzothiophenyl, 9,9-dimethylfluorenyl, or N-phenylcarbazolyl.

6. The nitrogen-containing compound of claim 1, wherein the nitrogen-containing compound is selected from the following compounds:

1

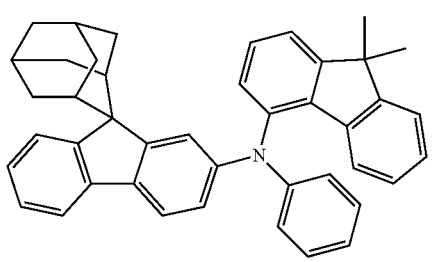

2

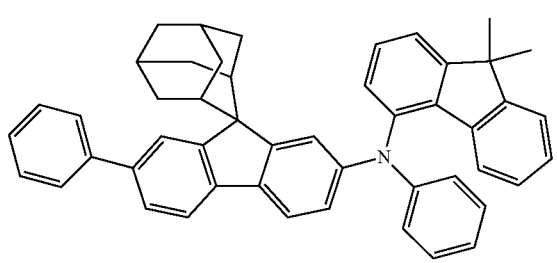

3

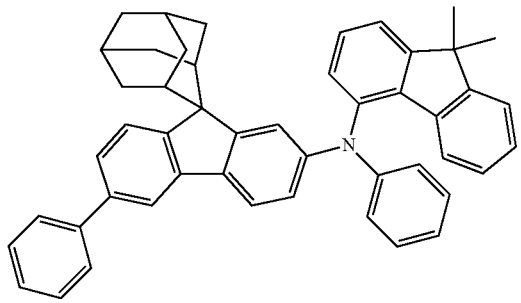

4

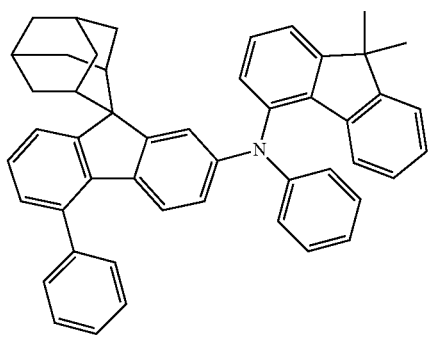

5

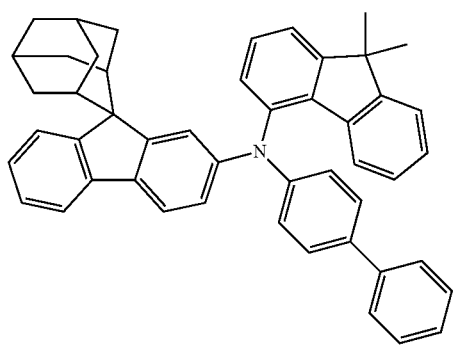

6

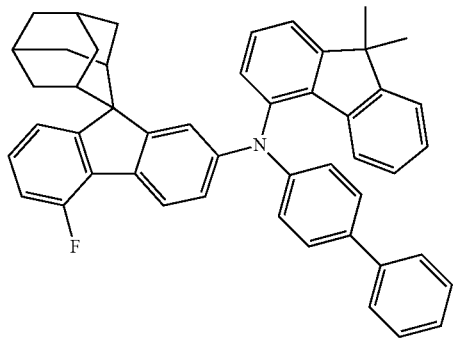

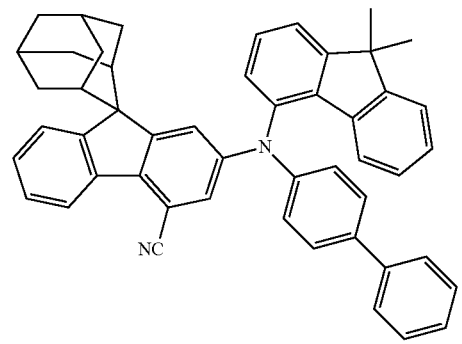
7
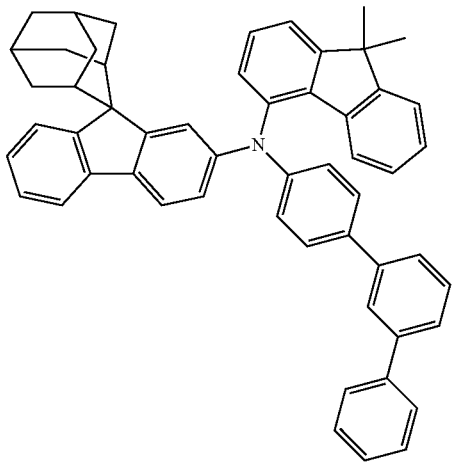
11
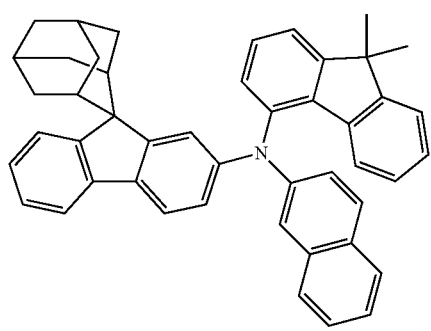
8
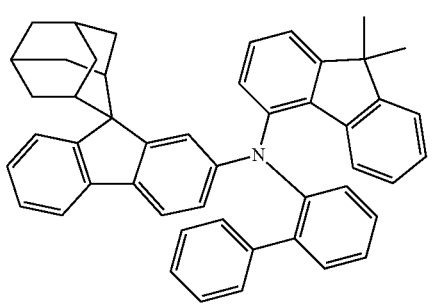
12
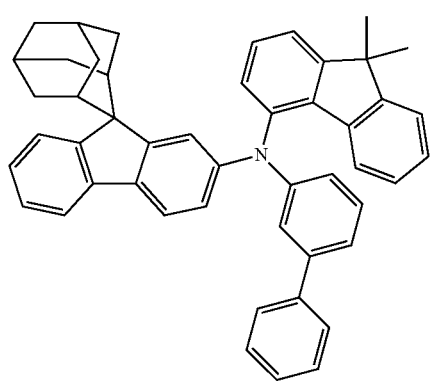
9
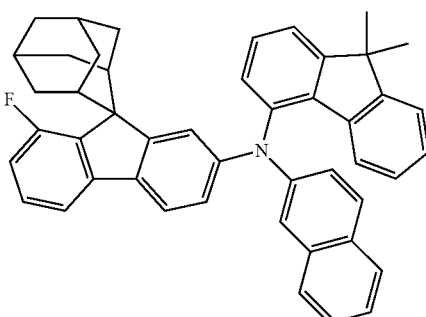
13
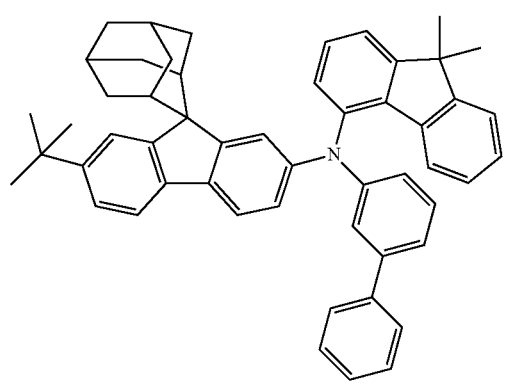
10
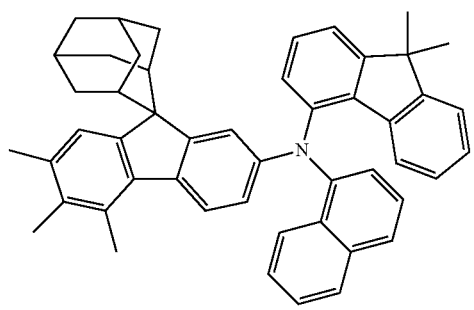
14

149
-continued
15
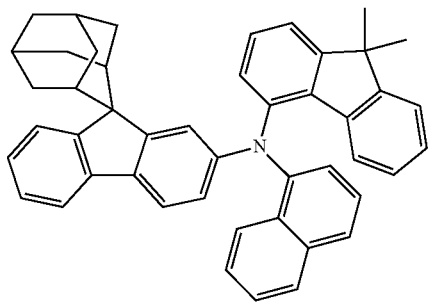
16
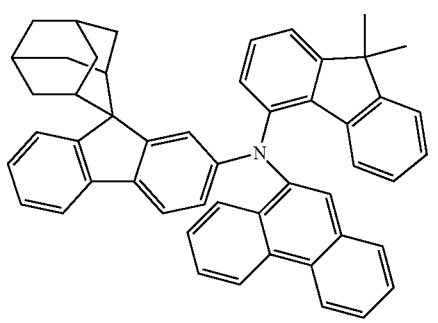
17
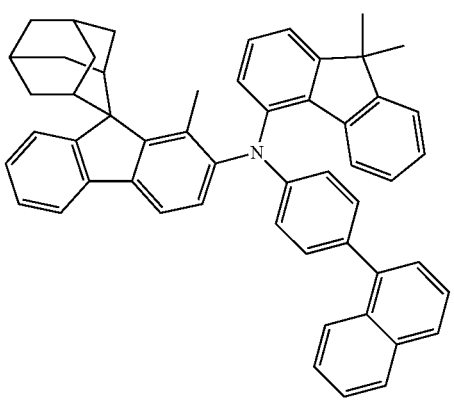
18
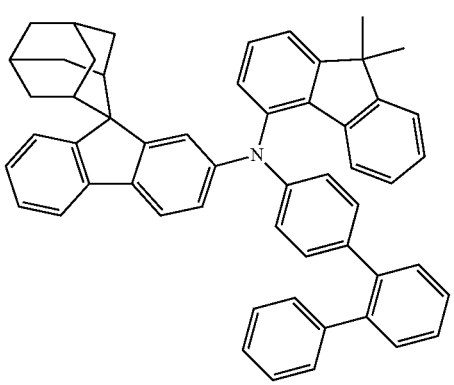
150
-continued
19
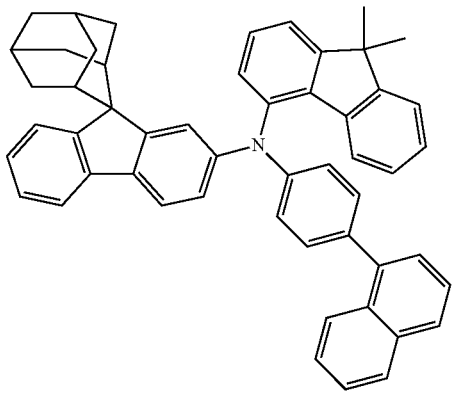
20
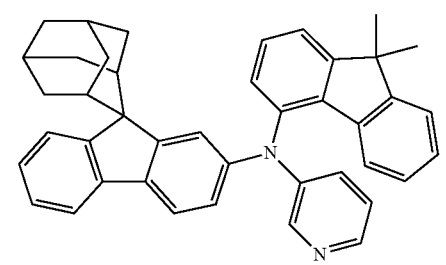
21
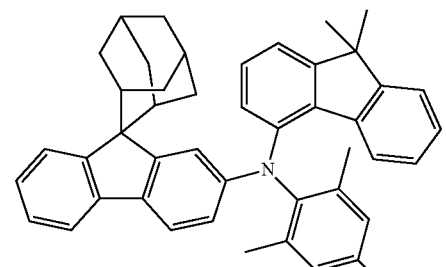
22
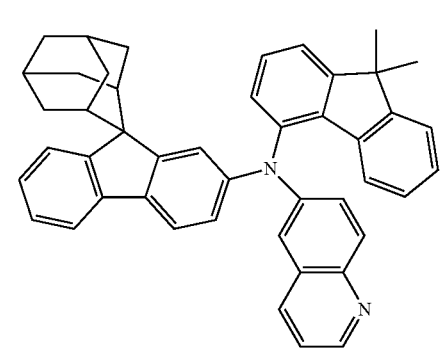
23
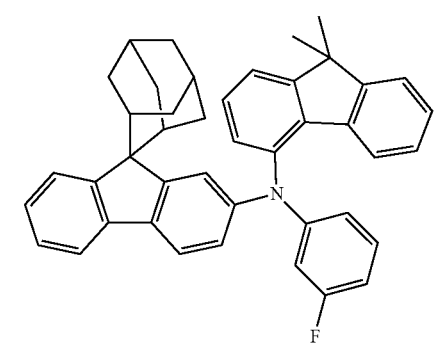

24
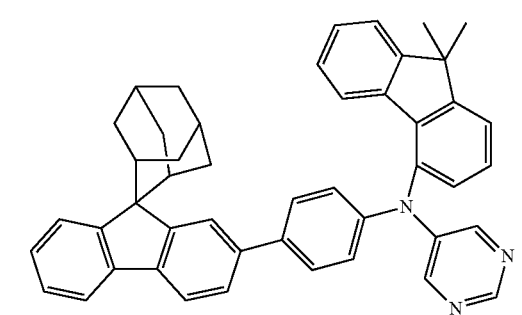
25
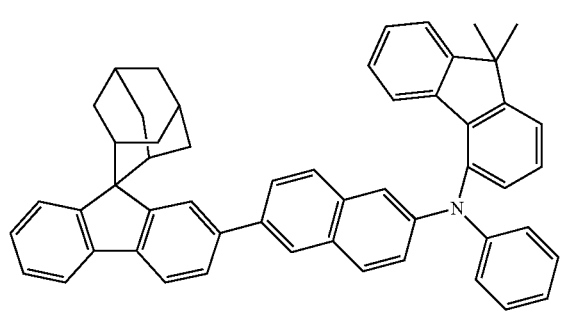
27
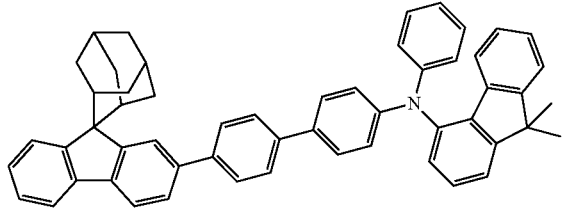
28
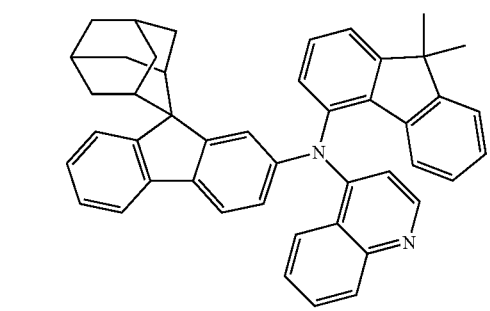
29
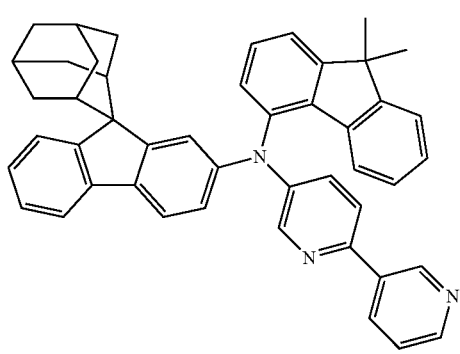
30
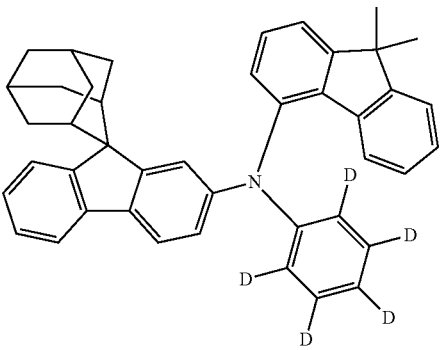
31
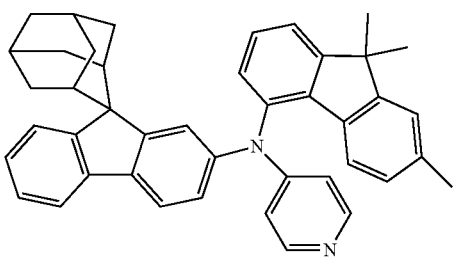
32
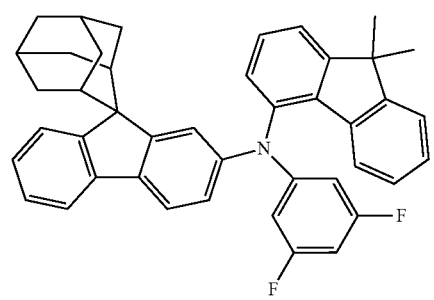
33
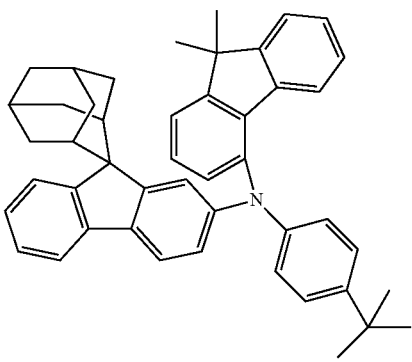
34
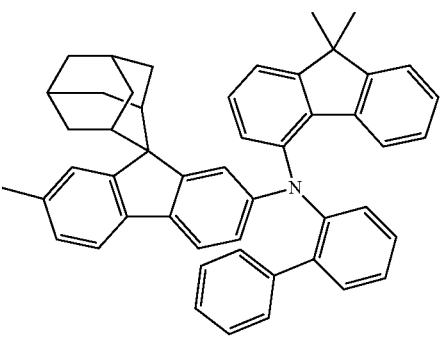

153
-continued
35
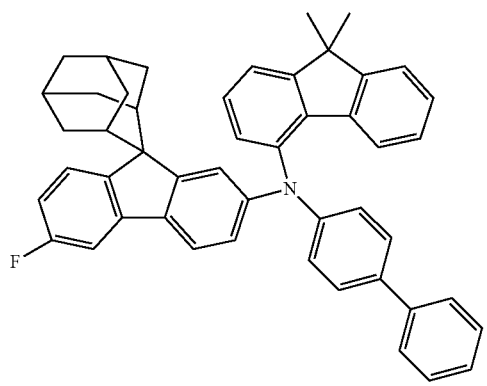
36
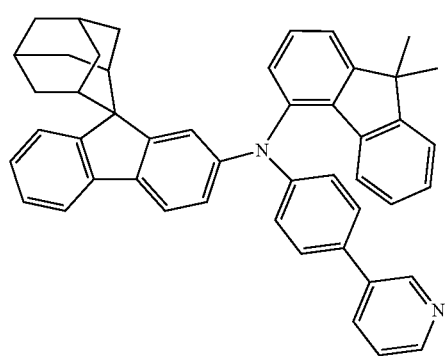
39
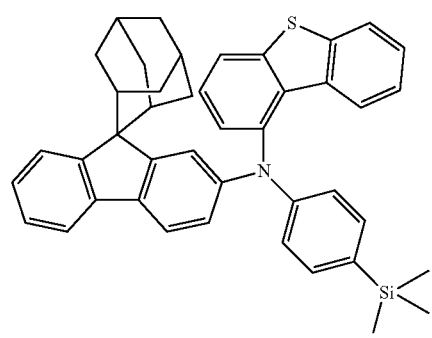
40
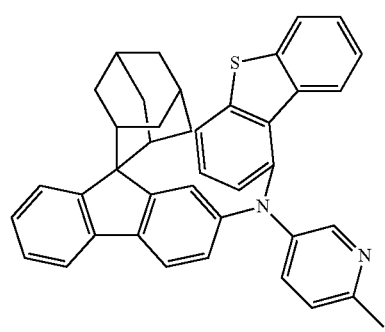
154
-continued
41
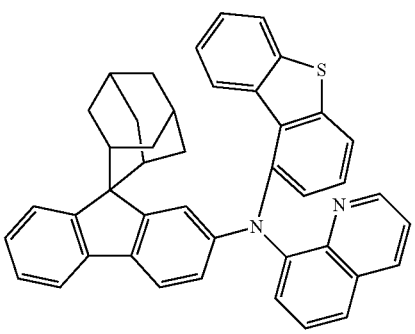
42
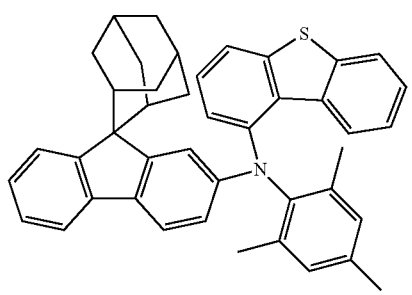
43
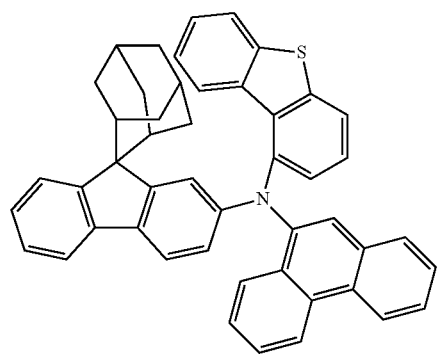
44
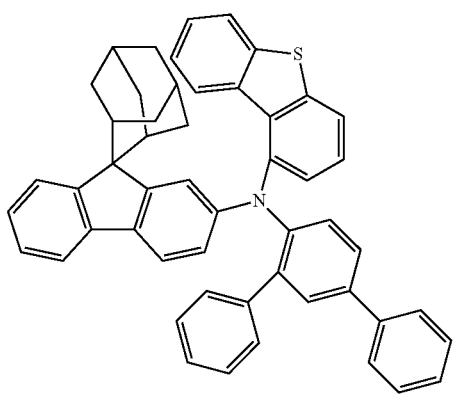

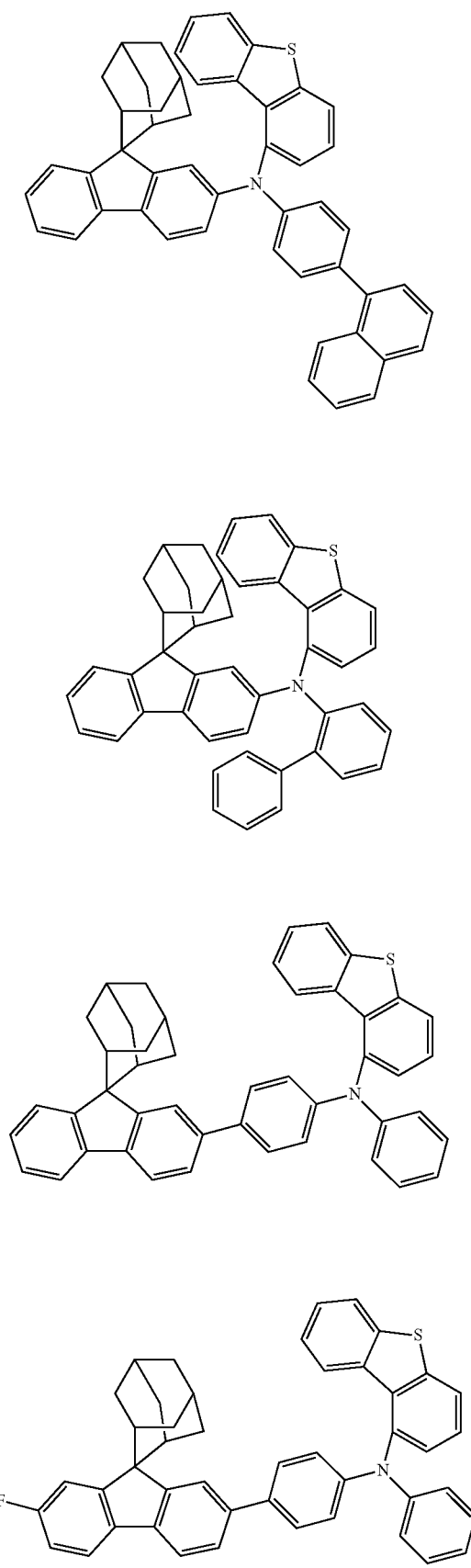
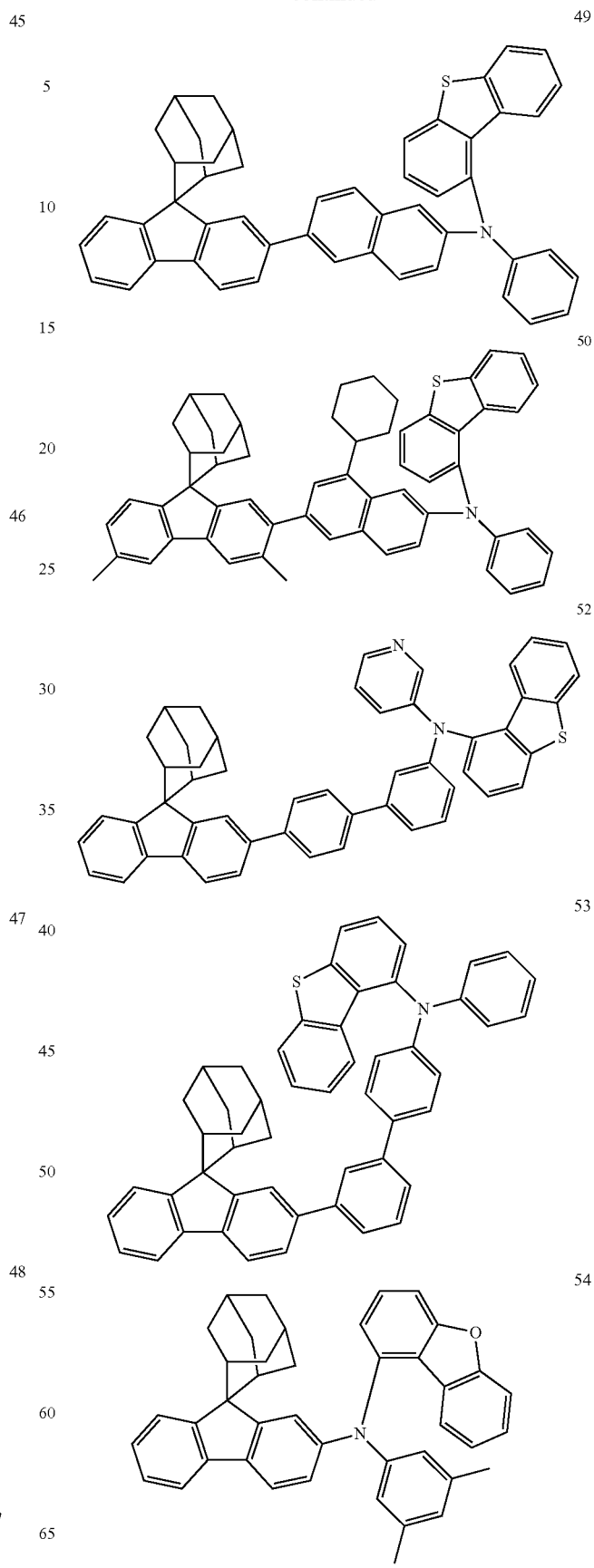

55
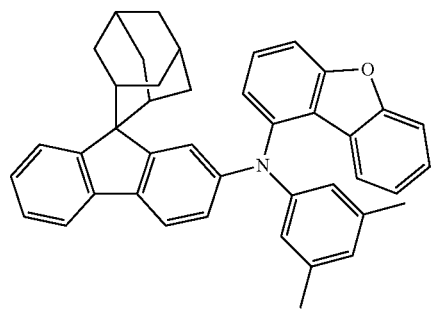
56
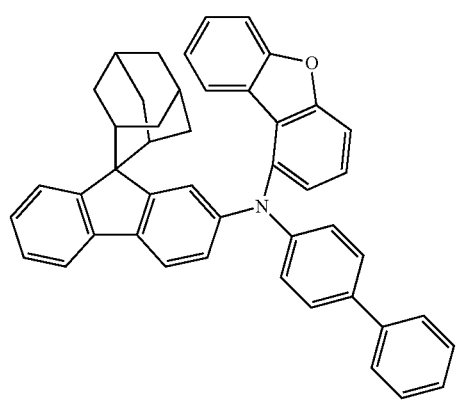
57
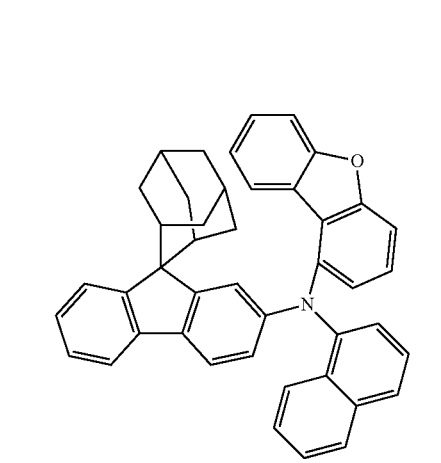
58
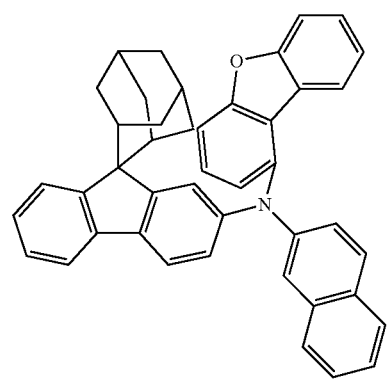
59
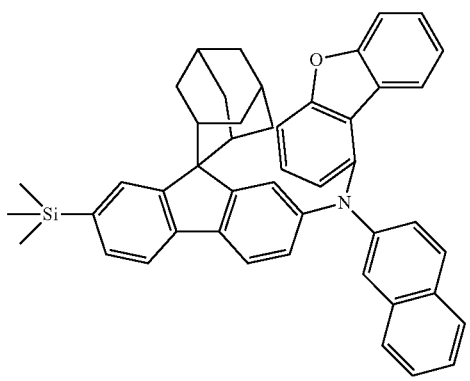
60
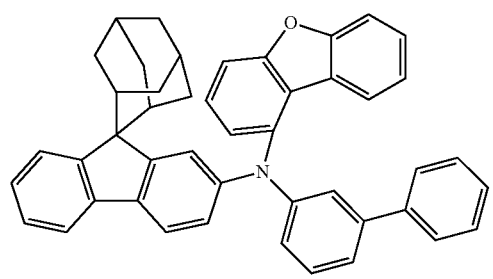
61
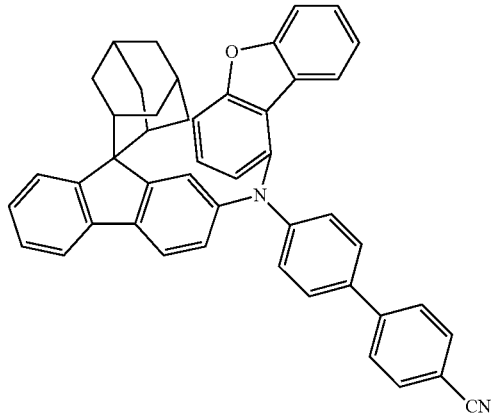
62
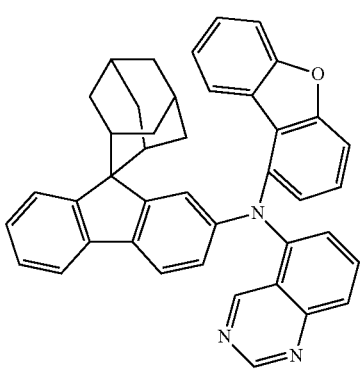

63
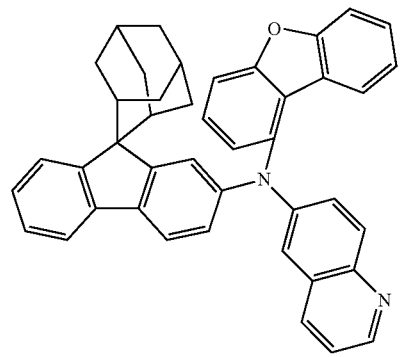
64
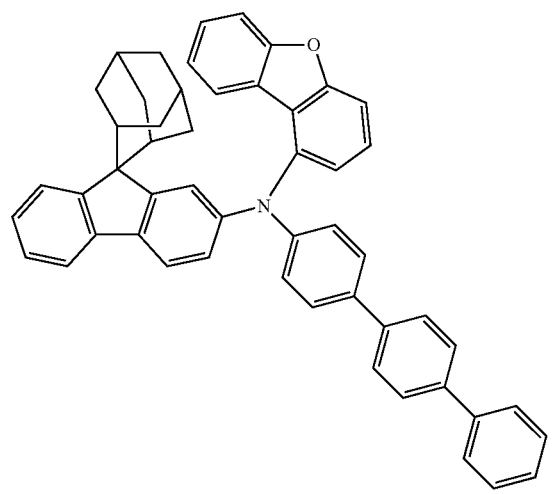
65
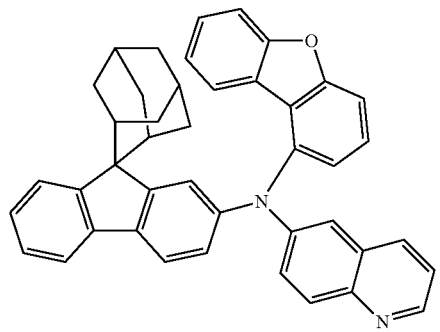
66
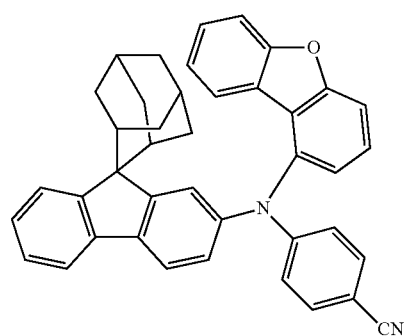
67
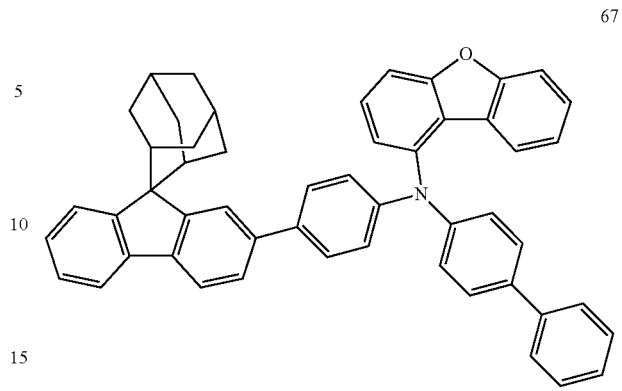
68
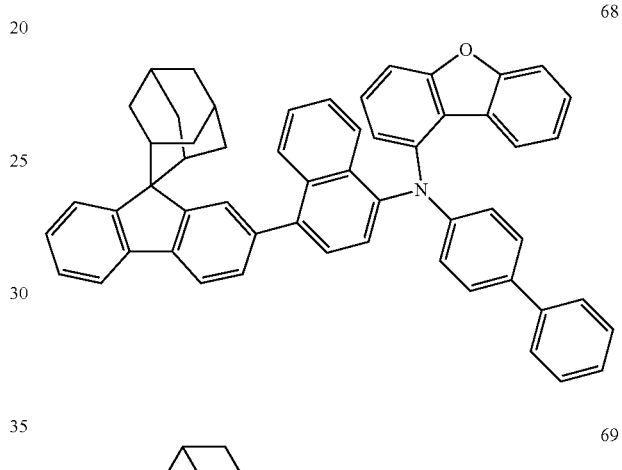
69
70
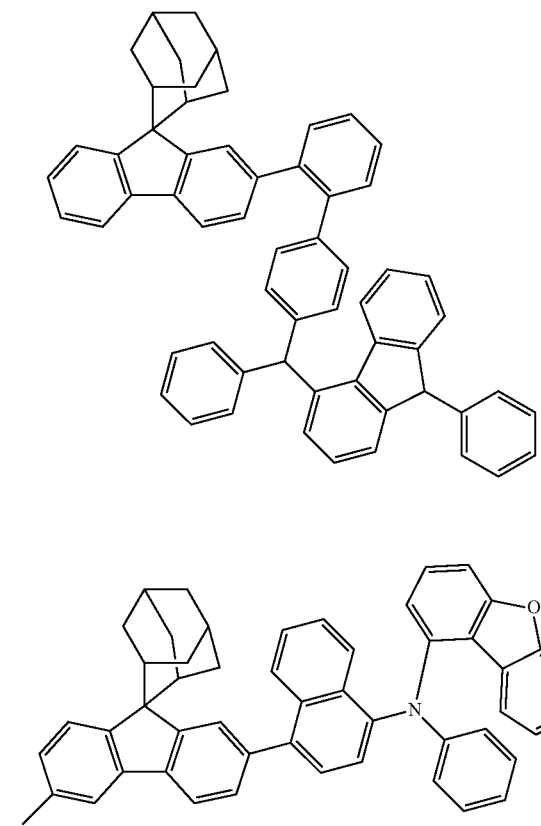

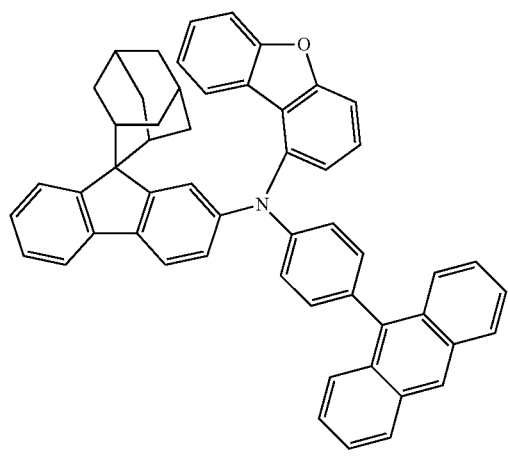
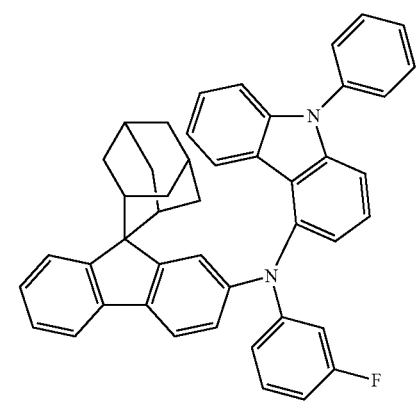
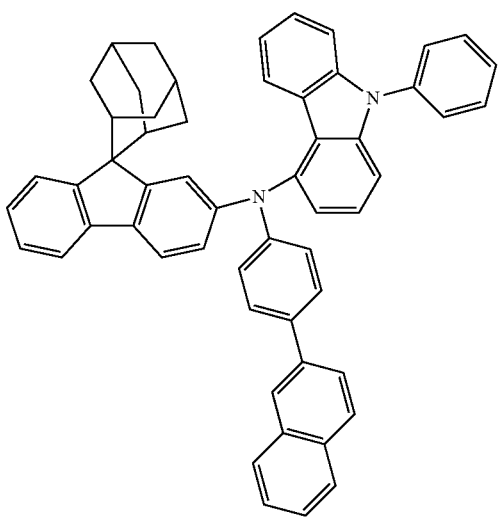
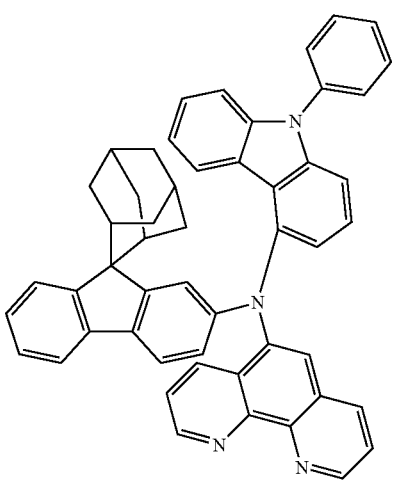
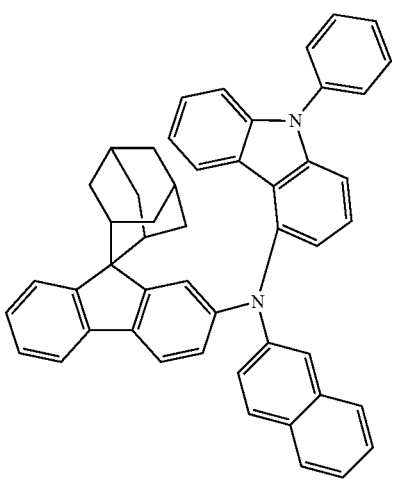

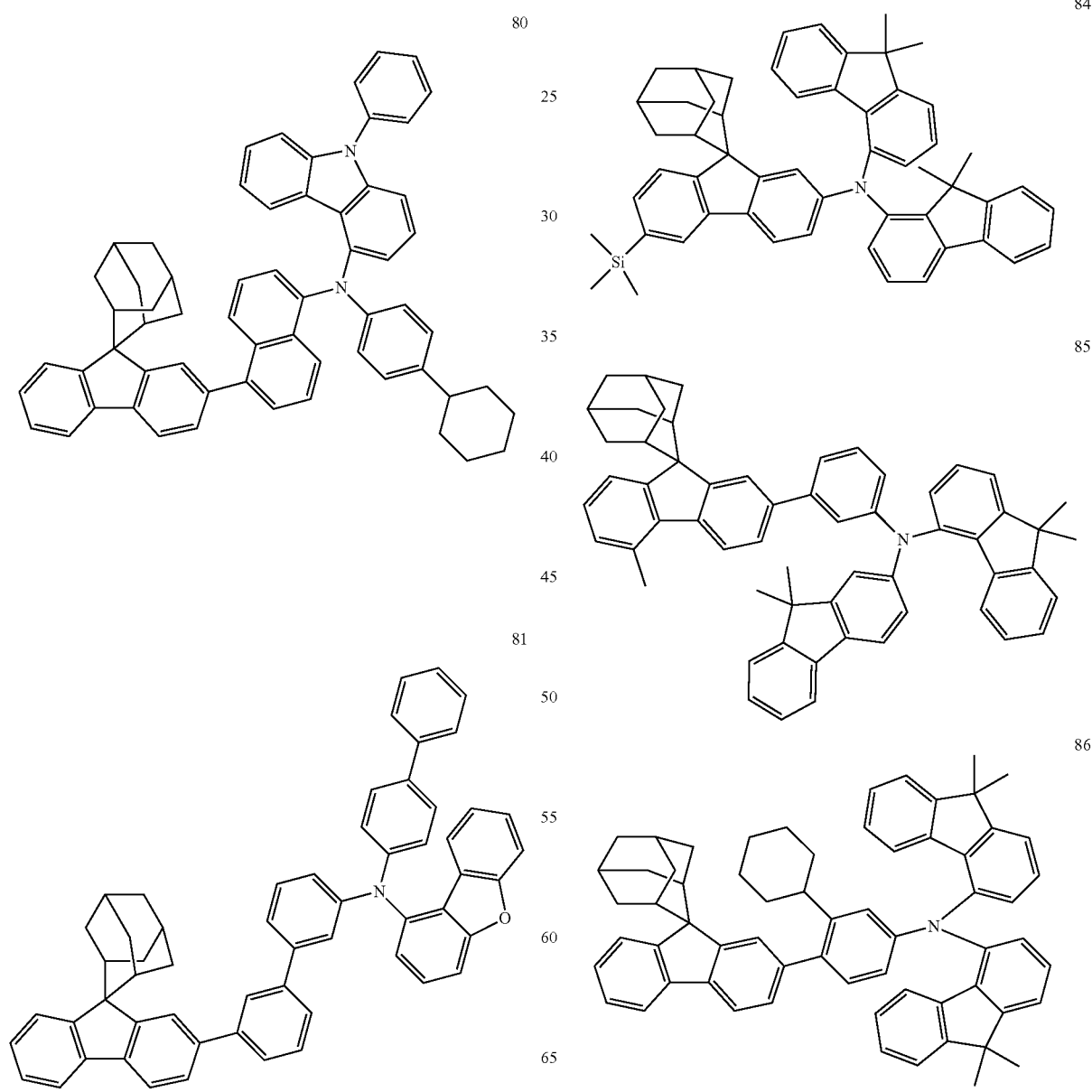

88
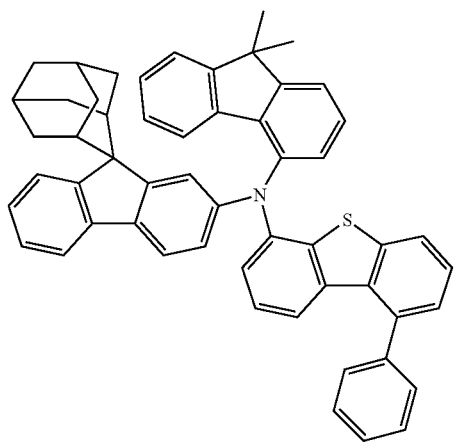
89
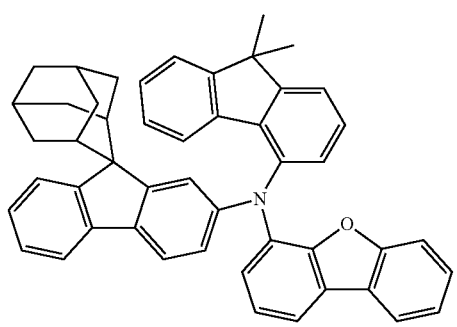
90
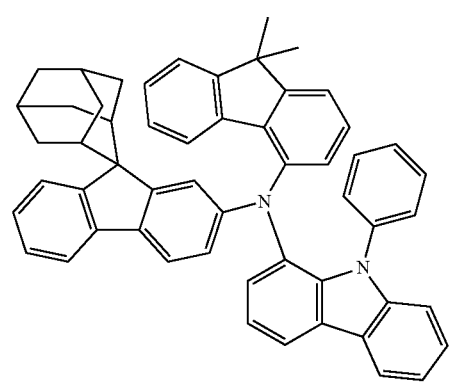
91
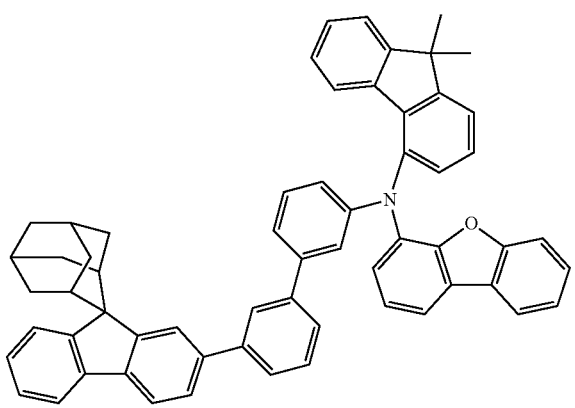
92
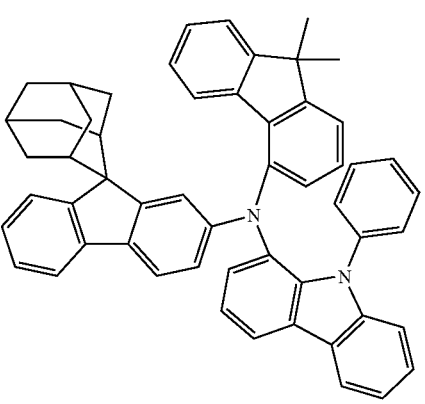
93
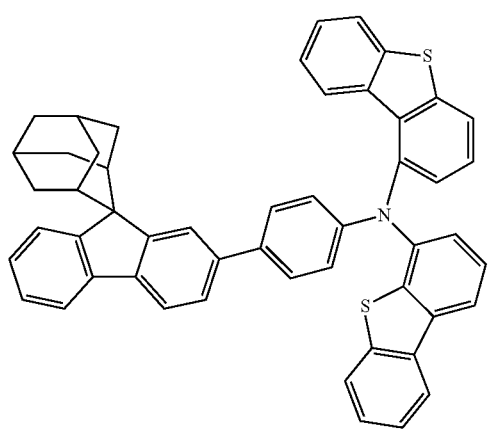
94
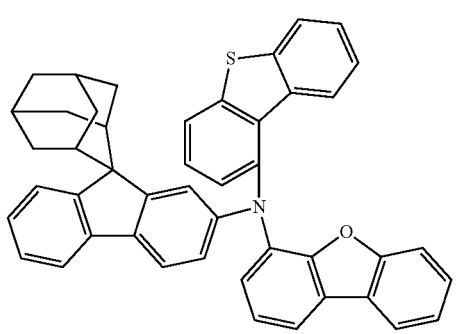
95
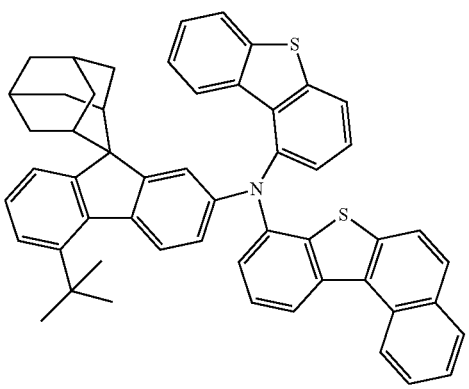

96 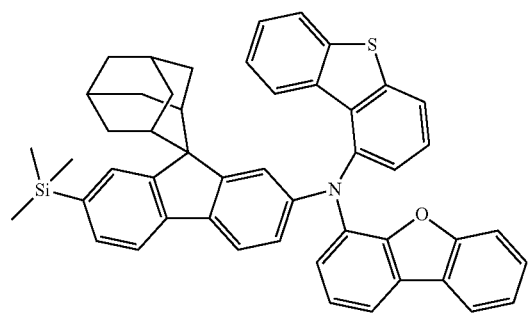
97 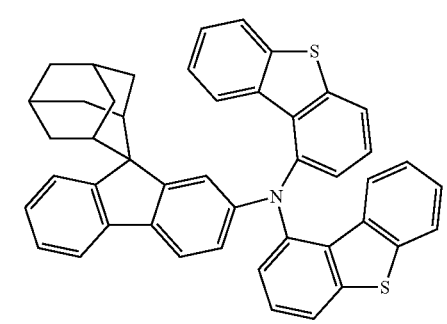
98 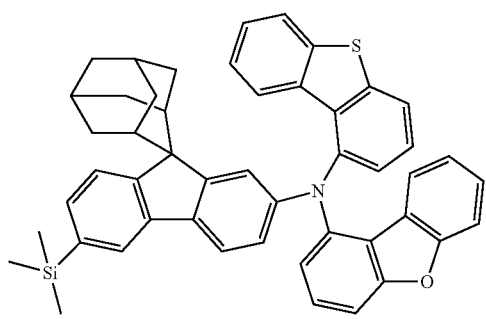
99 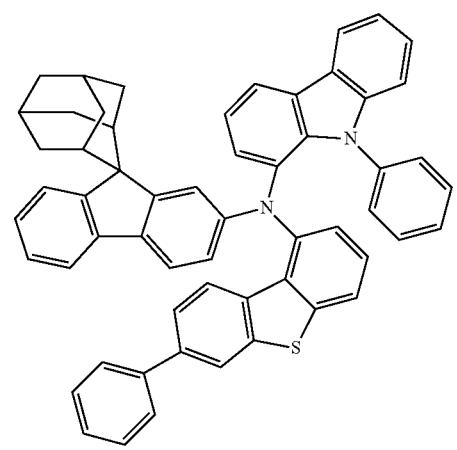
100 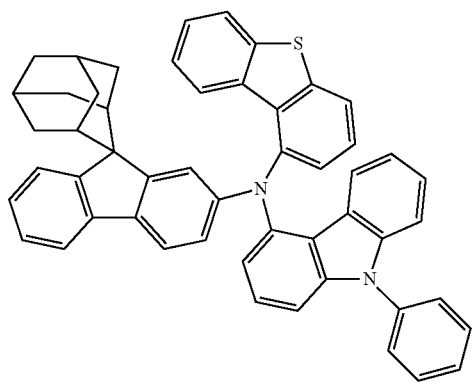
101 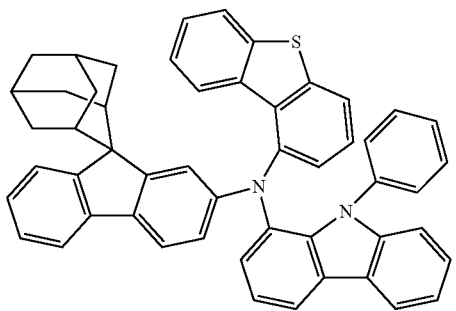
102 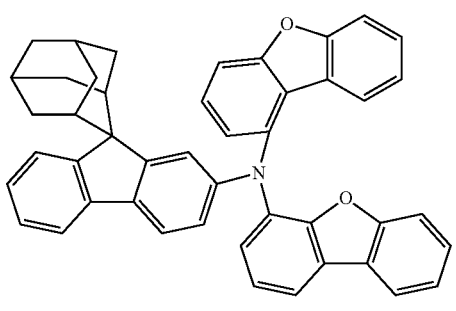
103 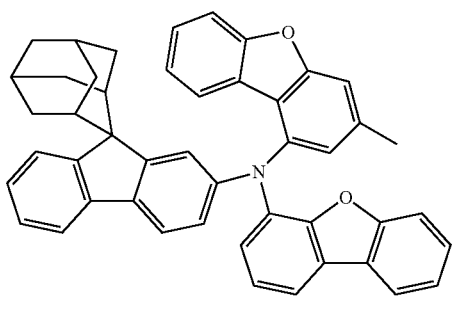
104 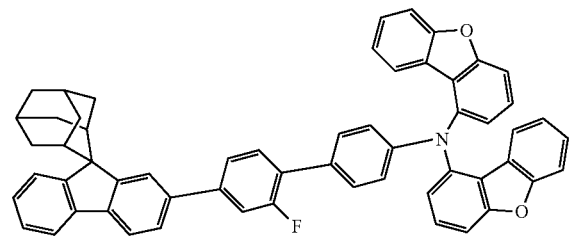

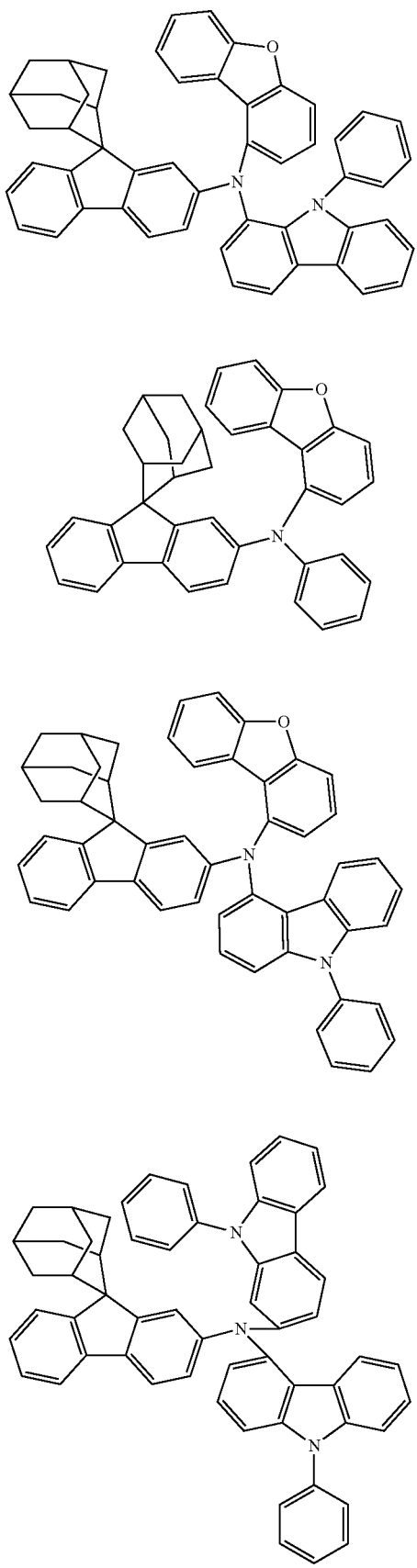
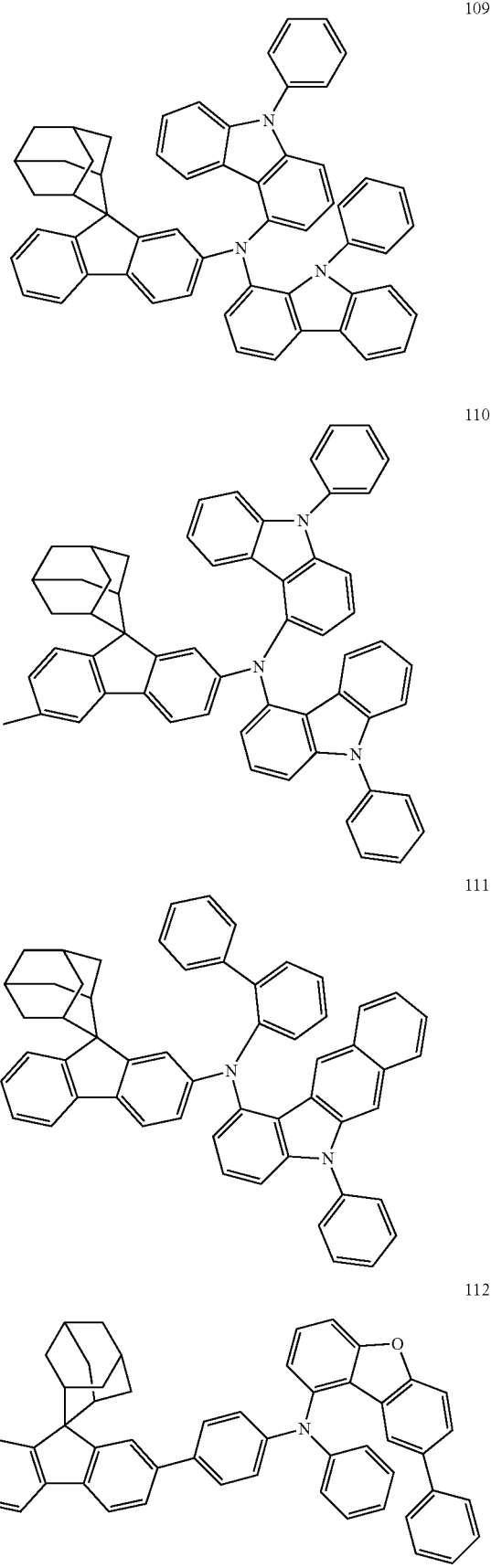

-continued
113
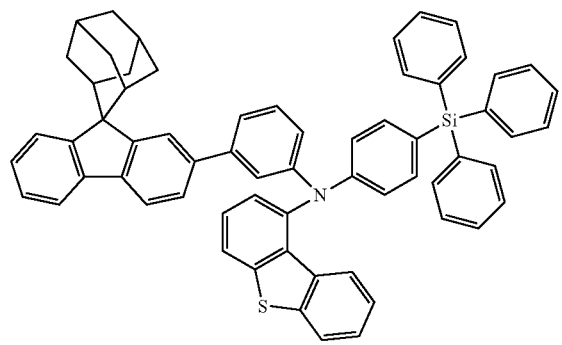
114
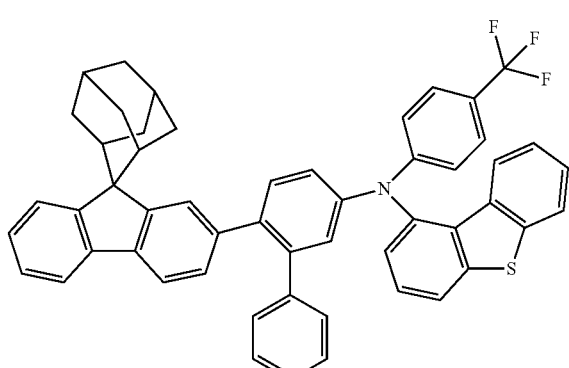
115
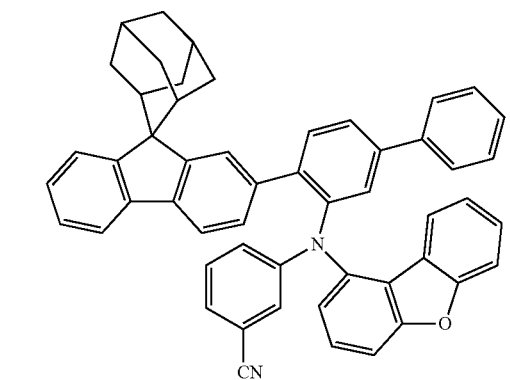
116
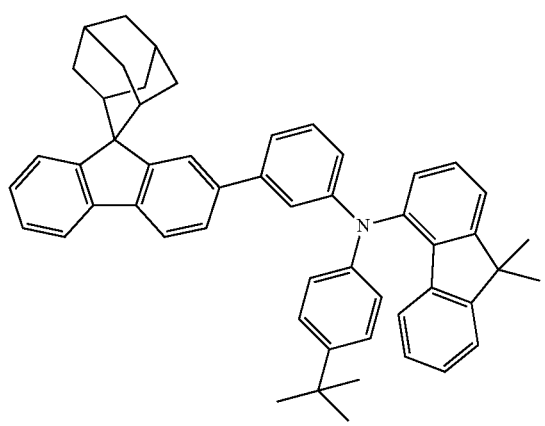
-continued
117
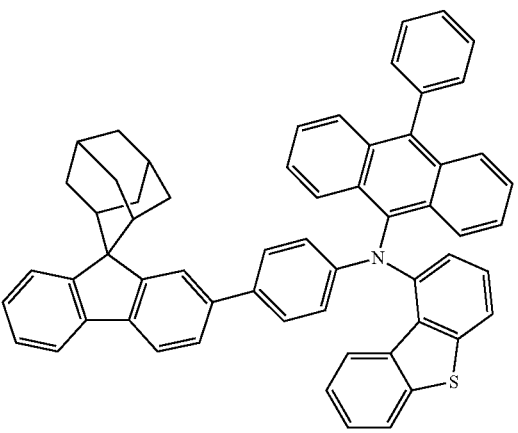
118
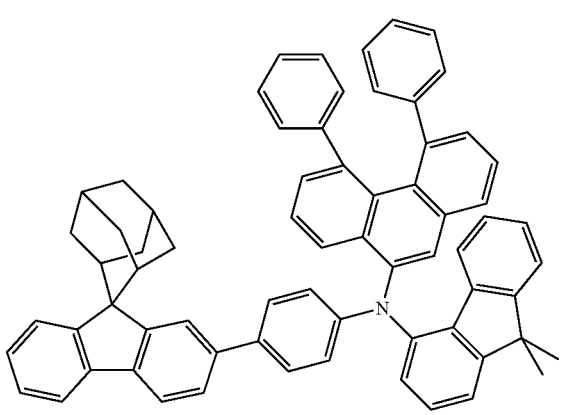
119
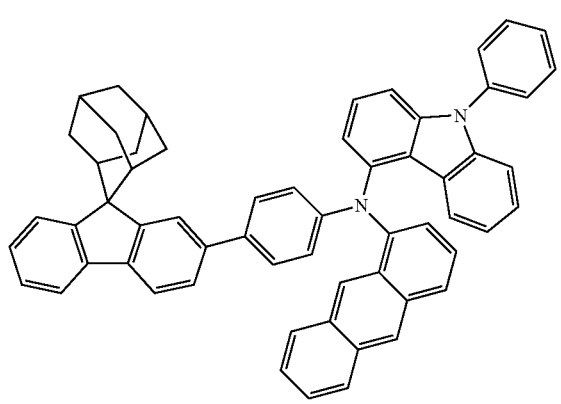
120
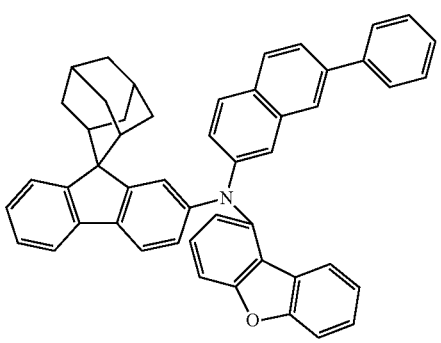

121
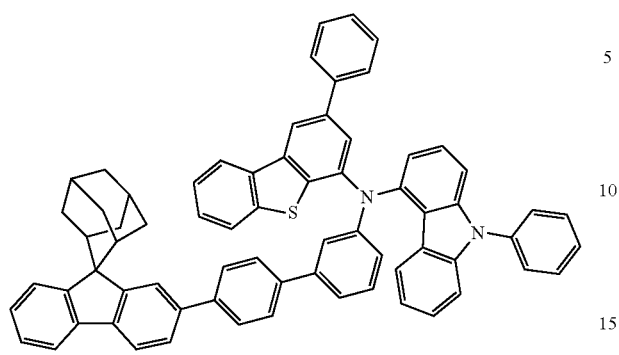
122
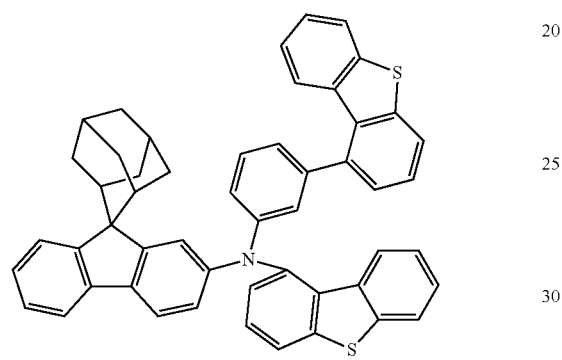
123
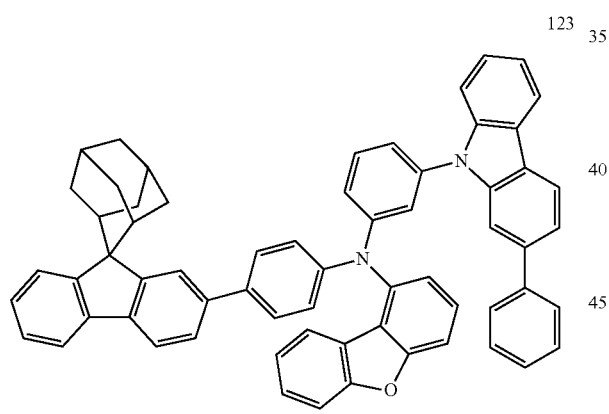
124
125
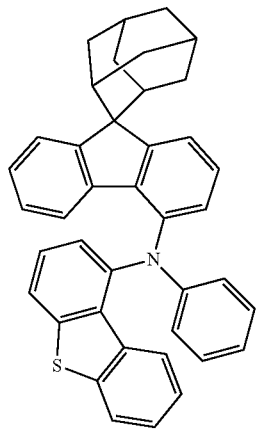
126
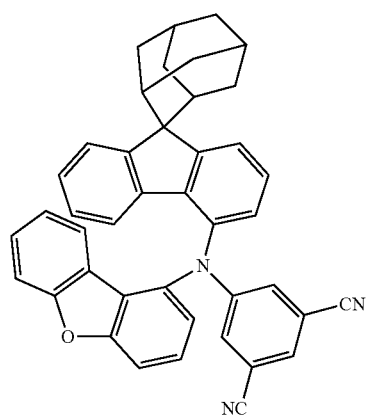
127
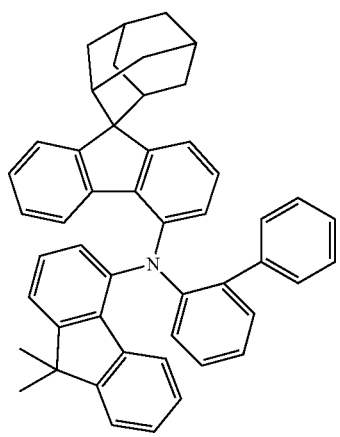

128
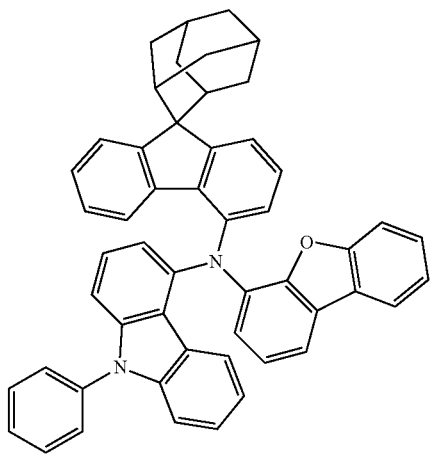
129
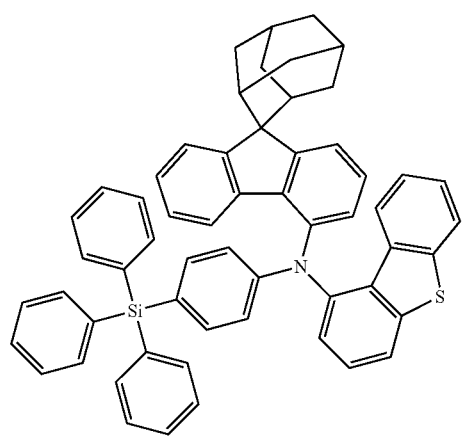
130
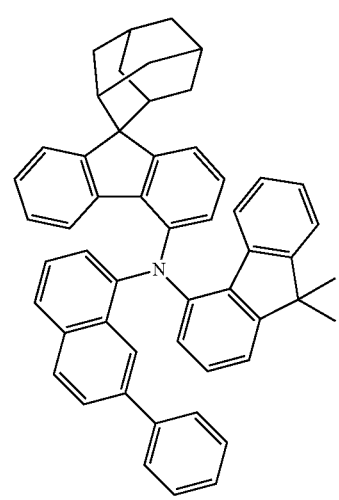
131
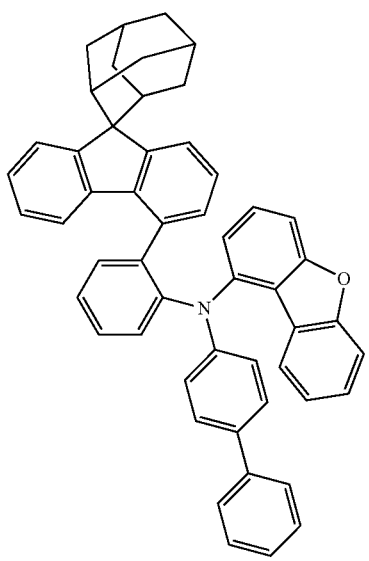
132
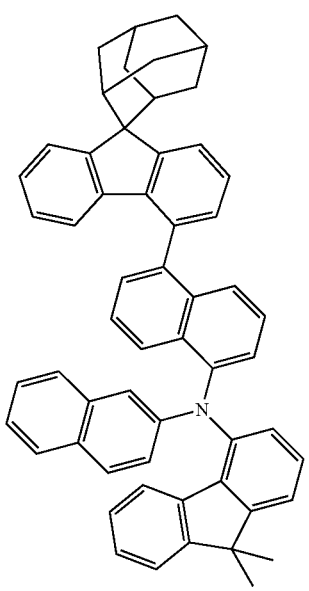

133
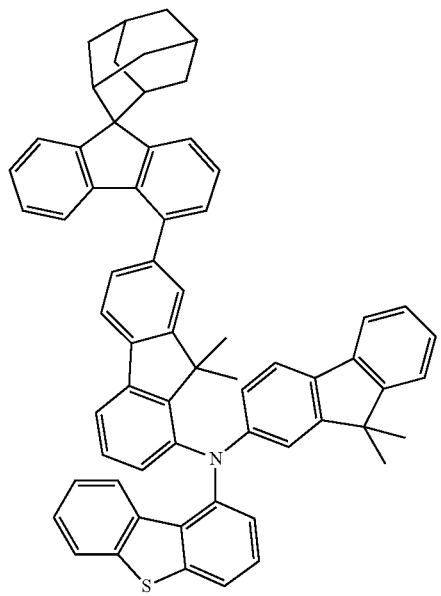
135
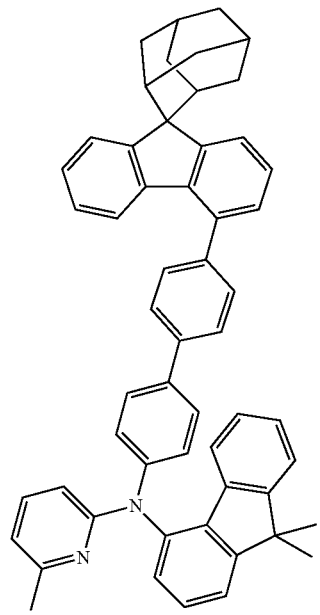
136
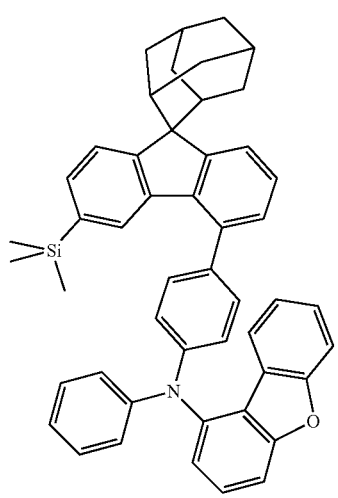
137
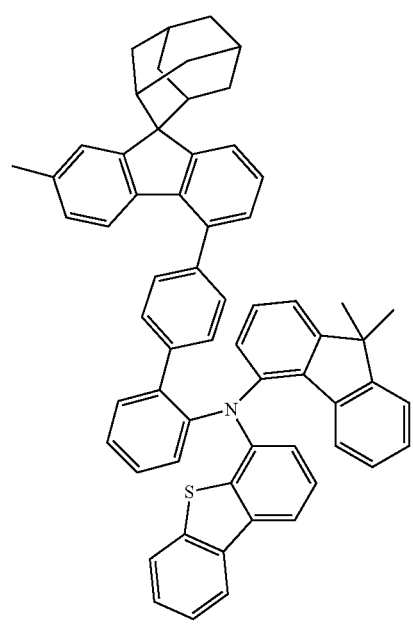
138
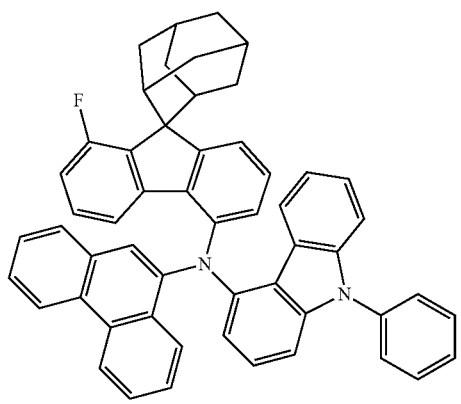

-continued
139
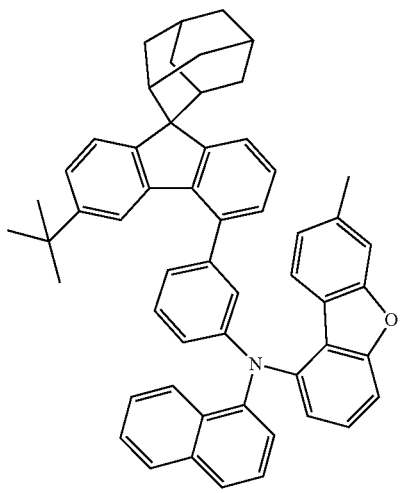
140
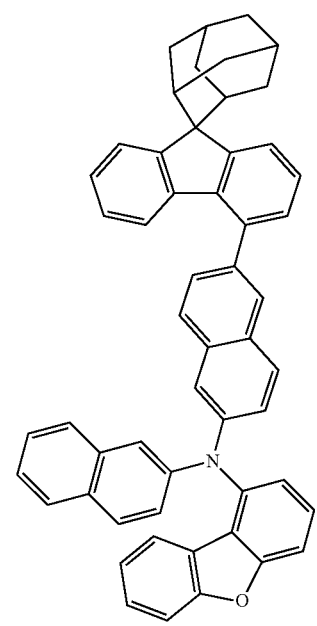
141
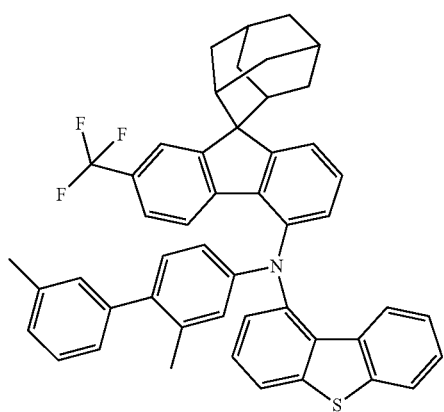
-continued
142
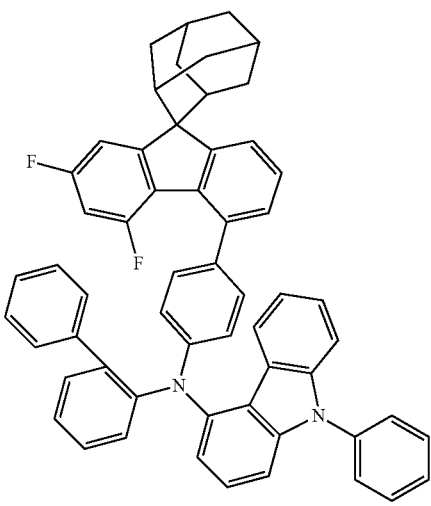
143
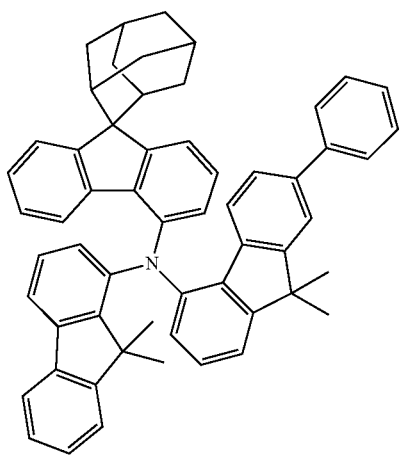
144
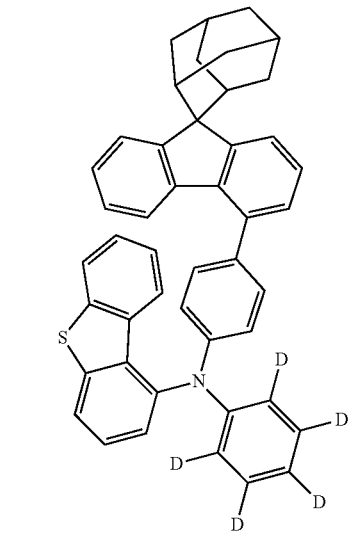

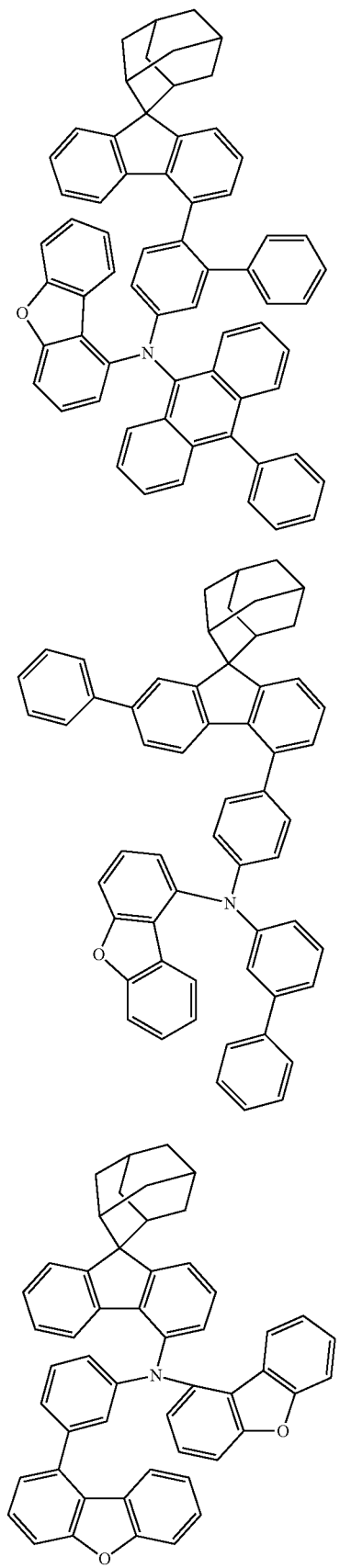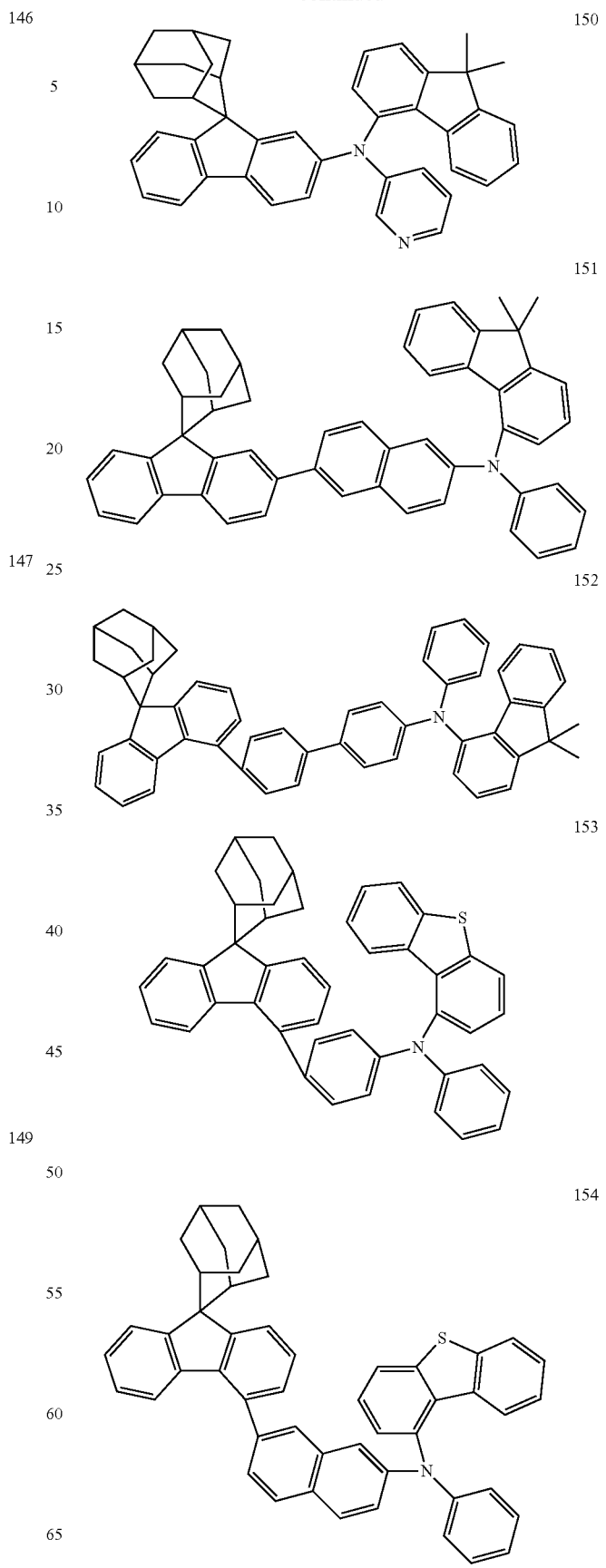

155
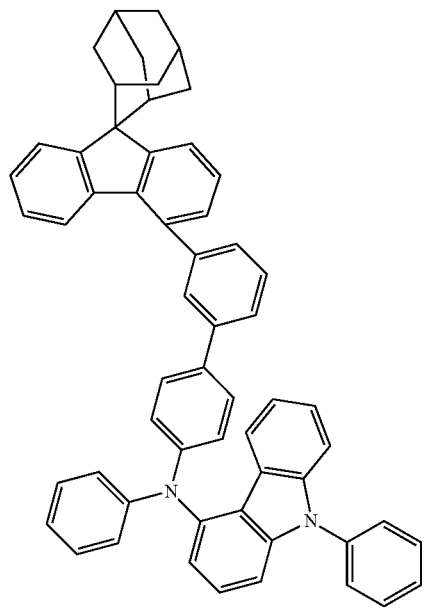
156
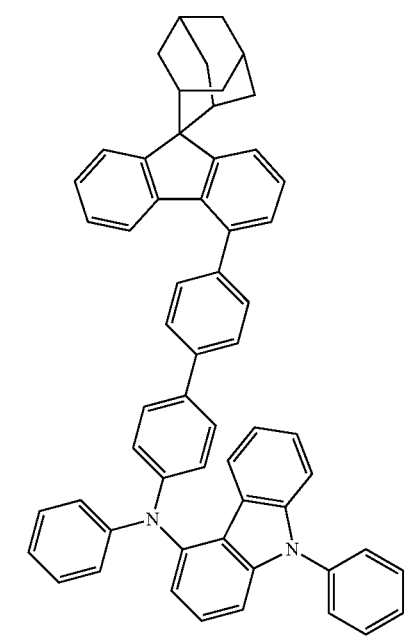
161
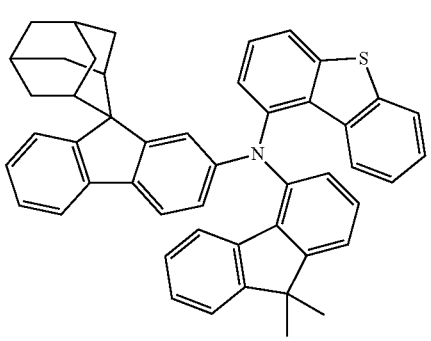
162
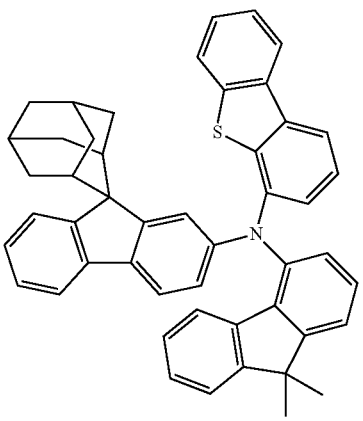
163
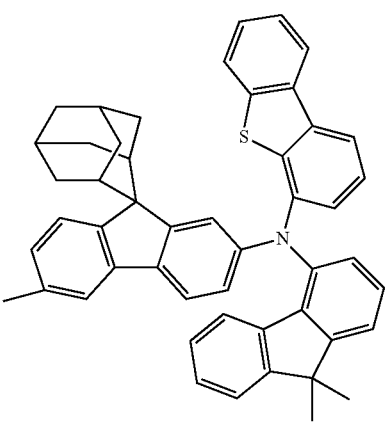
164
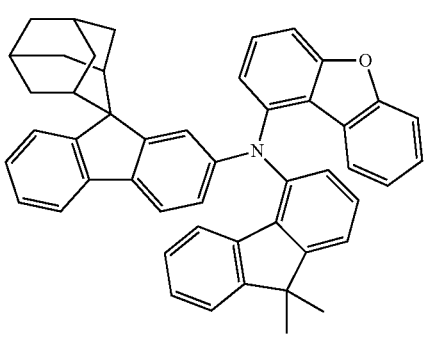
165
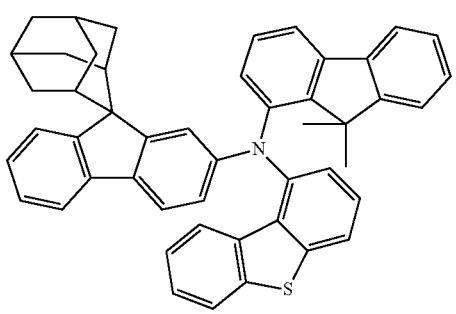

166
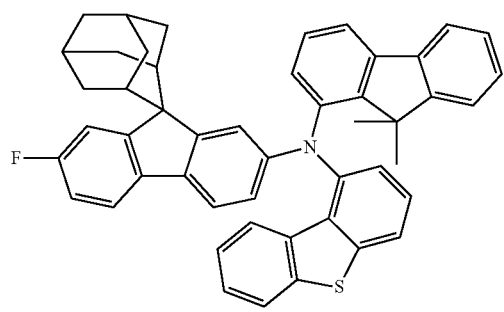
167
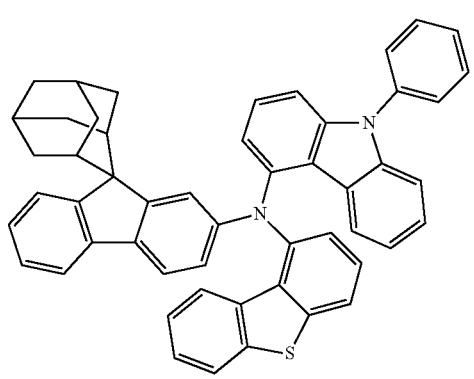
168
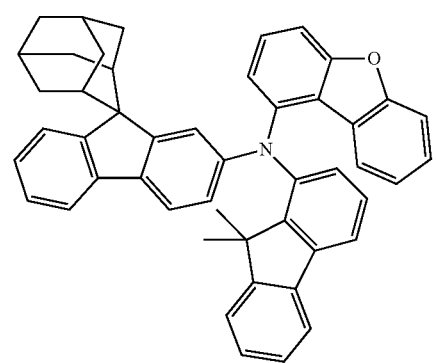
169
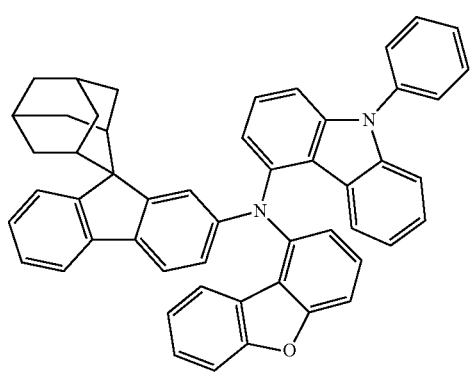
170
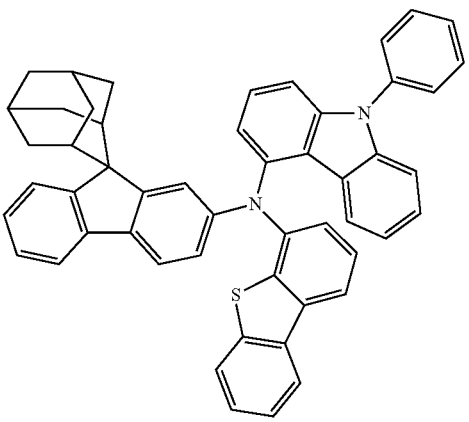
171
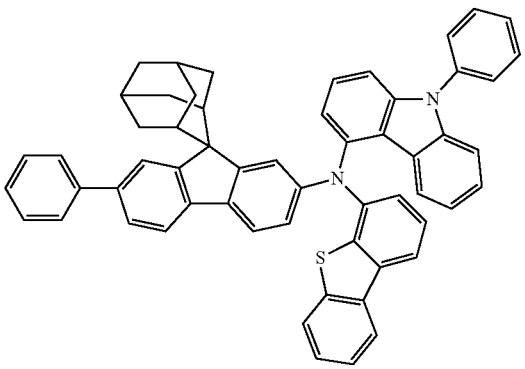
172
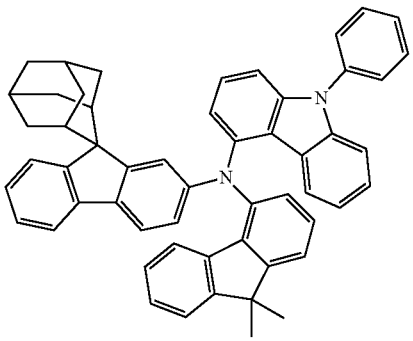
173
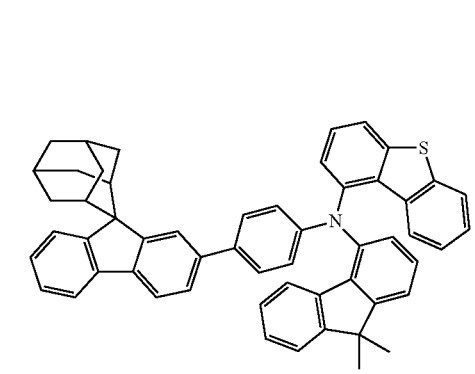

174
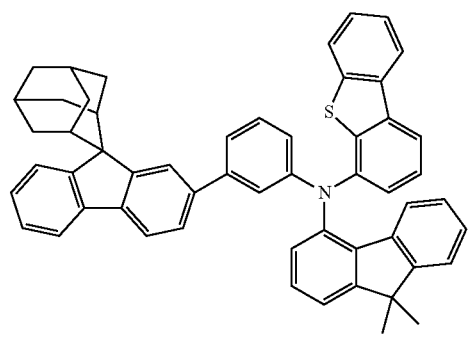
175
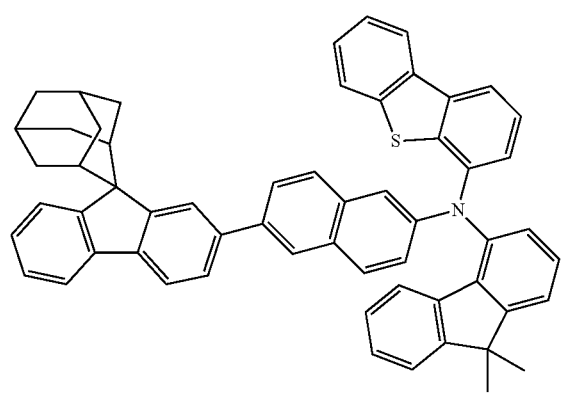
176
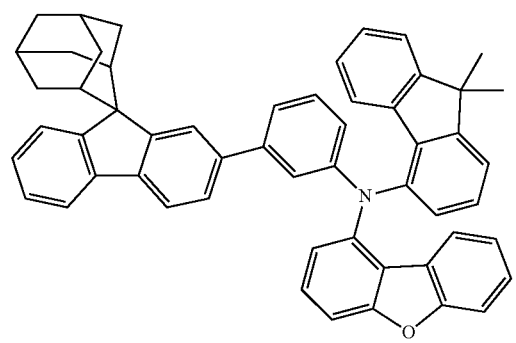
177
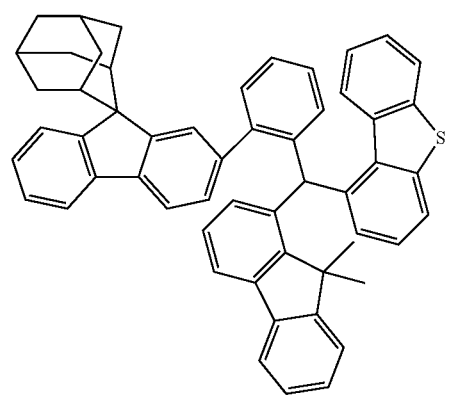
178
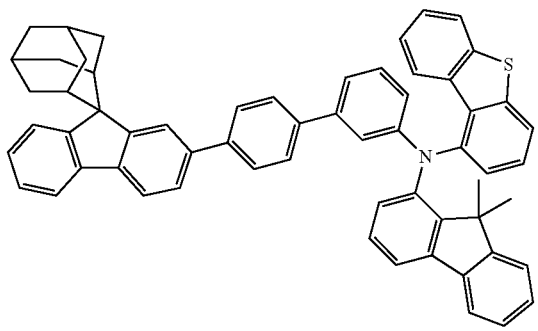
179
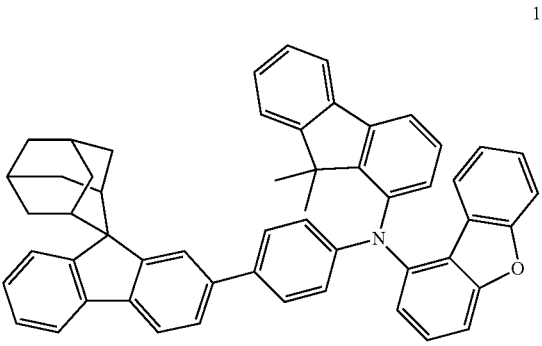
180
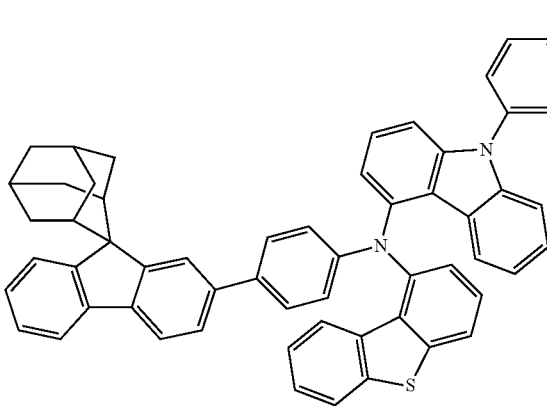
181
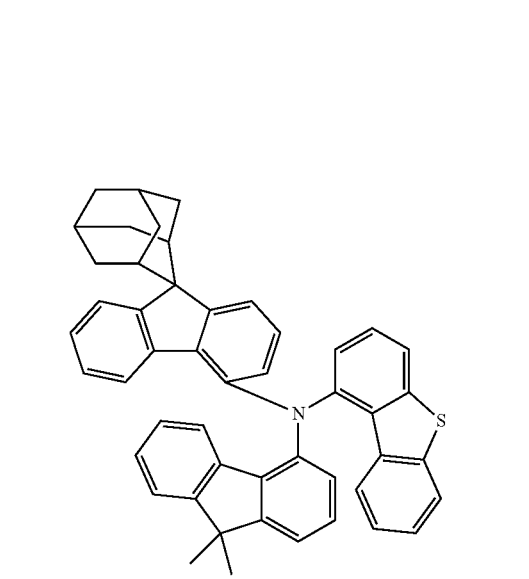

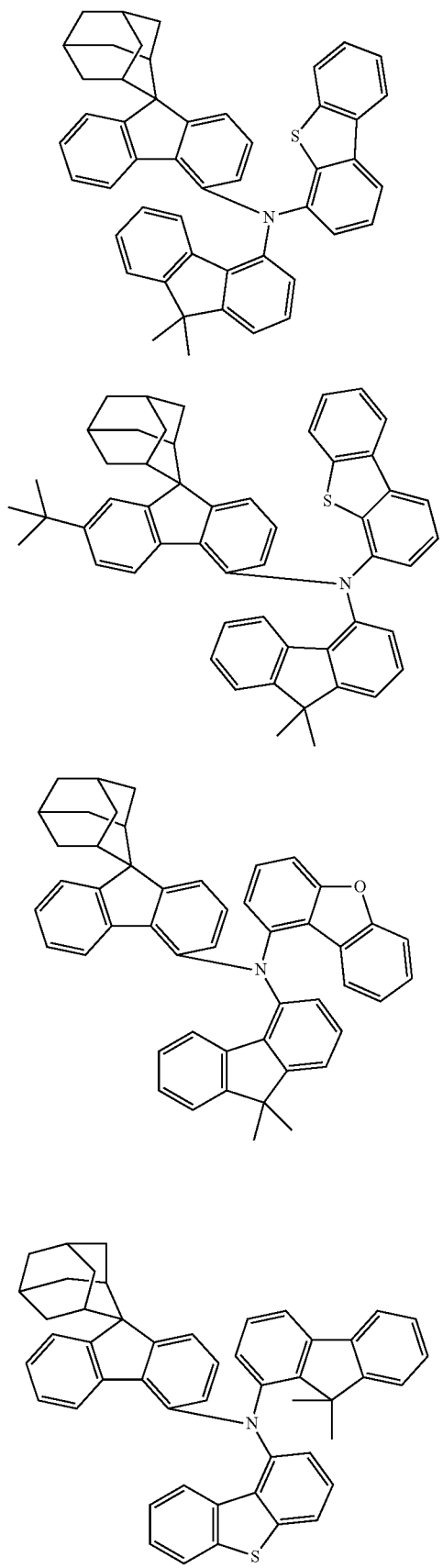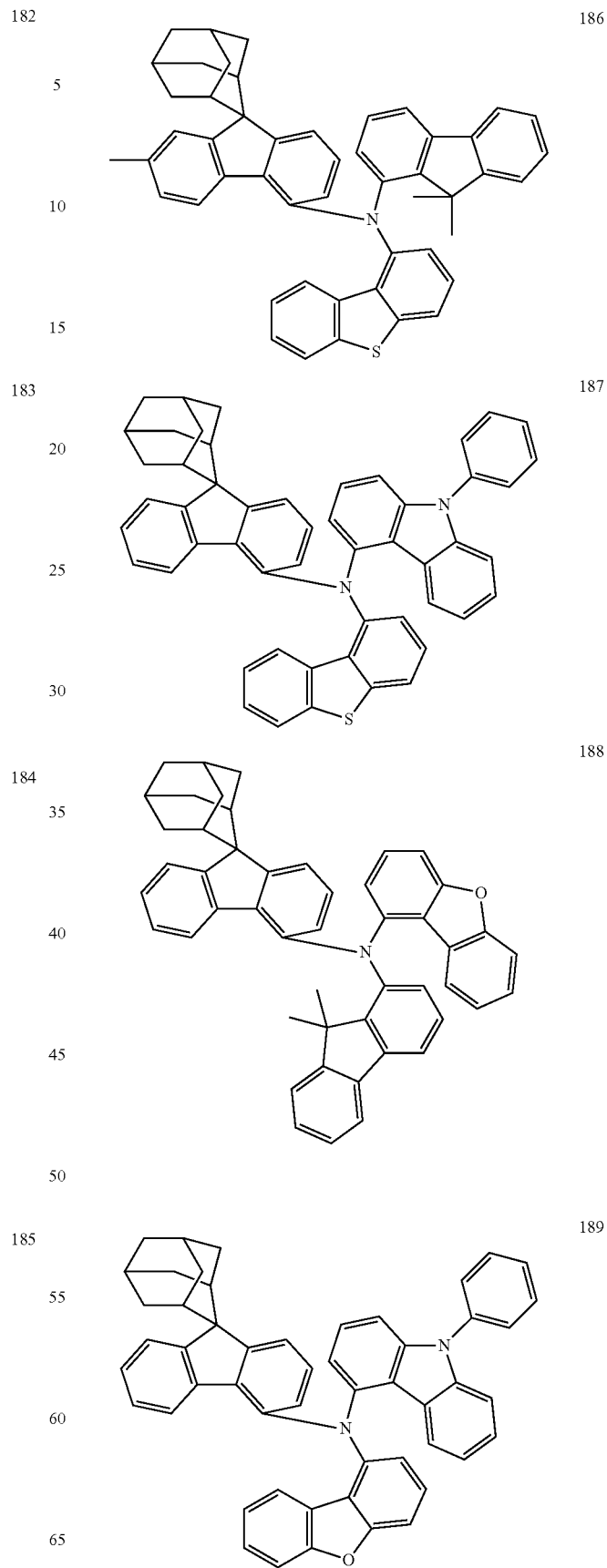

191
-continued
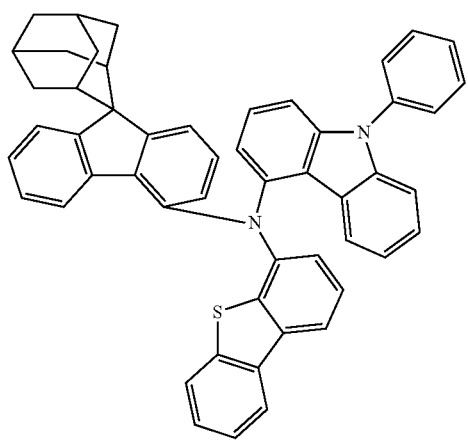
190
191
192
192
-continued
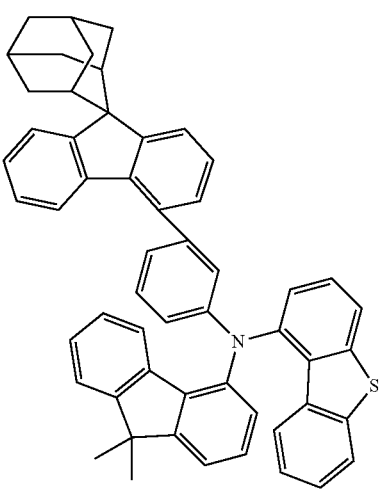
193
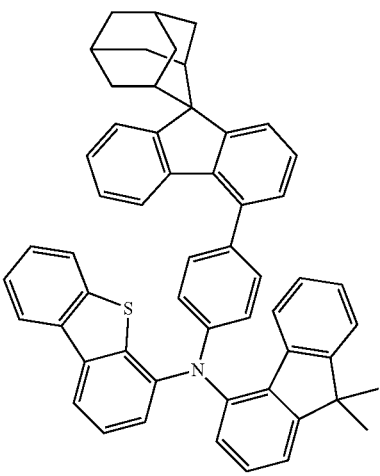
194
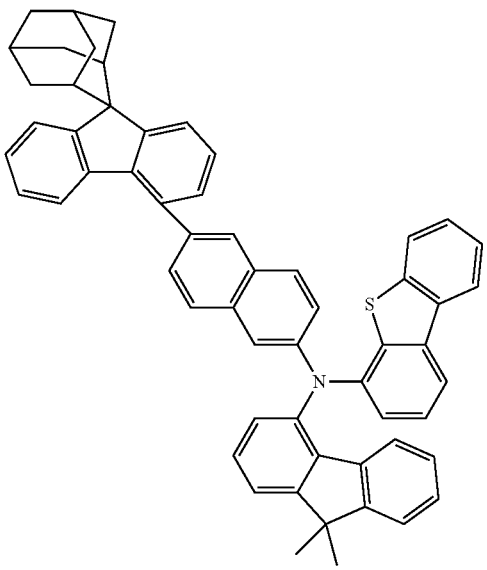
195

193
-continued

196
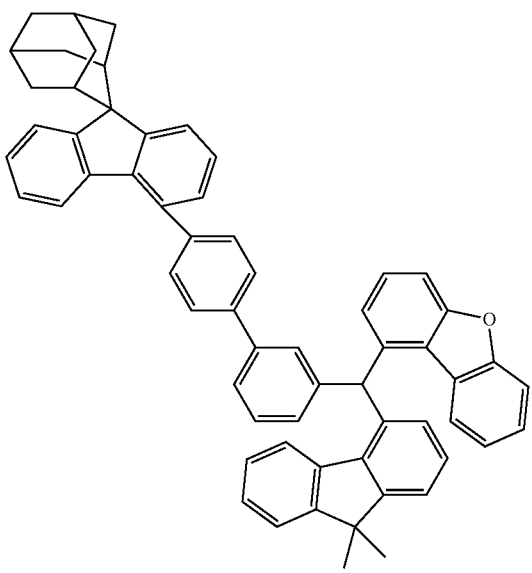

197
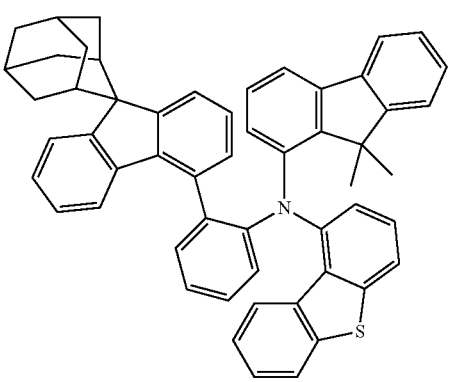

198
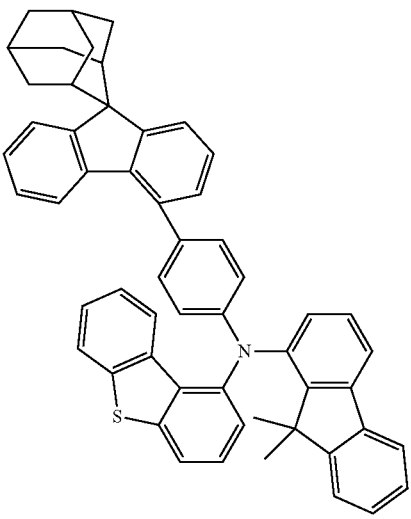

194
-continued

199
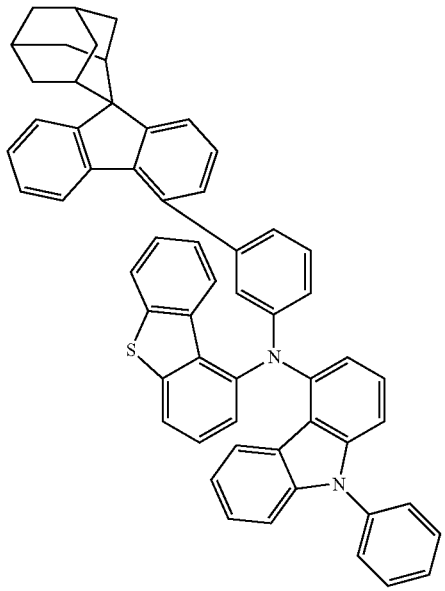

200
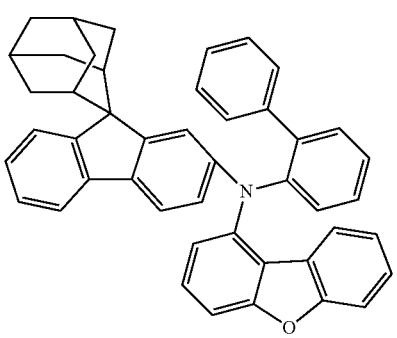

7. An electronic component, including an anode and a cathode which is arranged oppositely to the anode, and a functional layer disposed between the anode and the cathode; wherein the functional layer comprises the nitrogen-containing compound of claim 1.

8. The electronic component of claim 7, wherein the functional layer includes a hole transporting layer, and the hole transporting layer comprises the nitrogen-containing compound.

9. The electronic component of claim 7, wherein the electronic component is an organic electroluminescent device or a photoelectric conversion device.

10. An electronic device, including the electronic component of claim 7.

11. The nitrogen-containing compound of claim 1, wherein $R_3$ is selected from deuterium, fluorine, cyano, methyl, tert-butyl, trifluoromethyl, cyclopentyl, cyclohexyl, trimethylsilyl, or phenyl.

* * * * *